(12) United States Patent
Aubart et al.

(10) Patent No.: US 7,919,528 B2
(45) Date of Patent: Apr. 5, 2011

(54) PEPTIDE DEFORMYLASE INHIBITORS

(75) Inventors: Kelly M. Aubart, Collegeville, PA (US); Andrew B. Benowitz, Collegeville, PA (US); Siegfried B. Christensen, IV, Collegeville, PA (US); Joseph M. Karpinski, Collegeville, PA (US); Jinhwa Lee, Collegeville, PA (US); Domingos J. Silva, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 555 days.

(21) Appl. No.: 10/512,926

(22) PCT Filed: May 30, 2003

(86) PCT No.: PCT/US03/17054
§ 371 (c)(1),
(2), (4) Date: Oct. 29, 2004

(87) PCT Pub. No.: WO03/101442
PCT Pub. Date: Dec. 11, 2003

(65) Prior Publication Data
US 2005/0222412 A1 Oct. 6, 2005

Related U.S. Application Data

(60) Provisional application No. 60/384,457, filed on May 31, 2002.

(51) Int. Cl.
| | | |
|---|---|---|
| C07C 239/08 | (2006.01) | |
| C07C 243/22 | (2006.01) | |
| C07D 213/77 | (2006.01) | |
| C07D 237/22 | (2006.01) | |
| C07D 239/42 | (2006.01) | |
| C07D 251/40 | (2006.01) | |
| C07D 487/04 | (2006.01) | |
| A61K 31/16 | (2006.01) | |
| A61K 31/18 | (2006.01) | |
| A61K 31/44 | (2006.01) | |
| A61K 31/505 | (2006.01) | |
| A61K 31/506 | (2006.01) | |
| A61K 31/53 | (2006.01) | |
| A61K 31/495 | (2006.01) | |

(52) U.S. Cl. ............ 514/613; 514/614; 514/231.5; 514/243; 514/275; 514/462; 564/159; 564/160; 544/183; 544/111; 544/330; 549/462

(58) Field of Classification Search .......... 564/159, 564/160; 514/613, 614, 231.5, 243, 275, 514/462; 544/183, 111, 330; 549/462
See application file for complete search history.

(56) References Cited

U.S. PATENT DOCUMENTS

| | | | |
|---|---|---|---|
| 5,691,382 A | 11/1997 | Crimmin et al. | |
| 6,013,792 A | 1/2000 | Castelhano et al. | |
| 6,028,110 A | 2/2000 | Miller et al. | |
| 6,037,472 A | 3/2000 | Castelhano et al. | |
| 7,019,003 B2 * | 3/2006 | Xiang et al. | 514/234.8 |

FOREIGN PATENT DOCUMENTS

| | | |
|---|---|---|
| WO | WO00/35440 | 6/2000 |
| WO | WO00/42026 | 7/2000 |
| WO | WO 02/16315 | 2/2002 |
| WO | WO02 070541 | 9/2002 |
| WO | WO2004/052919 | 6/2004 |
| WO | WO 2005/005456 | 1/2005 |
| WO | WO2005/017124 | 2/2005 |
| WO | WO2006/055663 | 5/2005 |
| WO | WO2009/061879 | 5/2009 |

OTHER PUBLICATIONS

Snyder et al., J. Med. Liban 48(4): 208-214, 2000.*
Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Groche, Dieter, "Isolation and Crystallization of Functionally Competent *Escherichia coli* Peptide Deformylase forms Containing either Iron or Nickel in the Active Site," *Biochemical and Biophysical Research Communications*, 246, 342-346 (1998) Article No. RC988616.
Chen, Dawn Z., "Actinonin, a Naturally Occurring Antibacterial Agent, Is a Potent Deformylase Inhibitor," *Biochemistry* 39, 1256-1263 (2000).
Giglione, Carmela, "Peptide Deformylase as a target for new generation, broad spectrum antimicrobial agents," 36(6), 1197-1205 (2000).
Huntington, Kristi M., "Synthesis and Antibacterial Activity of Peptide Deformylase Inhibitors," *Biochemistry*, 39, 4543-4551 (2000).
Apfel, Christian, "Hydroxamic Acid Derivatives as Potent Peptide Deformylase Inhibitors and Antibacterial Agents," *J. Med. Chem*, 43, 2324-2331 (2000).
Clements, John M., "Antibiotic Activity and Characterization of BB-3497, a Novel Peptide Deformylase Inhibitor," *Antimicrobial Agents and Chemotherapy*, 45(2), 563-570 (Feb. 2001).

* cited by examiner

*Primary Examiner* — Venkataraman Balasubramanian
(74) *Attorney, Agent, or Firm* — Laura K. Madden; Theodore R. Furman

(57) ABSTRACT

Novel PDF inhibitors and novel methods for their use are provided.

44 Claims, No Drawings

PEPTIDE DEFORMYLASE INHIBITORS

This application claims the benefit of U.S. Provisional Application No. 60/384,457, filed May 31, 2002.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1).

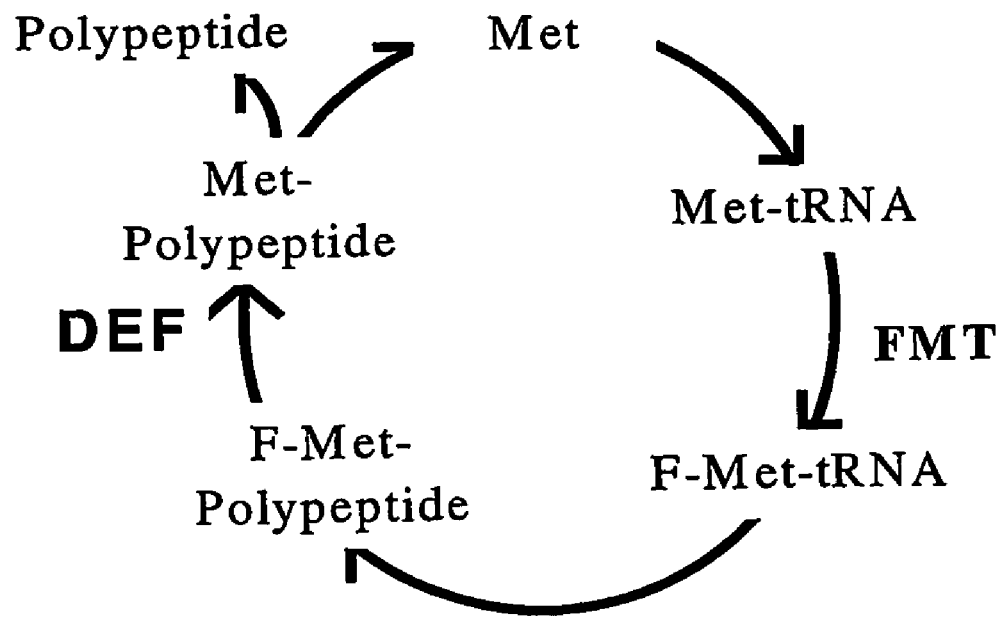
Figure 1. The methionine cycle.

To date, polypeptide deformylase homologous genes have been found in bacteria, in chloroplast-containing plants, in mice and in human. The plant proteins are nuclear encoded but appear to carry a chloroplast localisation signal. This is consistent with the observation that chloroplast RNA and protein synthesis processes are highly similar to those of eubacteria While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165-168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749-761, 1997).

PDF is recognized to be an attractive antibacterial target, as this enzyme has been demonstrated to be essential for bacterial growth in vitro (Mazel, D. et al., EMBO J. 13 (4), 914-923, 1994), is not believed to be involved in eukaryotic protein synthesis (Rajagopalan et al., J. Am. Chem. Soc. 119, 12418-12419, 1997), and is universally conserved in prokaryotes (Kozak, M., Microbiol. Rev. 47, 1-45, 1983). Therefore PDF inhibitors can potentially serve as broad spectrum antibacterial agents.

SUMMARY OF THE INVENTION

The present invention involves novel antibacterial compounds represented by Formula (1) hereinbelow and their use as PDF inhibitors.

DETAILED DESCRIPTION OF THE INVENTION

In one aspect of the present invention, there is provided a compound of formula (1):

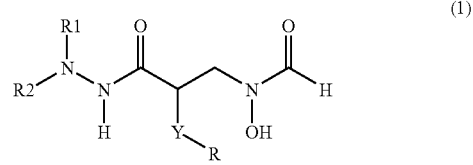

(1)

wherein:
R is selected from the group consisting of:
  $C_{2-6}$ alkyl (optionally substituted by alkoxy, halogen, or $C_{1-3}$ alkylsulfanyl); $C_{2-6}$ alkenyl (optionally substituted by alkoxy, halogen, or $C_{1-3}$ alkylsulfanyl); $C_{2-6}$ alkynyl (optionally substituted by alkoxy, halogen, or $C_{1-3}$ alkylsulfanyl); $(CH_2)_n$—$C_{3-6}$ carbocycle (optionally substituted by alkoxy, halogen, or $C_{1-3}$ alkylsulfanyl); and $(CH_2)_n$—R4, wherein R4 is selected from the group consisting of phenyl, furan, benzofuran, thiophene, benzothiophene, tetrahydrofuran, tetrahydropyran, dioxane, 1,4-benzodioxane or benzo[1,3]dioxole; R4 is optionally substituted by one or more substituent selected from Cl, Br, I, $C_{1-3}$ alkyl (optionally substituted by one to three F) and $C_{1-2}$ alkoxy (optionally substituted by one to three F);

R1 and R2 are independently selected from the group consisting of:
  hydrogen, $C_{1-3}$ substituted alkyl, $C_{2-3}$ substituted alkenyl, $C_{2-3}$ substituted alkynyl, $(CH_2)_n$—$C_{3-6}$ substituted carbocycle, aryl, heteroaryl, and heterocyclic;
Y represents O, $CH_2$ or a covalent bond; and
n is an integer from 0 to 2;
or a salt, solvate, or physiologically functional derivative thereof.

In this invention the most preferred R2 group is hydrogen. In this invention the most preferred absolute configuration of compounds of the formula (1) is indicated below:

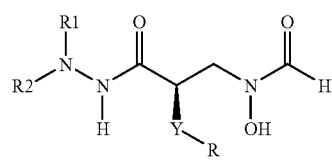

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, hexyl and the like.

As used herein, the term "substituted alkyl" refers to a straight or branched chain saturated hydrocarbon radical, optionally substituted with substituents selected from the group that includes $C_{1-3}$ alkyl (optionally substituted by one to three fluorines), $C_{2-3}$ alkenyl, $C_{2-3}$ alkyl, $C_{1-2}$ alkoxy (optionally substituted by one to three fluorines), sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen, multiple degrees of substitution being allowed.

As used herein, the term "alkenyl" refers to a straight or branched chain hydrocarbon radical having at least one carbon-carbon double bond. Examples of "alkenyl". as used herein include, but are not limited to, ethenyl and propenyl.

As used herein, the term "substituted alkenyl" refers to a straight or branched chain hydrocarbon radical having at least one carbon-carbon double bond, optionally substituted with substituents selected from the group which includes $C_{1-3}$ alkyl (optionally substituted by one to three F), amino, aryl, cyano and halogen, multiple degrees of substitution being allowed.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally substituted with substituents selected from the group which includes $C_{1-3}$ alkyl (optionally substituted by one to three F), amino, aryl and halogen, multiple degrees of substitution being allowed.

As used herein, the term "halogen" refers to fluorine (F), chlorine (Cl), bromine (Br), or iodine (I), and "halo" refers to the halogen radicals fluoro, chloro, bromo and iodo.

As used herein, the term "carbocycle" refers to a non-aromatic cyclic hydrocarbon radical having from three to seven carbon atoms. For carbocycles with five-to seven-membered rings, a ring double bond is allowed. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical having from three to seven carbon atoms, and which is optionally substituted with substituents selected from the group which includes $C_{1-3}$ alkyl (optionally substituted by one to three F), $C_{2-3}$ alkenyl, $C_{2-3}$ alkynyl, $C_{1-2}$ alkoxy (optionally substituted by one to three F), sulfanyl, sulfnyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen, multiple degrees of substitution being allowed. For carbocycles with five-to seven-membered rings, a ring double bond is allowed.

As used herein, the term "aryl" refers to an optionally substituted benzene ring or to an optionally substituted benzene ring fused to one or more optionally substituted benzene rings to form a ring system. Exemplary optional substituents include $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring or ring system may be optionally fused to one or more optionally substituted aryl rings (including benzene rings), carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six membered aromatic ring containing one or more heteroatomic substitutions selected from S, SO, $SO_2$, N, or N-oxide, or to such an aromatic ring fused to one or more optionally substituted rings, such as heteroaryl rings, aryl rings, heterocyclic rings, or carbocycle rings (e.g., a bicyclic or tricyclic ring system). Examples of optional substituents are selected from the group which includes $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido, multiple degrees of substitution being allowed. Examples of "heteroaryl" groups used herein include, but are not limited to, benzoimidazolyl, benzothiazolyl, benzoisothiazolyl, benzothiophenyl, benzopyrazinyl, benzotriazolyl, benzotriazinyl, benzo[1,4]dioxanyl, benzofuranyl, 9H-α-carbolinyl, cinnolinyl, 2,3-dihydro-[1,4]dioxino[2,3-b]-pyridinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrazolopyridinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with substituents selected from the group which includes $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring can be saturated or have one or more degrees of unsaturation. Such a ring may be optionally fused to one or more other optionally substituted "heterocyclic" ring(s), aryl ring(s), heteroaryl ring(s), or carbocycle ring(s). Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, dihydroquinoxalinyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, isoindole-1,3-dionyl, and the like.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy, and t-butoxy.

As used herein the term "aralkoxy" refers to the group —$OR_aR_b$, where $R_a$ is alkyl and $R_b$ is aryl as defined above.

As used herein the term "aryloxy" refers to the group —$OR_a$, where $R_a$ is aryl as defined above.

As used herein, the term "mercapto" refers to the group —SH.

As used herein, the term "sulfanyl" refers to the group —$SR_a$, where $R_a$ is substituted alkyl, substituted carbocycle, aryl, heteroaryl or heterocyclic, as defined above.

As used herein, the term "sulfinyl" refers to the group —$S(O)R_a$, where $R_a$ is substituted alkyl, substituted carbocycle, aryl, heteroaryl or heterocyclic, as defined above.

As used herein, the term "sulfonyl" refers to the group —$S(O)_2R_a$, where $R_a$ is substituted alky, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_a$ where $R_a$ is substituted alkyl, substituted carbocycle, aryl, heteroaryl or heterocyclic, as defined above.

As used herein, the term "carboxyamide" refers to the group —$NHC(O)R_a$ where $R_a$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —C(O)NH$_2$. The aminocarbonyl group is optionally substituted by substituted alkyl, substituted carbocycle, aryl, heteroaryl or heterocyclic, as defined above.

As used herein, the term "ureido" refers to the group —NHC(O)NHR$_a$ wherein R$_a$ is hydrogen, alkyl, carbocycle or aryl as defined above.

As used herein, the term "guanidino" refers to the group —NHC(=NH)NH$_2$.

As used herein, the term "acyl" refers to the group —C(O)R$_a$, where R$_a$ is alkyl, carbocycle, or heterocyclic as defined herein.

As used herein, the term "aroyl" refers to the group —C(O)R$_a$, where R$_a$ is aryl as defined herein.

As used herein, the term "heteroaroyl" refers to the group —C(O)R$_a$, where R$_a$ is heteroaryl as defined herein.

As used herein, the term "acyloxy" refers to the group —OC(O)R$_a$, where R$_a$ is alkyl, carbocycle, or heterocyclic as defined herein.

As used herein, the term "aroyloxy" refers to the group —OC(O)R$_a$, where R$_a$ is aryl as defined herein.

As used herein, the term "heteroaroyloxy" refers to the group —OC(O)R$_a$, where R$_a$ is heteroaryl as defined herein.

Also included in the present invention are pharmaceutically acceptable salts and complexes, such as the hydrochloride, hydrobromide and trifluoroacetate salts and the sodium, potassium and magnesium salts. The compounds of the present invention may contain one or more asymmetric carbon atoms and may exist in racemic and optically active forms. All of these compounds and diastereomers are contemplated to be within the scope of the present invention.

Preferred compounds useful in the present invention are selected from the group consisting of:

N-Hydroxy-N-[(R)-2-(N'-pyridin-2-yl-hydrazinocarbonyl)-heptyl]-formamide.
N-Hydroxy-N-{(R)-2-[N'-(3-methoxy-phenyl)-hydrazinocarbonyl]-heptyl}-formamide.
N-Hydroxy-N-{(R)-2-[N'-(4-trifluoromethyl-pyrimidin-2-yl)-hydrazinocarbonyl]-heptyl}-formamide.
N-{(R)-2-[N'-(4-Cyano-phenyl)-hydrazinocarbonyl]-heptyl}-N-hydroxy-formamide.
N-{(R)-2-[N'-(2,6-Dimethyl-pyrimidin-4-yl)-hydrazinocarbonyl]-heptyl}-N-hydroxy-formamide.
N-Hydroxy-N-[(R)-2-(N'-quinoxalin-2-yl-hydrazinocarbonyl)-heptyl]-formamide.
N-Hydroxy-N-((2R)-2-{N'-(3,4-dihydro-quinoxalin-2-yl)-hydrazinocarbonyl}-heptyl)-formamide.
N-Hydroxy-N-{(R)-2-[N'-(1,3,4-trimethyl-1H-pyrazolo[3,4-b]pyridin-6-yl)-hydrazinocarbonyl]-heptyl}-formamide.
4-(N'-{(R)-2-[(Formyl-hydroxy-amino)-methyl]-heptanoyl}-hydrazino)-benzenesulfonamide.
N-Hydroxy-N-[(2R)-2-(cyclohexylmethyl)-3-oxo-3-{N'-[4-(trifluoromethyl)-pyrimidin-2-yl]-hydrazino}-propyl]-formamide.
N-Hydroxy-N-[(2R)-2-(cyclopentylmethyl)-3-oxo-3-{N'-[4-(trifluoromethyl)-pyrimidin-2-yl]-hydrazino}-propyl]-formamide.
N-{(R)-2-[N'-(Dimethyl-trifluoromethyl-pyrimidin-4-yl)-hydrazinocarbonyl]-heptyl}-N-hydroxy-formamide.
N-Hydroxy-N-{(R)-2-[N'-(6-trifluoromethyl-pyridazin-3-yl)-hydrazinocarbonyl]-heptyl}-formamide.
N-Hydroxy-N-{(R)-2-[N'-(6-trifluoromethyl-pyrimidin-4-yl)-hydrazinocarbonyl]-heptyl}-formamide.
N-Hydroxy-N-{(R)-2-[N'-(5-methyl-[1,2,4]triazolo[1,5-a]pyrimidin-7-yl)-hydrazinocarbonyl]-heptyl}-formamide.
N-Hydroxy-N-{(R)-2-[N'-(9H-purin-6-yl)-hydrazinocarbonyl]-heptyl}-formamide.
N-{(R)-2-[N'-(5-Cyano-pyrimidin-2-yl)-hydrazinocarbonyl]-heptyl}-N-hydroxy-formamide.
N-Hydroxy-N-((2R)-2-{[N'-(pyrimidin-2-yl)-hydrazino]carbonyl}-heptyl)-formamide.
N-Hydroxy-N-((2R)-2-(cyclobutylmethyl)-3-oxo-3-{N'-[4-(trifluoromethyl)-pyrimidin-2-yl]-hydrazino}-propyl)-formamide.
N-Hydroxy-N-{(R)-2-[N'-(6-imidazol-1-yl-pyrimidin-4-yl)-hydrazinocarbonyl]-heptyl}-formamide.
N-[(R)-2-(N'-Benzo[1,2,4]triazin-3-yl-hydrazinocarbonyl)-heptyl]-N-hydroxy-formamide.
N-Hydroxy-N-{(R)-2-[N'-(7-methoxy-benzo[1,2,4]triazin-3-yl)-hydrazinocarbonyl]-heptyl}-formamide.
N-Hydroxy-N-{(R)-2-[N'-(1-methyl-1H-pyrazolo[3,4-d]pyrimidin-6-yl)-hydrazinocarbonyl]-heptyl}-formamide.
N-((R)-2-{N'-[6-(5-Chloro-pyridin-3-yl-oxy)-pyridazin-3-yl]-hydrazinocarbonyl}-heptyl)-N-hydroxy-formamide.
N-Hydroxy-N-[(2R)-2-({N'-[6-(1H-pyrrol-1-yl)-3-pyridazinyl]-hydrazino}-carbonyl)-heptyl]-formamide.
N-Hydroxy-N-((2R)-2-{[N'-(9-methyl-9H-purin-6-yl)-hydrazino]-carbonyl}-heptyl)-formamide.
N-Hydroxy-N-{(R)-2-[N-({6-morpholin-4-yl}-9H-purin-2-yl)-hydrazinocarbonyl]-heptyl}-formamide.
N-{(R)-2-[N'-(6-Fluoro-pyridin-2-yl)-hydrazinocarbonyl]-heptyl}-N-hydroxy-formamide.
N-Hydroxy-N-((2R)-2-{[N'-(1-methyl-1H-pyrazolo[3,4-d]pyrimidin-4-yl)-hydrazino]-carbonyl}-heptyl)-formamide.
N-{(R)-2-[N'-(4-Amino-6-isopropyl-[1,3,5]triazin-2-yl)-hydrazinocarbonyl]-heptyl}-N-hydroxy-formamide.
N-{(R)-2-[N'-(2,5-Dimethyl-4-nitro-2H-pyrazol-3-yl)-hydrazinocarbonyl]-heptyl}-N-hydroxy-formamide.
N-{(R)-2-[N'-(3-Chloro-1-methyl-1H-pyrazolo[3,4-d]pyrimidin-6-yl)-hydrazinocarbonyl]-heptyl}-N-hydroxy-formamide.
N-{(R)-2-[N'-(6-Dimethylamino-9H-purin-2-yl)-hydrazinocarbonyl]-heptyl}-N-hydroxy-formamide.
N-Hydroxy-N-[(2R)-4-cyclopropyl-2-({N'-[4-(trifluoromethyl)-pyrimidin-2-yl]-hydrazino}-carbonyl)-butyl]-formamide.
N-Hydroxy-N-((2R)-2-(cyclopropylmethyl)-3-oxo-3-{N'-[4-(trifluoromethyl)-pyrimidin-2-yl]-hydrazino}-propyl)-formamide.
N-Hydroxy-N-{(R)-2-[N'-methyl-N'-(4-trifluoromethyl-pyrimidin-2-yl)-hydrazinocarbonyl]-heptyl}-formamide.
2-(N'-{(R)-2-[(Formyl-hydroxy-amino)-methyl]-heptanoyl}-hydrazino)-4-trifluoromethyl-pyrimidine-5-carboxylic acid methyl ester.
2-(N'-{(R)-2-[(Formyl-hydroxy-amino)-methyl]-heptanoyl}-hydrazino)-4-trifluoromethyl-pyrimidine-5-carboxylic acid.
N-{(R)-2-[N'-(5-Fluoro-4-methoxy-pyrimidin-2-yl)-hydrazinocarbonyl]-heptyl}-N-hydroxy-formamide.
N-{(R)-2-[N'-(4-Dimethylamino-pyrimidin-2-yl)-hydrazinocarbonyl]-heptyl}-N-hydroxy-formamide.
N-Hydroxy-N-{(2R)-2-[(N'-{6-[(2-hydroxyethyl)amino]-1,3-dihydro-2H-purin-2-ylidene}-hydrazino)-carbonyl]-heptyl}-formamide.
N-{(R)-2-[N'-(5-Fluoro-4-morpholin-4-yl-pyrimridin-2-yl)-hydrazinocarbonyl]-heptyl}-N-hydroxy-formamide.

N-{(R)-2-[N'-(5-Fluoro-4-methylamino-pyrimidin-2-yl)-hydrazinocarbonyl]-heptyl}-N-hydroxy-formamide.
2-(N'-{(R)-2-[(Formyl-hydroxy-amino)-methyl]-heptanoyl}-hydrazino)-4-trifluoromethyl-pyrimidine-5-carboxylic acid dimethylamide.
N-Hydroxy-N-{(R)-2-[N'-(3-oxo-3,4-dihydro-quinoxalin-2-yl)-hydrazinocarbonyl]-heptyl}-formamide.
N-{(R)-2-Butoxy-2-[N'-(4-trifluoromethyl-pyrimidin-2-yl)-hydrazinocarbonyl]-ethyl}-N-hydroxy-formamide.
2-(N'-{(R)-2-[(Formyl-hydroxy-amino)-methyl]-heptanoyl}-hydrazino)-4-trifluoromethyl-pyrimidine-5-carboxylic acid (2-fluoro-phenyl)-amide.
2-(N'-{(R)-2-[(Formyl-hydroxy-amino)-methyl]-heptanoyl}-hydrazino)-4-trifluoromethyl-pyrimidine-5-carboxylic acid tert-butylamide.
N-Hydroxy-N-((R)-2-{N'-[(1-piperidin-1-yl-methanoyl)-trifluoromethyl-pyrimidin-2-yl]-hydrazinocarbonyl}-heptyl)-formamide.
N-{(R)-2-[N'-(5-Cyano-4-trifluoromethyl-pyrimidin-2-yl)-hydrazinocarbonyl]-heptyl}-N-hydroxy-formamide.
N-Hydroxy-N-[(2R)-2-({N'-[9-(4,4,4-trifluorobutyl)-1,9-dihydro-2H-purin-2-ylidene]-hydrazino}-carbonyl)-heptyl]-formamide.
N-Hydroxy-N-((R)-2-{N'-[(1-morpholin-4-yl-methanoyl)-trifluoromethyl-pyrimidin-2-yl]-hydrazinocarbonyl}-heptyl)-formamide.
2-(N'-{(R)-2-[(Formyl-hydroxy-amino)-methyl]-heptanoyl}-hydrazino)-4-trifluoromethyl-pyrimidine-5-carboxylic acid benzylamide.
N-Hydroxy-N-[(2R)-3-[N'-(1,2,4-benzotriazin-3-yl)-hydrazino]-2-(cyclohexylmethyl)-3-oxopropyl]-formamide.
N-Hydroxy-N-((2R)-2-(cyclohexylmethyl)-3-{N'-[7-(methyloxy)-1,2,4-benzotriazin-3-yl]-hydrazino}-3-oxopropyl)-formamide.
2-[2-((2R)-2-{[Formyl(hydroxy)amino]methyl}heptanoyl)hydrazino]-N-methyl-N-2-pyridinyl-4-(trifluoromethyl)-5-pyrimidinecarboxamide.
2-[2-((2R)-2-{[Formyl(hydroxy)amino]methyl}heptanoyl)hydrazino]-N-methyl-N-phenyl-4-(trifluoromethyl)-5-pyrimidinecarboxamide.
2-(N'-{(R)-2-[(Formyl-hydroxy-amino)-methyl]-heptanoyl}-hydrazino)-4-trifluoromethyl-pyrimidine-5-carboxylic acid morpholin-4-ylamide.
N-Hydroxy-N-((R)-2-{N'-[(N'-phenyl-hydrazinocarbonyl)-trifluoromethyl-pyrimidin-2-yl]-hydrazinocarbonyl}-heptyl)-formamide.
2-(N'-{(R)-2-[(Formyl-hydroxy-amino)-methyl]-heptanoyl}-hydrazino)-4-trifluoromethyl-pyrimidine-5-carboxylic acid piperidin-1-ylamide.
2-(N'-{(R)-2-[(Formyl-hydroxy-amino)-methyl]-heptanoyl}-hydrazino)-4-trifluoromethyl-pyrimidine-5-carboxylic acid pyrrol-1-ylamide.
N-{(R)-2-[N'-(Dimethylamino-fluoro-pyrimidin-2-yl)-hydrazinocarbonyl]-heptyl}-N-hydroxy-formamide.
N-((R)-2-{N'-[(Ethyl-methyl-amino)-fluoro-pyrimidin-2-yl]-hydrazinocarbonyl}-heptyl)-N-hydroxy-formamide.
N-Hydroxy-N-((2R)-2-(cyclopentylmethyl)-3-{N'-[7-(methyloxy)-1,2,4-benzotriazin-3-yl]-hydrazino}-3-oxopropyl)-formamide.
N-Hydroxy-N-{(R)-2-[N'-(1-methyl-1H-benzoimidazol-2-yl)-hydrazinocarbonyl]-heptyl}-formamide.
N-{(R)-2-[N'-(4-Azetidin-1-yl-5-fluoro-pyrimidin-2-yl)-hydrazinocarbonyl]heptyl}-N-hydroxy-formamide.
N-{(R)-2-[N'-(4-Cyclopropylanino-5-fluoro-pyrimidin-2-yl)-hydrazinocarbonyl]-heptyl}-N-hydroxy-formamide.
N-[(R)-2-(N-Benzo[1,2,4]triazin-3-yl-hydrazinocarbonyl)-3-cyclopentyl-propyl]-N-hydroxy-formamide.
N-Hydroxy-N-{(R)-2-[N'-(morpholin-4-yl-trifluoromethyl-pyrimidin-2-yl)-hydrazinocarbonyl]-heptyl}-formamide.
N-Hydroxy-N-[(R)-2-(N'-{[(2-hydroxy-ethyl)-methyl-amino]-trifluoromethyl-pyrimidin-2-yl}-hydrazinocarbonyl)-heptyl]-formamide.
N-Hydroxy-N-((R)-2-{N'-[(4-methyl-piperazin-1-yl)-trifluoromethyl-pyrimidin-2-yl]-hydrazinocarbonyl}-heptyl)-formamide.
N-Hydroxy-N-((2R)-2-(cyclohexylmethyl)-3-{N'-[4-(cyclopropylamino)-5-fluoro-pyrimidin-2-yl]hydrazino}-3-oxopropyl)-formamide.
N-Hydroxy-N-((2R)-2-(cyclopentylmethyl)-3-{N'-[4-(cyclopropylamino)-5-fluoro-pyrimidin-2-yl]hydrazino}-3-oxopropyl)-formamide.
N-Hydroxy-N-[(2R)-3-{N'-[4-(azetidin-1-yl)-5-fluoro-pyrimidin-2-yl]-hydrazino}-2-(cyclopentylmethyl)-3-oxopropyl]-formamide.
N-Hydroxy-N-[(2R)-5-methyl-2-({N'-[4-(trifluoromethyl)-pyrimidin-2-yl]-hydrazino}-carbonyl)-hexyl]-formamide.
N-[(R)-2-(N'-Benzo[1,2,4]triazin-3-yl-hydrazinocarbonyl)-5-methyl-hexyl]-N-hydroxy-formamide.
N-Hydroxy-N-[(2R)-5-methyl-2-({N'-[7-(methyloxy)-1,2,4-benzotriazin-3-yl]-hydrazino}-carbonyl)-hexyl]-formamide.
N-{(R)-2-[N'-(7-Chloro-benzo[1,2,4]triazin-3-yl)-hydrazinocarbonyl]-heptyl}-N-hydroxy-formamide.
N-Hydroxy-N-((2R)-2-(cyclopentylmethyl)-3-{N'-[4-(morpholin-4-yl)-6-(trifluoromethyl)-pyrimidin-2-yl]-hydrazino}-3-oxopropyl)-formamide.
N-Hydroxy-N-((2R)-2-(cyclopentylmethyl)-3{N'-[4-[(2-hydroxyethyl)-(methyl)-amino]-6-(trifluoromethyl)-pyrimidin-2-yl]-hydrazino}-3-oxopropyl)-formamide.
N-Hydroxy-N-[(2R)-6-methyl-2-({N'-[4-(trifluoromethyl)-pyrimidin-2-yl]-hydrazino}-carbonyl)-heptyl]-formamide.
N-Hydroxy-N-((2R)-2-{[N'-(1,2,4-benzotriazin-3-yl)-hydrazino]carbonyl}-6-methylheptyl)-formamide.
N-Hydroxy-N-{(R)-2-[N'-(5-methyl-benzo[1,2,4]triazin-3-yl)-hydrazinocarbonyl]-heptyl}-formamide.
N-((R)-2-{N'-[(4-Ethyl-piperazin-1-yl)-trifluoromethyl-pyrimidin-2-yl]-hydrazinocarbonyl}-heptyl)-N-hydroxy-formamide.
N-Hydroxy-N-{(R)-2-[N'-(piperazin-1-yl-trifluoromethyl-pyrimidin-2-yl)-hydrazinocarbonyl]-heptyl}-formamide.
N-{(R)-2-[N'-(7-Fluoro-benzo[1,2,4]triazin-3-yl)-hydrazinocarbonyl]-heptyl}-N-hydroxy-formamide.
N-Hydroxy-N-[(2R)-2-({N'-[4-(4-ethyl-1-piperazinyl)-6-(trifluoromethyl)-pyrimidin-2-yl]-hydrazino}-carbonyl)-6-methylheptyl]-formamide.
N-Hydroxy-N-[(2R)-6-methyl-2-({N'-[4-(piperazin-1-yl)-6-(trifluoromethyl)-pyrimidin-2-yl]-hydrazino}-carbonyl)-heptyl]-formamide.
N-Hydroxy-N-[(2R)-6-methyl-2-({N'-[4-(4-methyl-piperazin-1-yl)-6-(trifluoromethyl)-pyrimidin-2-yl]-hydrazino}-carbonyl)-heptyl]-formamide.
N-Hydroxy-N-((2R)-2-{[N'-(7-chloro-1,2,4-benzotriazin-3-yl)hydrazino]carbonyl}-6-methylheptyl)-formamide.
N-Hydroxy-N-((2R)-6-methyl-2-{([N'-(5-methyl-1,2,4-benzotriazin-3-yl)-hydrazino]-carbonyl}-heptyl)-formamide.
N-Hydroxy-N-((2R)-2-{[N'-(7-fluoro-1,2,4-benzotriazin-3-yl)-hydrazino]-carbonyl}-6-methylheptyl)-formamide.
N-Hydroxy-N-((R)-2-{N'-[(2-methoxy-ethylamino)-trifluoromethyl-pyrimidin-2-yl]-hydrazinocarbonyl}-heptyl)-formamide.

N-Hydroxy-N-[(2R)-6-methyl-2-({N'-[7-(methyloxy)-1,2,4-benzotriazin-3-yl]-hydrazino}-carbonyl)-heptyl]-formamide.

N-Hydroxy-N-[(R)-2-(N'-{[4-(2-hydroxy-ethyl)-piperazin-1-yl]-trifluoromethyl-pyrimidin-2-yl}-hydrazinocarbonyl)-heptyl]-formamide.

N-Hydroxy-N-((R)-2-{N'-[(4-pyrimidin-2-yl-piperazin-1-yl)-trifluoromethyl-pyrimidin-2-yl]-hydrazinocarbonyl}-heptyl)-formamide.

N-Hydroxy-N-((R)-2-{N'-[(2-hydroxy-ethylamino)-trifluoromethyl-pyrimidin-2-yl]-hydrazinocarbonyl}-heptyl)-formamide.

N-Hydroxy-N-{(R)-2-[N'-(7-trifluoromethyl-benzo[1,2,4]triazin-3-yl)-hydrazinocarbonyl]-heptyl}-formamide.

N-Hydroxy-N-{(R)-2-[N'-(6-methyl-benzo[1,2,4]triazin-3-yl)-hydrazinocarbonyl]-heptyl}-formamide.

N-Hydroxy-N-{(2R)-2-(cyclopentylmethyl)-3-[N'-(5-methyl-1,2,4-benzotriazin-3-yl)hydrazino]-3-oxopropyl}-formamide.

N-Hydroxy-N-[(2R)-2-({N'-[4-(trifluoromethyl)-pyrimidin-2-yl]-hydrazino}-carbonyl)-octyl]-formamide.

N-Hydroxy-N-((2R)-2-{[N'-(1,2,4-benzotriazin-3-yl)hydrazino]-carbonyl}-octyl)-formamide.

N-Hydroxy-N-[(2R)-2-({N'-[7-(methyloxy)-1,2,4-benzotriazin-3-yl]-hydrazino}-carbonyl)-octyl]-formamide.

N-Hydroxy-N-{(R)-2-[N'-(7-methyl-benzo[1,2,4]triazin-3-yl)-hydrazinocarbonyl]-heptyl}-formamide.

N-{(R)-2-[N'-(6-Chloro-benzo[1,2,4]triazin-3-yl)-hydrazinocarbonyl]-heptyl}-N-hydroxy-formamide.

N-Hydroxy-N-{(R)-2-[N'-(5-methoxy-benzo[1,2,4]triazin-3-yl)-hydrazinocarbonyl]-heptyl}-formamide.

N-Hydroxy-N-{(R)-2-[N'-(1-methyl-2-oxo-1,2-dihydro-pyridin-4-yl)-hydrazinocarbonyl]-heptyl}-formamide.

N-Hydroxy-N-((R)-2-{N'-[(N'-pyridin-2-yl-hydrazino)-trifluoromethyl-pyrimidin-2-yl]-hydrazinocarbonyl}-heptyl)-formamide.

N-Hydroxy-N-{(R)-2-[N'-(4-methyl-6-morpholin-4-yl-pyrimidin-2-yl)-hydrazinocarbonyl]-heptyl}-formamide.

N-((R)-2-{N'-[4-(4-Ethyl-piperazin-1-yl)-6-methyl-pyrimidin-2-yl]-hydrazinocarbonyl}-heptyl)-N-hydroxy-formamide.

N-{(R)-2-[N'-(4,6-Dimethyl-pyrimidin-2-yl)-hydrazinocarbonyl]-heptyl}-N-hydroxy-formamide.

N-Hydroxy-N-{(R)-2-[N'-(4-trifluoromethyl-pyrimidin-2-yl)-hydrazinocarbonyl]-heptyl}-formamide.

N-Hydroxy-N-[(R)-2-(N'-isoquinolin-1-yl-hydrazinocarbonyl)-heptyl]-formamide.

N-Hydroxy-N-[(R)-2-(N'-quinolin-2-yl-hydrazinocarbonyl)-heptyl]-formamide.

N-{(R)-2-[N'-(1-Benzyl-2-oxo-1,2-dihydro-pyridin-4-yl)-hydrazinocarbonyl]-heptyl}-N-hydroxy-formamide.

N-Hydroxy-N-{(R)-2-[N'-(4-oxo-4H-pyrido[1,2-a][1,3,5]triazin-2-yl)-hydrazinocarbonyl]-heptyl}-formamide.

N-Hydroxy-N-{(R)-2-[N'-(4-methyl-pyrimidin-2-yl)-hydrazinocarbonyl]-heptyl}-formamide.

N-{(R)-2-[N'-(1-Butyl-2-oxo-1,2-dihydro-pyridin-4-yl)-hydrazinocarbonyl]-heptyl}-N-hydroxy-formamide.

N-Hydroxy-N-{(R)-2-[N'-(9-methyl-4-oxo-4H-pyrido[1,2-a][1,3,5]triazin-2-yl)-hydrazinocarbonyl]-heptyl}-formamide.

N-Hydroxy-N-{(R)-2-[N'-(6-oxo-4-trifluoromethyl-1,6-dihydro-pyrimidin-2-yl)-hydrazinocarbonyl]-heptyl}-formamide.

N-Hydroxy-N-{(R)-2-[N'-(methyl-trifluoromethyl-pyrimidin-2-yl)-hydrazinocarbonyl]-heptyl}-formamide.

N-Hydroxy-N-{(R)-2-[N'-(5-trifluoromethyl-pyridin-2-yl)-hydrazinocarbonyl]-heptyl}-formamide.

N-{(R)-2-[N'-(6-Ethoxy-pyridin-2-yl)-hydrazinocarbonyl]-heptyl}-N-hydroxy-formamide.

N-Hydroxy-N-[(R)-2-(N'-pyrido[2,3-e]-[1,2,4]triazin-3-yl-hydrazinocarbonyl)-heptyl]-formamide.

N-((R)-2-{N'-[1-(1-Ethyl-propyl)-2-oxo-1,2-dihydro-pyridin-4-yl]-hydrazinocarbonyl}-heptyl)-N-hydroxy-formamide.

N-Hydroxy-N-((R)-2-{N'-[2-oxo-1-(3-trifluoromethyl-benzyl)-1,2-dihydro-pyridin-4-yl]-hydrazinocarbonyl}-heptyl)-formamide.

N-Hydroxy-N-{(R)-2-[N'-(4-methyl-pyridin-2-yl)-hydrazinocarbonyl]-heptyl}-formamide.

N-Hydroxy-N-{(R)-2-[N'-(6-methoxy-pyridin-2-yl)-hydrazinocarbonyl]-heptyl}-formamide.

N-Hydroxy-N-{(R)-2-[N'-(2-oxo-1-quinolin-8-yl-methyl-1,2-dihydro-pyridin-4-yl)-hydrazinocarbonyl]-heptyl}-formamide.

N-Hydroxy-N-[(R)-2-(N'-{2-oxo-1-[2-(5,6,7,8-tetrahydro-[1,8]naphthyridin-2-yl)-ethyl]-dihydro-pyridin-4-yl}-hydrazinocarbonyl)-heptyl]-formamide.

N-{(R)-2-[N'-(4,6-Bis-ethylamino-[1,3,5]triazin-2-yl)-hydrazinocarbonyl]-heptyl}-N-hydroxy-formamide.

N-{(R)-2-[N'-(Bis-dimethylamino-[1,3,5]triazin-2-yl)-hydrazinocarbonyl]-heptyl}-N-hydroxy-formamide.

N-{(R)-2-[N'-(4,6-Di-morpholin-4-yl-[1,3,5]triazin-2-yl)-hydrazinocarbonyl]-heptyl}-N-hydroxy-formamide.

N-Hydroxy-N-((R)-2{N'-[4-(4-methyl-piperazin-1-yl)-6-propylamino-[1,3,5]triazin-2-yl]-hydrazinocarbonyl}-heptyl)-formamide.

N-{(R)-2-[N'-(Dimethylamino-morpholin-4-yl-[1,3,5]triazin-2-yl)-hydrazinocarbonyl]-heptyl}-N-hydroxy-formamide.

N-Hydroxy-N-{(R)-2-[N'-(6-methyl-pyridin-2-yl)-hydrazinocarbonyl]-heptyl}-formamide.

N-Hydroxy-N-((R)-2-{N'-[5-(5-phenyl-[1,3,4]oxadiazol-2-yl)-pyridin-2-yl]-hydrazinocarbonyl}-heptyl)-formamide.

N-{(R)-2-[N'-(7-tert-Butyl-1,4-dioxo-1,2,3,4-tetrahydro-pyrido[3,4-d]pyridazin-5-yl)-hydrazinocarbonyl]-heptyl}-N-hydroxy-formamide.

N-((R)-2-{N'-[4-Ethylamino-6-(4-methyl-[1,4]diazepan-1-yl)-[1,3,5]triazin-2-yl]-hydrazinocarbonyl}-heptyl)-N-hydroxy-formamide.

N-((R)-2-{N'-[4-Ethylamino-6-(4-ethyl-piperazin-1-yl)-[1,3,5]triazin-2-yl]-hydrazinocarbonyl}-heptyl)-N-hydroxy-formamide.

N-Hydroxy-N-{(R)-2-[N'-(6-trifluoromethyl-pyridin-2-yl)-hydrazinocarbonyl]-heptyl}-formamide.

N-Hydroxy-N-{(R)-2-[N'-(4-methyl-6-morpholin-4-yl-methyl-pyrimidin-2-yl)-hydrazinocarbonyl]-heptyl}-formamide.

N-Hydroxy-N-{(R)-2-[N'-(4-methyl-6-morpholin-4-yl-[1,3,5]triazin-2-yl)-hydrazinocarbonyl]-heptyl}-formamide.

N-Hydroxy-N-{(2R)-2-(cyclopentylmethyl)-3-[N'-(4,6-dimethyl-2-pyrimidinyl)-hydrazino]-3-oxopropyl}-formamide.

N-Hydroxy-N-{(R)-2-[N'-(4-methyl-6-pyrrolidin-1-yl-methyl-pyrimidin-2-yl)-hydrazinocarbonyl]-heptyl}-formamide.

N-{(R)-2-[N'-(4-Dimethylaminomethyl-6-methyl-pyrimidin-2-yl)-hydrazinocarbonyl]-heptyl}-N-hydroxy-formamide.

N-((R)-2-{N'-[4-methyl-6-(4-methyl-piperazin-1-yl-methyl)-pyrimidin-2-yl]-hydrazinocarbonyl}-heptyl)-formamide.

N-Hydroxy-N-{(R)-2-[N'-(5-methyl-pyridin-2-yl)-hydrazinocarbonyl]-heptyl}-formamide.

N-((R)-2-{N'-[Dimethylamino-(4-methyl-[1,4]diazepan-1-yl)-[1,3,5]triazin-2-yl]-hydrazinocarbonyl}-heptyl)-N-hydroxy-formamide.
N-Hydroxy-N-{(R)-2-[N'-(4-methyl-6-pyrrolidin-1-yl-[1,3,5]triazin-2-yl)-hydrazinocarbonyl]-heptyl}-formamide.
N-Hydroxy-N-((R)-2{N'-[4-methyl-6-)4-pyrrolidin-1-yl-piperidin-1-yl)-[1,3,5]triazin-2-yl]-hydrazinocarbonyl}-heptyl)-formamide.
N-((R)-2-{N'[(Ethyl-methyl-amino)-methyl-[1,3,5]triazin-2-yl]-hydrazinocarbonyl}-heptyl)-N-hydroxy-formamide.
N-((R)-2-{N'-[(4-(4-Ethyl-piperazin-1-yl)-6-methyl-[1,3,5]triazin-2-yl]-hydrazinocarbonyl}-heptyl)-N-hydroxy-formamide.
N-Hydroxy-N-[(2R)-7,7,7-trifluoro-2-({N'-[4-(trifluoromethyl)-pyrimidin-2-yl]-hydrazino}-carbonyl)-heptyl]-formamide.
N-Hydroxy-N-((2R)-7,7,7-trifluoro-2-{[N'-(5-methyl-1,2,4-benzotriazin-3-yl)-hydrazino]-carbonyl}-heptyl)-formamide.
N-Hydroxy-N-((2R)-7,7,7-trifluoro-2-{[N'-(7-methyl-1,2,4-benzotriazin-3-yl)-hydrazino]-carbonyl}-heptyl)formamide.
N-Hydroxy-N-{(R)-2-[N'-(4-methylamino-6-morpholin-4-yl-[1,3,5]-2-yl)-hydrazinocarbonyl]-heptyl}-formamide.
N-((R)-2-{N'-[4-(4-Ethyl-piperazin-1-yl)-6-methylamino-[1,3,5]triazin-2-yl]-hydrazinocarbonyl}-heptyl)-N-hydroxy-formamide.
N-{(R)-2-[N'-(4-Ethylamino-6-morpholinyl-4-yl-[1,3,5]triazin-2-yl)-hydrazinocarbonyl]-heptyl}-N-hydroxy-formamide.
N-Hydroxy-N-{(R)-2-[N'-(4,6,7-trimethyl-7,8-dihydropterin-2-yl)-hydrazinocarbonyl]-heptyl}-formamide.
N-Hydroxy-N-{(R)-2-N'-(4,6,7-trimethyl-pteridin-2-yl)-hydrazinocarbonyl]-heptyl}-formamide.
N-Hydroxy-N-{(R)-2-[N'-(methoxymethoxymethyl-trifluoromethyl-pyrimidin-2-yl)-hydrazinocarbonyl]-heptyl}-formamide.
N-Hydroxy-N-((R)-2-{N'-[4-methyl-6-(1-piperidin-1-yl-methanoyl)-pyrimidin-2-yl]-hydrazinocarbonyl}-heptyl)-formamide.
2-(N'-{(R)-2-[(Formyl-hydroxy-amino)-methyl]-heptanoyl}-hydrazino)-6-methyl-pyrimidine-4-carboxylic acid cyclopropylamide.
2-(N'-{(R)-2-[(Formyl-hydroxy-amino)-methyl]-heptanoyl}-hydrazino)-6-methyl-pyrimidine-4-carboxylic acid diisopropylamide.
N-{(R)-2-[N'-(5-Cyano-pyridin-2-yl)-hydrazinocarbonyl]-heptyl}-N-hydroxy-formamide.
N-{(R)-2-[N'-(4,6-Diethyl-[1,3,5]triazin-2-yl)-hydrazinocarbonyl]-heptyl}-N-hydroxy-formamide.
N-{(R)-4-Cyclopentyl-2-[N'-(4-trifluoromethyl-pyrimidin-2-yl)-hydrazinocarbonyl]-butyl}-N-hydroxy-formamide.
N-{(R)-4-Cyclopentyl-2-[N'-(7-methyl-benzo[1,2,4]triazin-3-yl)-hydrazinocarbonyl]-butyl}-N-hydroxy-formamide.
N-{(R)-4Cyclopentyl-2-[N'-(5-methyl-benzo[1,2,4]triazin-3-yl)-hydrazinocarbonyl]-butyl}-N-hydroxy-formamide.
N-Hydroxy-N-((R)-2-N'-[6-(4-methyl-piperazin-1-yl-methyl)-pyridin-2-yl]-hydrazinocarbonyl}-heptyl)-formamide.
N-((R)-2-{N'-[5-(4,6-Dimethoxy-pyrimidin-2-yl)-pyridin-2-yl]-hydrazinocarbonyl}-heptyl)-N-hydroxy-formamide.
N-{(R)-2-[N'-(Diethylamino-methyl-[1,3,5]triazin-2-yl)-hydrazinocarbonyl]-heptyl}-N-hydroxy-formamide.
N-Hydroxy-N-[(R)-2-(N'-{[(2-methoxy-ethyl)-methyl-amino]-methyl-[1,3,5]triazin-2-yl}-hydrazinocarbonyl)-heptyl]-formamide.
N-((R)-1-{N'-[4-(2,6-Dimethyl-morpholin-4-yl)-6-methyl-[1,3,5]triazin-2-yl]-hydrazinocarbonyl}-heptyl)-N-hydroxy-formamide.
N-{(R)-2-[N'-(5-Fluoro-4-methyl-6-morpholin-4-yl-pyrimidin-2-yl)-hydrazinocarbonyl]-heptyl)-N-hydroxy-formamide.
N-{(R)-2-[N'-(4-Ethyl-6-morpholin-4-yl-[1,3,5]triazin-2-yl)-hydrazinocarbonyl]-heptyl}-N-hydroxy-formamide.
N-{(R)-2-[N'-Ethyl-methyl-amino)-[1,3,5]triazin-2-yl)-hydrazinocarbonyl]-heptyl}-N-hydroxy-formamide.
N-((R)-2-{N'-[4-Ethyl-6-(4-ethyl-piperazin-1-yl)-[1,3,5]triazin-2-yl]-hydrazinocarbonyl}-heptyl)-N-hydroxy-formamide.
N-((R)-2-{N'-[5-Fluoro-4-methyl-6-(4-methyl-piperazin-1-yl)-pyrimidin-2-yl]-hydrazinocarbonyl}-heptyl)-N-hydroxy-formamide.
N-{(R)-2-[N'-(Dimethylamino-ethyl-[1,3,5]triazin-2-yl)-hydrazinocarbonyl]-heptyl}-N-hydroxy-formamide.
N-((R)-2-{N'-[5-Fluoro-4-methyl-6-(4-methyl-[1,4]diazepan-1-yl)-pyrimidin-2-yl]-hydrazinocarbonyl}-heptyl)-N-hydroxy-formamide.
N-{(R)-4-Cyclopentyl-2-[N'-(morpholin-4-yl-trifluoromethyl-pyrimidin-2-yl)-hydrazinocarbonyl]-butyl}-N-hydroxy-formamide.
N-[(R)-2-(N'-{Ethyl-[(2-methoxy-ethyl)-methyl-amino]-[1,3,5]triazin-2-yl}-hydrazinocarbonyl)-heptyl]-N-hydroxy-formamide.
N-{(R)-2-[N'-(Dimethylamino-methyl-pyrimidin-2-yl)-hydrazinocarbonyl]-heptyl}-N-hydroxy-formamide.
N-{(R)-2-[N'-(4-Cyclopropylamino-6-methyl-pyrimidin-2-yl)-hydrazinocarbonyl]-heptyl}-N-hydroxy-formamide.
N-{(R)-2-Cyclohexyl-2-[N'-(4-trifluoromethyl-pyrimidin-2-yl)-hydrazinocarbonyl]-ethyl}-N-hydroxy-formamide.
N-{(R)-2-Cyclohexyl-2-[N'-(7-methoxy-benzo[1,2,4]triazin-3-yl)-hydrazinocarbonyl]-ethyl}-N-hydroxy-formamide.
N-{(R)-2-Cyclohexyl-2-[N'-(5-methyl-benzo[1,2,4]triazin-3-yl)-hydrazinocarbonyl]-ethyl}-N-hydroxy-formamide.
N-{(R)-4,4-Dimethyl-2-[N'-(4-trifluoromethyl-pyrimidin-2-yl)-hydrazinocarbonyl]-pentyl}-N-hydroxy-formamide.
N-{(R)-4,4-Dimethyl-2-[N'-(7-methyl-benzo[1,2,4]triazin-3-yl)-hydrazinocarbonyl]-pentyl}-N-hydroxy-formamide.
N-{(R)-4,4-Dimethyl-2-[N'-(5-methyl-benzo[1,2,4]triazin-3-yl)-hydrazinocarbonyl]-pentyl}N-hydroxy-formamide.
N-{(R)-4,4-Dimethyl-2-[N'-(morpholin-4-yl-trifluoromethyl-pyrimidin-2-yl)-hydrazinocarbonyl]-pentyl}-N-hydroxy-formamide.
N-((R)-2-{N'-[Ethyl-(methyl-pyridin-2-yl-amino)-[1,3,5]triazin-2-yl]-hydrazinocarbonyl}-heptyl)-N-hydroxy-formamide.
N-{(R)-2-[N'-(4-Cyclopropylamino-6-ethyl-[1,3,5]triazin-2-yl)-hydrazinbcarbonyl]-heptyl}-N-hydroxy-formamide.
N-Hydroxy-N-[(R)-2-[N'-(5-methyl-benzo[1,2,4]triazin-3-yl)-hydrazinocarbonyl]-3-(1-methyl-cyclopentyl)-propyl]-formamide.
N-Hydroxy-N-[(R)-2-[N'-(7-methoxy-benzo[1,2,4]triazin-3-yl)-hydrazinocarbonyl]-3-(1-methyl-cyclopentyl)-propyl]-formamide.
N-Hydroxy-N-{(R)-3-(1-methyl-cyclopentyl)-2-[N'-(4-trifluoromethyl-pyrimidin-2-yl)-hydrazinocarbonyl]-propyl}-formamide.

N-Hydroxy-N-{(R)-2-[N'-(4-isopropyl-6-morpholin-4-yl-[1,3,5]triazin-2-yl)-hydrazinocarbonyl]-heptyl}-formamide.

N-Hydroxy-N-{(2R)-2-(cyclopentylmethyl)-3-[N'-(4-methyl-2-pyrimidinyl)-hydrazino]-3-oxopropyl}-formamide.

N-Hydroxy-N-[(2R)-6,6,6-trifluoro-2-({N'-[4-(trifluoromethyl)-pyrimidin-2-yl]-hydrazino}-carbonyl)-hexyl]-formamide.

N-{(R)-2-[N'-(5,7-Dimethyl-benzo[1,2,4]triazin-3-yl)-hydrazinocarbonyl]-heptyl}-N-hydroxy-formamide.

N-{(R)-2-[N'-(3,6-Dimethyl-pyrazin-2-yl)-hydrazinocarbonyl]-heptyl}-N-hydroxy-formamide.

N-((R)-2-{N'-[4-(4-Ethyl-piperazine-1-yl)-6-isopropyl-[1,3,5]triazin-2-yl]-hydrazinocarbonyl}-heptyl)-N-hydroxy-formamide.

N-{(R)-2-[N'-(4-Dimethylamino-6-isopropyl-[1,3,5]triazin-2-yl)-hydrazinocarbonyl]-heptyl}-N-hydroxy-formamide.

N-Hydroxy-N-{(R)-2-[N'-(methyl-trifluoromethyl-pyridin-2-yl)-hydrazinocarbonyl]-heptyl}-formamide.

2-(N'-{(R)-2-[(Formyl-hydroxy-amino)-methyl]-heptanoyl}-hydrazino)-6,N,N-trimethyl-isonicotinamide.

N-Hydroxy-N[(2R)-2-({N'-[3-amino-6-(trifluoromethyl)-pyridin-2-yl]-hydrazino}-carbonyl)-heptyl]-formamide.

N-Hydroxy-N-[(R)-2-(N'-{4-isopropyl-6-[(2-methoxy-ethyl)-methyl-amino]-[1,3,5]triazin-2-yl}-hydrazinocarbonyl)-heptyl]-formamide.

N-{(R)-3-Cyclopentyl-2-[N'-(4-ethyl-6-morpholin-4-yl-[1,3,5]triazin-2-yl)-hydrazinocarbonyl]-propyl}-N-hydroxy-formamide.

N-Hydroxy-N-{(R)-2-[N'-(4-morpholin-4-yl-6-propyl-[1,3,5]triazin-2-yl)-hydrazinocarbonyl]-heptyl}-formamide.

N-((R)-2-{N'-[4-(4-Ethyl-piperazin-1-yl)-6-propyl-[1,3,5]triazin-2-yl]-hydrazinocarbonyl}-heptyl)-N-hydroxy-formamide.

N-{(R)-5,5-Dimethyl-2-[N'-(4-trifluoromethyl-pyrimidin-2-yl)-hydrazinocarbonyl]-hexyl}-N-hydroxy-formamide.

N-{(R)-5,5-Dimethyl-2-[N'-(7-methyl-benzo[1,2,4]triazin-3-yl)-hydrazinocarbonyl]-hexyl}-N-hydroxy-formamide.

N-{(R)-5,5-Dimethyl-2-[N'-(5-methyl-benzo[1,2,4]triazin-3-yl)-hydrazinocarbonyl]-hexyl}-N-hydroxy-formamide.

N-{(R)-5,5-Dimethyl-2-[N'-(morpholin-4-yl-trifluoromethyl-pyrimidin-2-yl)-hydrazinocarbonyl]-hexyl}-N-hydroxy-formamide.

N-{(R)-4-Ethyl-2-[N'-(4-trifluoromethyl-pyrimidin-2-yl)-hydrazino carbonyl]-hexyl}-N-hydroxy-formamide.

N-{(-R)-4-Ethyl-2-[N'-(7-methyl-benzo[1,2,4]triazin-3-yl)-hydrazinocarbonyl]-hexyl}-N-hydroxy-formamide.

N-{(R)-4-Ethyl-2-[N'-(morpholin-4-yl-trifluoromethyl-pyrimidin-2-yl)-hydrazinocarbonyl]-hexyl}-N-hydroxy-formamide.

N-((R)-3-Cyclopentyl-2-{N'-[4-ethyl-6-(4-ethyl-piperazin-1-yl)-[1,3,5]triazin-2-yl]-hydrazinocarbonyl}-propyl)-N-hydroxy-formamide.

N-{(R)-3-Cyclopentyl-2-[N'-(cyclopropylamino-6-ethyl-[1,3,5]triazin-2-yl)-hydrazinocarbonyl]-propyl}-N-hydroxy-formamide.

N-{(R)-4-Ethyl-2-[N'-(5-methyl-benzo[1,2,4]triazin-3-yl)-hydrazinocarbonyl]-hexyl}-N-hydroxy-formamide.

N-Hydroxy-N-[(R)-2-(N'-{[(2-methoxy-ethyl)-methyl-amino]-propyl-[1,3,5]triazin-2-yl}-hydrazinocarbonyl)-heptyl]-formamide.

N-(R)-2-[N'-(Dimethylamino-propyl-[1,3,5]triazin-2-yl)-hydrazinocarbonyl]-heptyl}-N-hydroxy-formamide.

N-{(R)-2-[N'-(4-Ethyl-pyrimidin-2-yl)-hydrazinocarbonyl]-heptyl}-N-hydroxy-formamide.

N-Hydroxy-N-{(R)-2-[N'-(4-isopropyl-pyrimidin-2-yl)-hydrazinocarbonyl]-heptyl}-formamide.

N-{(R)-2-[N'-(4-Cyclopropyl-6-morpholin-4-yl-[1,3,5]triazin-2-yl)-hydrazinocarbonyl]-heptyl}-N-hydroxy-formamide.

N-Hydroxy-N-[(2R)-2-({N'-[4-(pyridin-2-yl)-pyrimidin-2-yl]-hydrazino}-carbonyl)-heptyl]-formamide.

N-((R)-2-{N'-[4-Cyclopropyl-6-(4-ethyl-piperazin-1-yl)-[1,3,5]triazin-2-yl]-hydrazinocarbonyl}-heptyl)-N-hydroxy-formamide.

N-{(R)-2-[N'-(Cyclopropyl-dimethylamino-[1,3,5]triazin-2-yl)-hydrazinocarbonyl]-heptyl}-N-hydroxy-formamide.

N-((R)-2-{N'-[Cyclopropyl-(ethyl-methyl-amino)-[1,3,5]triazin-2-yl]-hydrazinocarbonyl}-heptyl)-N-hydroxy-formamide.

N-{(R)-2-[N'-(4-Cyclopropyl-6-pyrrolidin-1-yl[1,3,5]triazin-2-yl)-hydrazinocarbonyl]-heptyl}-N-hydroxy-formamide.

N-{(R)-2-[N'-(4,6-Dicyclopropyl-[1,3,5]triazin-2-yl)-hydrazinocarbonyl]-heptyl}-N-hydroxy-formamide.

N-Hydroxy-N-[(R)-2-[N'-(5-methyl-benzo[1,2,4]triazin-3-yl)-hydrazinocarbonyl]-3-(2-methyl-cyclopentyl)-propyl]-formamide.

N-[(R)-2-[N'-(Dimethylamino-ethyl-[1,3,5]triazin-2-yl)-hydrazinocarbonyl]-3-(2-methyl-cyclopentyl)-propyl]-N-hydroxy-formamide.

N-Hydroxy-N-[(R)-2-[N'-(4-trifluoromethyl-pyrimidin-2-yl)-hydrazinocarbonyl]-3-(2-methyl-cyclopentyl)-propyl]-formamide.

N-{(R)-2-[N'-(5-Ethyl-pyrimidin-2-yl)-hydrazinocarbonyl]-heptyl}-N-hydroxy-formamide.

N-Hydroxy-N-{(2R)-2-(cyclopentylmethyl)-3-[N'-(7-methyl-1,2,4-benzotriazin-3-yl)-hydrazino]-3-oxopropyl}-formamide.

N-Hydroxy-N-[(2R)-2-(cyclopentylmethyl)-3-('-{4-ethyl-6-[ethyl(methyl)amino]-1,3,5-triazin-2-yl}-hydrazino)-3-oxopropyl]-formamide.

N-Hydroxy-N-((2R)-2-(cyclopentylmethyl)-3-{N'-[4-(dimethylamino)-6-ethyl-1,3,5-triazin-2-yl]-hydrazino}-3-oxopropyl)-formamide.

N-((R)-2-{N'-[4-Ethyl-6-(4-isopropyl-piperazin-1-yl)-[1,3,5]triazin-2-yl]-hydrazinocarbonyl}-heptyl)-N-hydroxy-formamide.

N-Hydroxy-N-[(2R)-3-[N'-(6-chloro-1,2,4-benzotriazin-3-yl)-hydrazino]-2-(cyclopentylmethyl)-3-oxopropyl]-formamide.

N-{(R)-4,4-Dimethyl-2-[N'-(4-trifluoromethyl-pyrimidin-2-yl)-hydrazinocarbonyl]-hexyl}-N-hydroxy-formamide.

N-{(R)-4,4-Dimethyl-2-[N'-(7-methyl-benzo[1,2,4]triazin-3-yl)-hydrazinocarbonyl]-hexyl}-N-hydroxy-formamide.

N-{(R)-4,4-Dimethyl-2-[N'-(5-methyl-benzo[1,2,4]triazin-3-yl)-hydrazinocarbonyl]-hexyl}-N-hydroxy-formamide.

N-{(R)-4,4-Dimethyl-2-[N'-(morpholin-4-yl-trifluoromethyl-pyrimidin-2-yl)-hydrazinocarbonyl]-hexyl}-N-hydroxy-formamide.

N-Hydroxy-N-{(R)-2-[N'-(5-phenyl-[1,2,4]triazin-3-yl)-hydrazinocarbonyl]-heptyl}-formamide.

N-{(R)-2-[N'-(4-Ethyl-6-morpholin-4-yl-pyrimidin-2-yl)-hydrazinocarbonyl]-heptyl}-N-hydroxy-formamide.

N-((R)-2-{N'-[4-Ethyl-6-(4-methyl-piperazin-1-yl)-pyrimidin-2-yl]-hydrazinocarbonyl}-heptyl)-N-hydroxy-formamide.

N-{(R)-2-[N'-(5-Ethyl-4-methyl-pyrimidin-2-yl)-hydrazinocarbonyl]-heptyl}-N-hydroxy-formamide.

N-((R)-2-{N'-[4-Ethyl-6-(4-propyl-piperazin-1-yl)-[1,3,5]triazin-2-yl]-hydrazinocarbonyl}-heptyl)-N-hydroxy-formamide.

N-Hydroxy-N-((R)-2-{N'-[6-(4-pyrimidin-2-yl-piperazin-1-yl-methyl)-pyridin-2-yl]-hydrazinocarbonyl}-heptyl)-formamide.

N-Hydroxy-N-((R)-2-{N'-[6-(3-[1,2,4]triazol-1-yl-methyl-[1,2,4]triazol-1-yl)-pyridin-2-yl]-hydrazinocarbonyl}-heptyl)-formamide.

N-{(R)-3-Bicyclo[2.2.1]hept-7-yl-2-[N'-(4-trifluoromethyl-pyrimidin-2-yl)-hydrazinocarbonyl]-propyl}-N-hydroxy-formamide.

N-{(R)-3-Bicyclo[2.2.1]hept-7-yl-2-[N'-(morpholin-4-yl-trifluoromethyl-pyrimidin-2-yl)-hydrazinocarbonyl]-propyl}-N-hydroxy-formamide.

N-hydroxy-N-[(R)-2-(pyridin-3-yl-hydrazinocarbonyl)-heptyl]-formamide.

4-{4-Ethyl-6-[2-((2R)-2-{[formyl(hydroxy)amino]-methyl}-heptanoyl)-hydrazino]-1,3,5-triazin-2-yl}-1-methyl-1-propylpiperazin-1-ium iodide.

N-{(R)-3-Bicyclo[2.2.1]hept-7-yl-2-[N'-(5-methyl-benzo[1,2,4]triazin-3-yl)-hydrazinocarbonyl]-propyl}-N-hydroxy-formamide.

N-{(R)-2-[N'-(4-Azetidin-1-yl-6-ethyl-[1,3,5]triazin-2-yl)-hydrazinocarbonyl]-heptyl}-N-hydroxy-formamide.

N-{(R)-2-Cyclopentyl-2-[N'-(4-trifluoromethyl-pyrimidin-2-yl)-hydrazinocarbonyl]-ethyl}-N-hydroxy-formamide.

N-{(R)-2-Cyclopentyl-2-[N'-(morpholin-4-yl-trifluoromethyl-pyrimidin-2-yl)-hydrazinocarbonyl]-ethyl}-N-hydroxy-formamide.

N-{(R)-2-Cyclopentyl-2-[N'-(4-methyl-pyridin-2-yl)-hydrazinocarbonyl]-ethyl}-N-hydroxy-formamide.

N-{(R)-2-Cyclopentyl-2-[N'-(dimethylamino-ethyl-[1,3,5]triazin-2-yl)-hydrazinocarbonyl]-ethyl}-N-hydroxy-formamide.

N-{(R)-2-Cyclopentyl-2-[N'-(7-methyl-benzo[1,2,4]triazin-3-yl)-hydrazinocarbonyl]-ethyl}-N-hydroxy-formamide.

N-{(R)-2-Cyclopentyl-2-[N'-(5-methyl-benzo[1,2,4]triazin-3-yl)-hydrazinocarbonyl]-ethyl}-N-hydroxy-formamide.

N-Hydroxy-N-{(R)-2-[N'-(5-methyl-benzo[1,2,4]triazin-3-yl)-hydrazinocarbonyl]-2-(4-methyl-cyclohexyl)-ethyl}-formamide.

N-Hydroxy-N-{(R)-2-[N'-(7-methyl-benzo[1,2,4]triazin-3-yl)-hydrazinocarbonyl]-2-(4-methyl-cyclohexyl)-ethyl}-formamide.

N-Hydroxy-N-{(R)-2-(4-methyl-cyclohexyl)-2-[N'-(4-trifluoromethyl-pyrimidin-2-yl)-hydrazinocarbonyl]-ethyl}-formamide.

N-Hydroxy-N-{(R)-2-(4-methyl-cyclohexyl)-2-[N'-(morpholin-4-yl-trifluoromethyl-pyrimidin-2-yl)-hydrazinocarbonyl]-ethyl}-formamide.

N-Hydroxy-N-{(R)-2-(4-methyl-cyclohexyl)-2-[N'-(4-methyl-pyridin-2-yl)-hydrazinocarbonyl]-ethyl}-formamide.

N-{(R)-2-[N'-(Dimethylamino-ethyl-[1,3,5]triazin-2-yl)-hydrazinocarbonyl]-2-(4-methyl-cyclohexyl)-ethyl}-N-Hydroxy-formamide.

N-{(R)-2-[N'-(6,7-Dihydro-5H-cyclopentapyrimidin-2-yl)-hydrazinocarbonyl]-heptyl}-N-hydroxy-formamide.

N-((R)-2-N'-[4-Ethyl-6-((S)-2-hydroxymethyl-pyrrolidin-1-yl)-[1,3,5]triazin-2-yl]-hydrazinocarbonyl]-heptyl)-N-hydroxy-formamide.

N-{(R)-2-[N'-(Dimethylamino-pyridin-3-yl-pyrimidin-2-yl)-hydrazinocarbonyl]-heptyl}-N-hydroxy-formamide.

N-{(R)-2-[N'-(Dimethylamino-pyridin-4-yl-pyrimidin-2-yl)-hydrazinocarbonyl]-heptyl}-N-hydroxy-formamide.

N-Hydroxy-N-{(R)-2-N'-(5,6,7,8-tetrahydro-benzo[1,2,4]triazin-3-yl)-hydrazinocarbonyl]-heptyl}-formamide.

N-{(R)-2-[N'-(5,6-Diethyl-[1,2,4]triazin-3-yl)-hydrazinocarbonyl]-heptyl}-N-hydroxy-formamide.

N-Hydroxy-N-{(R)-2-[N'-[5-(4-hydroxy-phenyl)-[1,2,4]triazin-3-yl]-hydrazinocarbonyl}-heptyl)-formamide.

N-[(R)-2-(N'-{[(2-Dimethylamino-ethyl)-methyl-amino]-ethyl-[1,3,5]triazin-2-yl}-hydrazinocarbonyl)-heptyl]-N-hydroxy-formamide.

N-{(R)-2-[N'-(2-Dimethylamino-quinazolin-4-yl)-hydrazinocarbonyl]-heptyl}-N-hydroxy-formamide.

N-Hydroxy-N-{(R)-2-[N'-(3-methanesulfonyl-4,6-dimethyl-pyridin-2-yl)-hydrazinocarbonyl]-heptyl}-formamide.

N-((R)-2-{N'-[4-Ethyl-6-(3-hydroxy-piperidin-1-yl)-[1,3,5]triazin-2-yl]-hydrazinocarbonyl}-heptyl)-N-hydroxy-formamide.

N-[(R)-2-(N'-[4,5']Bipyrimidinyl-2-yl-hydrazinocarbonyl)-heptyl]-N-hydroxy-formamide.

N-((R)-2-{N'-[(Cyclopropyl-methyl-amino)-ethyl-[1,3,5]triazin-2-yl]-hydrazinocarbonyl}-heptyl)-N-hydroxy-formamide.

N-((R)-2-{N'-[4-Ethyl-6-((R)-3-hydroxy-pyrrolidin-1-yl)-[1,3,5]triazin-2-yl]-hydrazinocarbonyl}-heptyl)-N-hydroxy-formamide.

N-Hydroxy-N-[(R)-2-(N'-[3,3']Bipyridinyl-5-yl-hydrazinocarbonyl)-heptyl]-formamide.

N-Hydroxy-N-[(R)-2-(N'-(5-morpholin-4-yl-pyridin-3-yl)-hydrazinocarbonyl)-heptyl]-formamide.

N-Hydroxy-N-{(R)-2-[N'-(4-pyridin-3-yl-pyrimidin-2-yl)-hydrazinocarbonyl]-heptyl}-formamide.

N-Hydroxy-N-{(R)-2-[N'-(5,6,7,8-tetrahydro-quinazolin-2-yl)-hydrazinocarbonyl]-heptyl}-formamide.

N-[(R)-2-(N'-{[Cyclopropyl-1-(1-methyl-piperidin-4-yl)-amino]-ethyl-[1,3,5]triazin-2-yl}-hydrazinocarbonyl)-heptyl]-N-hydroxy-formamide.

N-((R)-2-{N'-[4-((R)-3-Dimethylamino-pyrrolidin-1-yl)-6-ethyl-[1,3,5]triazin-2-yl]-hydrazinocarbonyl}-heptyl)-N-hydroxy-formamide.

N-Hydroxy-N-[(R)-2-(N'-[5-(1H-pyrrol-2-yl)-pyridin-3-yl]-hydrazinocarbonyl)-heptyl]-formamide.

N-Hydroxy-N-[(R)-2-(N'-[(4-methyl-piperazin-1-yl)-trifluoromethyl-pyrimidin-4-yl]-hydrazinocarbonyl)-heptyl]-formamide.

N-Hydroxy-N-[(R)-2-(N'-(5-Furan-3-yl-pyridin-3-yl)-hydrazinocarbonyl)-heptyl]-formamide.

N-{(R)-5,5-Dimethyl-2-[N'-(4-trifluoromethyl-pyrimidin-2-yl)-hydrazinocarbonyl]-heptyl}-N-hydroxy-formamide.

N-{(R)-5,5-Dimethyl-2-[N'-(7-methyl-benzo[1,2,4]triazin-3-yl)-hydrazinocarbonyl]-heptyl}-N-hydroxy-formamide.

N-{(R)-5,5-Dimethyl-2-(4-methyl-pyridin-2-yl)-hydrazinocarbonyl]-heptyl}-N-hydroxy-formamide.

N-{(R)-2-Cycloheptyl-2-[N'-(4-trifluoromethyl-pyrimidin-2-yl)-hydrazinocarbonyl]-ethyl}-N-hydroxy-formamide.

N-{(R)-2-Cycloheptyl-2-[N'-(4-methyl-pyridin-2-yl)-hydrazinocarbonyl]-ethyl}-N-hydroxy-formamide.

N-{(R)-2-Cycloheptyl-2-[N'-(dimethylamino-ethyl-[1,3,5]triazin-2-yl)-hydrazinocarbonyl]-ethyl}-N-hydroxy-formamide.

N-{(R)-2-Cycloheptyl-2-[N'-(7-methyl-benzo[1,2,4]triazin-3-yl)-hydrazinocarbonyl]-ethyl}-N-hydroxy-formamide.

N-((R)-2-{N'-[4-Ethyl-6-(4-hydroxy-piperidin-1-yl)-[1,3,5]triazin-2-yl]-hydrazinocarbonyl}-heptyl)-N-hydroxy-formamide.

N-{(R)-5,5-Dimethyl-2-['-(5-methyl-benzo[1,2,4]triazin-3-yl)-hydrazinocarbonyl]-heptyl}-N-hydroxy-formamide.

N-{(R)-2-[N'-(4-Dimethylamino-quinazolin-2-yl)-hydrazinocarbonyl]-heptyl}-N-hydroxy-formamide.

N-Hydroxy-N-{(R)-2-[N'-(4-pyridin-4-yl-pyrimidin-2-yl)-hydrazinocarbonyl]-heptyl}-formamide.
N-Hydroxy-N-((R)-2-{N'-[4-(3-hydroxymethyl-phenyl)-pyrimidin-2-yl]-hydrazinocarbonyl}-heptyl)-formamide.
N-Hydroxy-N-((R)-2-{N'-[4-(4-hydroxymethyl-phenyl)-pyrimidin-2-yl]-hydrazinocarbonyl}-heptyl)-formamide.
N-((R)-2-{N'-[4-Ethyl-6-(3-methoxy-piperidin-1-yl)-[1,3,5]triazin-2-yl]-hydrazinocarbonyl}-heptyl)-N-hydroxy-formamide.
N-Hydroxy-N-{(R)-2-[N'-(7-methyl-benzo[1,2,4]triazin-3-yl)-hydrazinocarbonyl]-2-(4-methyl-cyclohexyl)-ethyl}-formamide.
N-[(R)-2-{N'-[Ethyl-(ethyl-methylamino)-[1,3,5]triazin-2-yl]-hydrazinocarbonyl}-2-(4-methyl-cyclohexyl)-ethyl}-N-hydroxy-formamide.
N-[(R)-2-{N'-[Ethyl-(ethyl-methylamino)-[1,3,5]triazin-2-yl]-hydrazinocarbonyl}-2-(4-methyl-cyclohexyl)-ethyl}-N-hydroxy-formamide.
N-Hydroxy-N-{(R)-2-[N'-(7-methyl-benzo[1,2,4]triazin-3-yl)-hydrazinocarbonyl]-2-(4-methyl-cyclohexyl)-ethyl}-formamide.
N-((R)-2-{N'-[4-(2,6-Dimethoxy-phenyl)-pyrimidin-2-yl]-hydrazinocarbonyl}-heptyl)-N-hydroxy-formamide.
N-((R)-2-{N'-[4-Ethyl-6-((R)-3-methoxy-pyrrolidin-1-yl)-[1,3,5]triazin-2-yl]-hydrazinocarbonyl}-heptyl)-N-hydroxy-formamide.
N-((R)-2-{N'-[4-Ethyl-6-(4-methoxy-piperidin-1-yl)-[1,3,5]triazin-2-yl]-hydrazinocarbonyl}-heptyl)-N-hydroxy-formamide.
N-Hydroxy-N-[(R)-2-(N'-(6-pyrrolidin-1-yl-pyrimidin-4-yl)-hydrazinocarbonyl]-heptyl]-formamide.
N-Hydroxy-N-[(R)-2-(N'-[6-(4-methyl-piperazin-1-yl)-pyrimidin-4-yl])-hydrazinocarbonyl)-heptyl]-formamide.
N-{(R)-2-[N'-(6-Dimethylamino-pyrimidin-4-yl)-hydrazinocarbonyl]-heptyl}-N-hydroxy-formamide.
N-{(R)-2-[N'-(Pyridin-4-yl-trifluoromethyl-pyrimidin-4-yl)-hydrazinocarbonyl]-heptyl}-N-hydroxy-formamide.
N-{(R)-2-[N'-(Pyridin-3-yl-trifluoromethyl-pyrimidin-4-yl)-hydrazinocarbonyl]-heptyl}-N-hydroxy-formamide.
N-{(R)-2-[N'-(2-Ethylamino-6-trifluoromethyl-pyrimidin-4-yl)-hydrazinocarbonyl]-heptyl}-N-hydroxy-formamide.
N-Hydroxy-N-((R)-2-{N'-[5-(4-methoxy-phenyl)-[1,2,4]triazin-3-yl]-hydrazinocarbonyl}-heptyl)-formamide.
N-Hydroxy-N-((R)-2-{N'-[4-(2,3,4-trimethoxy-phenyl)-pyrimidin-2-yl]-hydrazinocarbonyl}-heptyl)-formamide.
N-{(R)-4,4-Dimethyl-2-[N'-(4-trifluoromethyl-pyrimidin-2-yl)-hydrazinocarbonyl]-heptyl}-N-hydroxy-formamide.
N-{(R)-4,4-Dimethyl-2-[N'-(7-methyl-benzo[1,2,4]triazin-3-yl)-hydrazinocarbonyl]-heptyl}-N-hydroxy-formamide.
N-{(R)-4,4-Dimethyl-2-[N'-(5-methyl-benzo[1,2,4]triazin-3-yl)-hydrazinocarbonyl]-heptyl}-N-hydroxy-formamide.
N-{(R)-4,4-Dimethyl-2-[N'-(4-methyl-pyridin-2-yl)-hydrazinocarbonyl]-heptyl}-N-hydroxy-formamide.
N-Hydroxy-N-{(R)-2-[N'-(6-morpholinyl-pyrimidin-4-yl)-hydrazinocarbonyl]-heptyl}-formamide.
N-Hydroxy-N-[(R)-2-(N'-{5-[4-(2-hydroxy-ethoxy)-phenyl]-[1,2,4]triazin-3-yl}-hydrazinocarbonyl)-heptyl]-formamide.
N-{(R)-2-[N'-(4-Furan-2-yl-pyrimidin-2-yl)-hydrazinocarbonyl]-heptyl}-N-hydroxy-formamide.
N-((R)-2-{N'-[4-(3,5-Dimethyl-isoxazol-4-yl)-pyrimidin-2-yl]-hydrazinocarbonyl}-heptyl)-N-hydroxy-formamide.
N-Hydroxy-N-{(R)-2-[N'-(4-methyl-1-oxy-pyridin-2-yl)-hydrazinocarbonyl]-heptyl}-formamide.
2-(N'-{(R)-2-[(Formyl-hydroxy-amino)-methyl]-heptanoyl}-hydrazino)-6-methyl-nicotinic acid.
N-Hydroxy-N-{(R)-2-[N'-(3-methoxy-pyridin-2-yl)-hydrazinocarbonyl]-heptyl}-formamide.
N-Hydroxy-N-{(2R)-2-[(N'-{4-[4-(methylsulfonyl)phenyl]-pyrimidin-2-yl}-hydrazino)-carbonyl]-heptyl}-formamide.
N-Hydroxy-N-[(2R)-2-({N'-[4-(furan-3-yl)-pyrimidin-2-yl]-hydrazino}-carbonyl)-heptyl]-formamide.
N-[(2R)-2-({N'-[4-(2-aminophenyl)-pyrimidin-2-yl]-hydrazino}-carbonyl)-heptyl]-N-hydroxy-formamide.
N-Hydroxy-N-[(2R)-2-({N'-[5-(5-methyl-1,3,4-oxadiazol-2-yl)-4-(trifluoromethyl)-pyrimidin-2-yl]-hydrazino}-carbonyl)-heptyl]-formamide.
N-Hydroxy-N-((2R)-2-(cyclopentylmethyl)-3-{N'-[5-(5-methyl-1,3,4-oxadiazol-2-yl)-4-(trifluoromethyl)-pyrimidin-2-yl]-hydrazino}-3-oxopropyl)-formamide.
N-[(2R)-2-({N'-[6-(dimethylamino)-2-methyl-pyrimidin-4-yl]-hydrazino}-carbonyl)-heptyl]-N-hydroxy-formamide.
N-[(2R)-2-({N'-[2-Cyclopropyl-6-(dimethylamino)-pyrimidin-4-yl]-hydrazino}-carbonyl)-heptyl]-N-hydroxy-formamide.
N-Hydroxy-N-[(2R)-4-(2-thienyl)-2-({N'-[4-(trifluoromethyl)-pyrimidin-2-yl]-hydrazino}-carbonyl)-butyl]-formamide.
N-Hydroxy-N-[(2R)-2-{[N'-(4-methyl-pyrimidin-2-yl)hydrazino]carbonyl}-4-(2-thienyl)-butyl]-formamide.
N-[(2R)-2-[({'(4-Ethyl-6-[ethyl(methyl)amino]-1,3,5-triazin-2-yl}-hydrazino)-carbonyl]-4-(2-thienyl)butyl]-N-hydroxy-formamide.
N-Hydroxy-N-((2R)-3-oxo-2-(2-thienylmethyl)-3-{N'-[4-(trifluoromethyl)-pyrimidin-2-yl]-hydrazino}-propyl)-formamide.
N-Hydroxy-N-[(2R)-3-[N'-(4-methyl-pyrimidin-2-yl)hydrazino]-3-oxo-2-(2-thienylmethyl)-propyl]-formamide.
N-[(2R)-3-(N'-{4-Ethyl-6-[ethyl(methyl)amino]-1,3,5-triazin-2-yl}hydrazino)-3-oxo-2-(2-thienylmethyl)-propyl]-N-hydroxy-formamide.
N-Hydroxy-N-[(2R)-2-({N'-[2-methyl-6-(pyridin-2-yl)-pyrimidin-4-yl]-hydrazino}-carbonyl)-heptyl]-formamide.
N-Hydroxy-N-[(2R)-2-({N'-[6-(pyridin-2-yl-methyl)-pyridazin-3-yl]-hydrazino}-carbonyl)-heptyl]-formamide.
N-Hydroxy-N-[(2R)-2-({N'-[2-methyl-6-(morpholin-4-yl)-pyrimidin-4-yl]-hydrazino}-carbonyl)-heptyl]-formamide.
N-Hydroxy-N-[(2R)-2-({N'-[6-(morpholin-4-yl)-2-(trifluoromethyl)-pyrimidin-4-yl]-hydrazino}-carbonyl)-heptyl]-formamide.
N-Hydroxy-N-{(2R)-2-[(N'-{4-[methyl-(pyridin-2-yl)-amino]-pyrimidin-2-yl}-hydrazino)-carbonyl]-heptyl}-formamide.
N-Hydroxy-N-((2R)-2-(cyclopentylmethyl)-3-{N'-[4-cyclopropyl-6-(dimethylamino)-1,3,5-triazin-2-yl]-hydrazino}-3-oxopropyl)-formamide.
N-Benzo[1,3]dioxol-5-yl-methyl-hydrazinecarboxylic acid tert-butyl ester.
N-[(R)-2-(N'-Benzo[1,3]dioxol-5-yl-methyl-hydrazinocarbonyl)-heptyl]-N-hydroxy-formamide.
N-{(R)-2-[N'-(2,3-Dihydro-[1,4]dioxino[2,3-b]pyridin-7-yl-methyl)-hydrazinocarbonyl]-heptyl}-N-hydroxy-formamide.
N-{(R)-2-[N'-(4-Dimethylamino-benzyl)-hydrazinocarbonyl]-heptyl}-N-hydroxy-formamide.
N-Hydroxy-N-((R)-2-{N'-[2-(5,6,7,8-tetrahydro-[1,8]naphthyridin-2-yl)-ethyl]-hydrazinocarbonyl}-heptyl}-N-hydroxy-formamide.

N-Hydroxy-N-[(R)-2-(N'-quinolin-2-yl-methyl-hydrazinocarbonyl)-heptyl]-formamide.
N-Hydroxy-N-{(R)-2-[N'-(1,2,3,4-tetrahydro-quinolin-2-yl-methyl)-hydrazinocarbonyl]-heptyl}-formamide.
N-Hydroxy-N-[(R)-2-(N'-quinolin-6-yl-methyl-hydrazinocarbonyl)-heptyl]-formamide.
N-[(R)-2-(N'-Benzofuran-2-yl-methyl-hydrazinocarbonyl)-heptyl]-N-hydroxy-formamide.
N-[(R)-2-(N'-Cyclopropylmethyl-hydrazinocarbonyl)-heptyl]-N-hydroxy-formamide.
N-{(R)-2-[N'-(6-Fluoro-4H-benzo[1,3]dioxin-8-yl-methyl)-hydrazinocarbonyl]-heptyl}-N-hydroxy-formamide.
N-Hydroxy-N-{(R)-2-[N'-(4-methoxy-benzyl)-hydrazinocarbonyl]-heptyl}-formamide.
N-Hydroxy-N-{(R)-2-[N'-(2-methoxy-benzyl)-hydrazinocarbonyl]-heptyl}-formamide.
N-Hydroxy-N-{(R)-2-[N'-(tetrahydro-furan-3-yl-methyl)-hydrazinocarbonyl]-heptyl}-formamide.
N-[(R)-2-(N'-Furan-3-yl-methyl-hydrazinocarbonyl)-heptyl]-N-hydroxy-formamide.
N-{(R)-2-[N'-(2,3-Dihydro-benzo[1,4]dioxin-6-yl-methyl)-hydrazinocarbonyl]-heptyl}-N-hydroxy-formamide.
N-{(R)-2-[N'-(2,3-Dihydro-benzo[1,4]dioxin-2-yl-methyl)-hydrazinocarbonyl]-heptyl}-N-hydroxy-formamide.
N-Hydroxy-N-{(R)-2-[N'-(2-phenoxy-ethyl)-hydrazinocarbonyl]-heptyl}-formamide.
N-{(R)-2-[N'-((S)-2,3-Dihydroxy-propyl)-hydrazinocarbonyl]-heptyl}-N-hydroxy-formamide.
N-Hydroxy-N-{(R)-2-[N'-(5-methyl-isoxazol-3-yl-methyl)-hydrazinocarbonyl]-heptyl}-formamide.
N-((R)-2-{N'-[1-(1-Benzo[1,3]dioxol-5-yl-methanoyl)-piperidin-4-yl]-hydrazinocarbonyl}-heptyl)-N-hydroxy-formamide.
N-((R)-2-{N'-[1-(1-Benzofuran-2-yl-methanoyl)-piperidin-4-yl]-hydrazinocarbonyl}-heptyl)-N-hydroxy-formamide.
N-Hydroxy-N-[(R)-2-N'-{1-[1-(7-methoxy-benzofuran-2-yl)-methanoyl]-piperidin-4-yl}-hydrazinocarbonyl)-heptyl]-formamide.
N-{(R)-2-[N'-(1-Benzyl-piperidin-4-yl)-hydrazinocarbonyl]-heptyl}-N-hydroxy-formamide.
N-[(R)-2-(N'-{1-[1-(3,4-Dichloro-phenyl)-methanoyl]-piperidin-4-yl}-hydrazinocarbonyl)-heptyl]-N-hydroxy-formamide.
N-[(R)-2-(N'-{-[1-(2,3-Dichloro-phenyl)-methanoyl]-piperidin-4-yl}-hydrazinocarbonyl)-heptyl]-N-hydroxy-formamide.
N-Hydroxy-N-[(R)-2-(N'-{1-[1-(4-methyl-piperazin-1-yl)-methanoyl]-pentyl}-hydrazinocarbonyl)-heptyl]-formamide.
N-[(R)-2-(N'-Benzyl-hydrazinocarbonyl)-heptyl]-N-hydroxy-formamide.

General Synthetic Sequence

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of Formula (1) that can be prepared from the common racemic intermediate (8), or common choral intermediates (17) and (25).

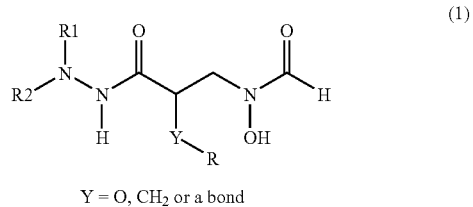

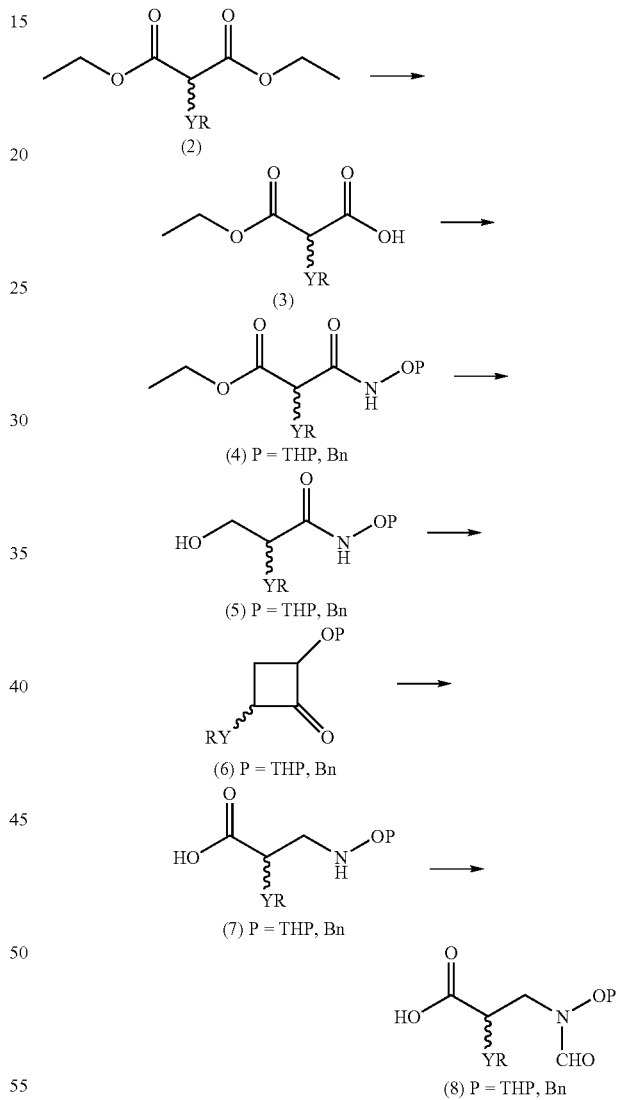

As shown in Scheme 1, intermediate (8) can be prepared by reacting the mono-substituted dialkyl malonate (2) with a base, such as potassium hydroxide, in an appropriate solvent, such as ethanol/water, to afford the mono-acid (3). Coupling of (3) with O-benzylhydroxylamine or O-(tetrahydro-2H-pyran-2-yl)hydroxylamine in the presence of a coupling reagent, such as 1-[3-(dimethylamino)propyl]-3-ethylcarbodiimide hydrochloride (EDCI), and a base, such as 4-dimethylaminopyridine (DMAP), in an appropriate solvent, such as dichloromethane, gives the amide (4), where P is benzyl or tetrahydro-2H-pyran-2-yl. Reduction of the ester functionality of compound (4) with a reducing agent, such as lithium borohydride, in an appropriate solvent, such as tetrahydrofuran, at room temperature provides the alcohol (5). Treatment of the alcohol (5) under Mitsunobu conditions affords the lactam. (6). The same transformation may be achieved by treating (5) with triphenylphosphine, carbon tetrachloride and a base, such as triethylamine, to obtain (6). Hydrolysis of the lactam (6) using, for example, lithium hydroxide in an appropriate solvent mixture, such as THF-H$_2$O-MeOH, gives acid (7). Formylation of the amine group of (7) is achieved using formic acid and acetic anhydride in a solvent, such as dichloromethane, to provide the formylated compound (8).

Any racemates can be resolved at the level of any intermediate during the synthesis or at the level of the final product using, for example, a chiral chromatography method, to provide compound (8) in each of two enantiomeric forms.

Alternatively, an enantiomer of intermediate (8), such as (18) in Scheme 2 or (27) in Scheme 3, can be prepared by reacting an appropriate acid chloride (9) with a chiral agent, such as Evans' chiral oxazolidinone, in the presence of a base, such as n-butyl lithium, to afford the chiral intermediate (10) in Scheme 2 or (19) in Scheme 3. Treatment of the compound (10) or (19) with a base, such as diisopropylethylamine, in the presence of a chelating agent, such as titanium tetrachloride, in a solvent, such as tetrahydrofuran, followed by addition of an electrophile, such as benzyloxymethylchloride, provides either of two chiral compounds (11) or (20), depending on the selection of chiral auxiliary. Conversion of compound (11) or (20) to the corresponding hydroxyacid (14) or (23) can be achieved by a sequence comprising oxidative cleavage of the chiral oxazolidinone, using, for example H$_2$O$_2$ and lithium hydroxide, to the respective intermediates (12) or (21), followed by hydrogenolysis, to afford intermediates (13) or (21), respectively. Compounds (10) or (19) can also be converted to intermediates (14) or (23), respectively, in a two-step procedure. For this transformation, (10) or (19) can be treated with a base, such as diisopropylethylamine, in the presence of a chelating agent, such as titanium tetrachloride, in a solvent, such as tetrahydrofuran, followed by addition of trioxane or any other formaldehyde equivalent to provide compounds (13) or (22), which are then submitted to oxidative cleavage of the chiral oxazolidinone, using, for example H$_2$O$_2$ and lithium hydroxide, to the respective acids (14) or (23), respectively.

Coupling of the acid (14) or (23) with benzyloxyamine or O-(tetrahydro-2H-pyran-2-yl)hydroxylamine in the presence of coupling agents, such as EDCI-DMAP, yields the amides (15) or (24), respectively. These can be cyclized to the azetidin-2-ones (16) or (25) using Mitsunobu conditions or a combination of triphenylphosphine-carbon tetrachloride-triethylamine. Hydrolysis of the azetidin-2-one (16) or (25), using for example lithium hydroxide, in an appropriate solvent, gives the corresponding acid (17) or (26), respectively. Conversion of compound (17) or (26) to the carboxylic acid (18) or (27) can be achieved using an appropriate formylating agent, such as formic acid/acetic anhydride or methyl formate, in neat reagents or in an appropriate solvent, such as dichloromethane.

Scheme 2

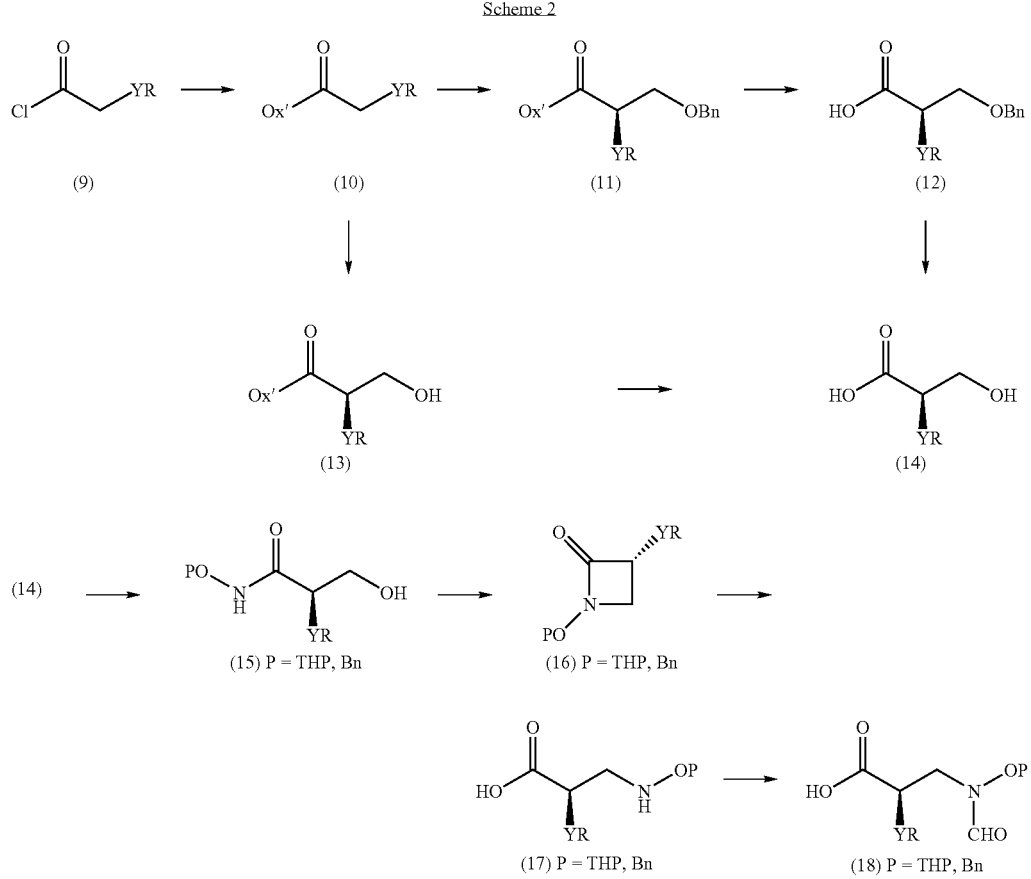

Scheme 3
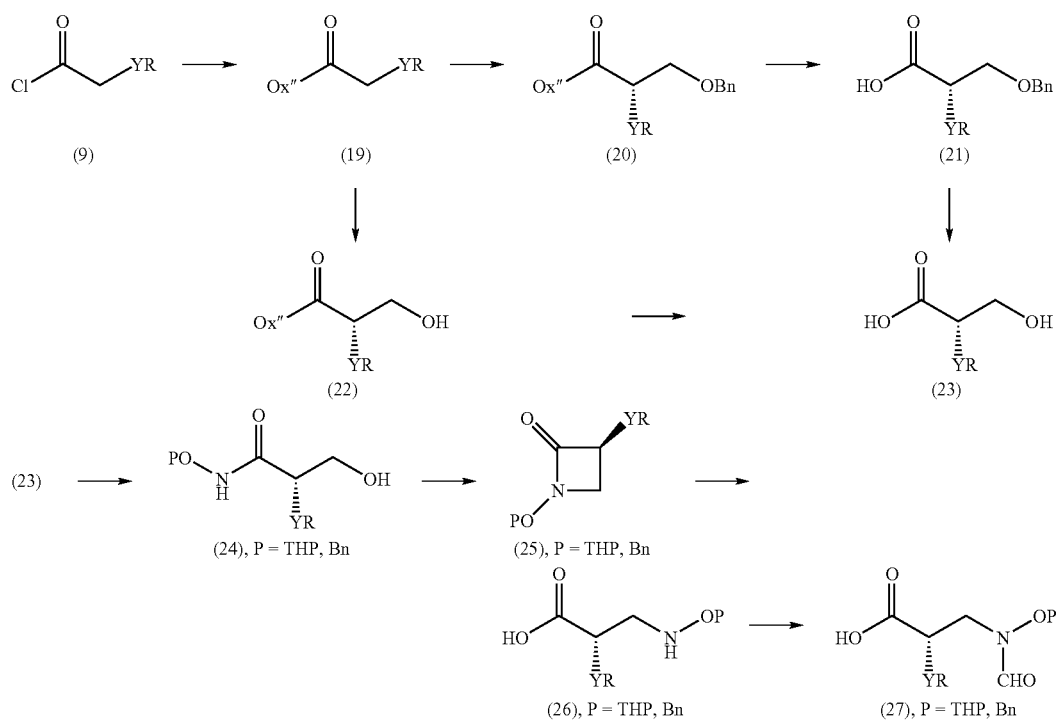
As shown in Scheme 4, compound (8) can be coupled to CBZNHNH$_2$, using conditions such as DMAP-EDCI or EDCI-HOAt-NMM, and debenzylated to generate compound (28). Reaction of (28) with the halide or trifluoromethyl R1X affords (1) where R2 is H. Similarly, compounds (18) and (27) can be submitted to the same procedure to afford, respectively, (31) where R2 is H and (32) where R2 is H.
Scheme 4
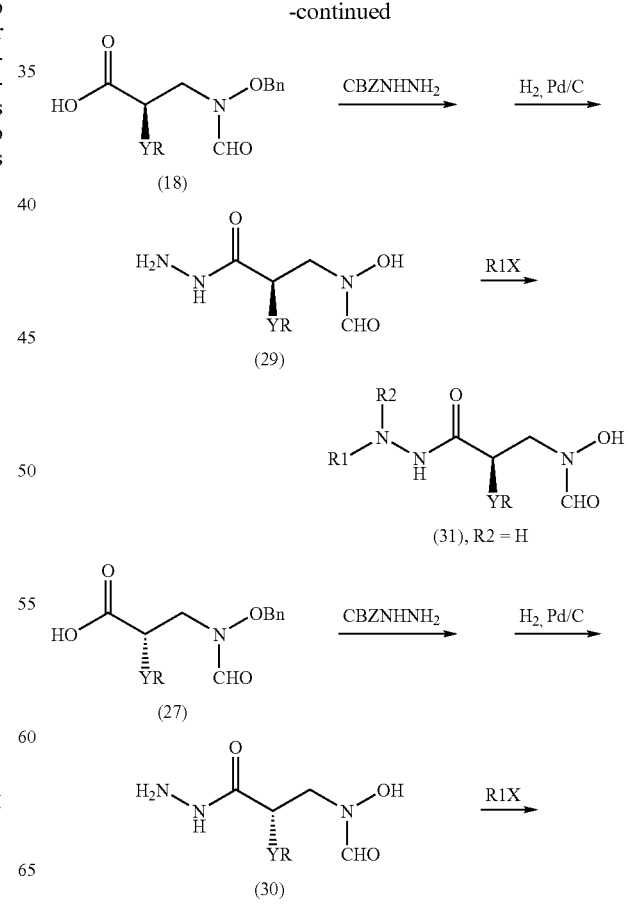

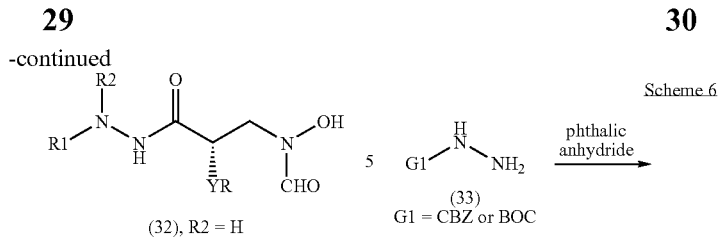

Alternatively, as shown in Scheme 5, compound (28) is submitted to a reductive alkylation with the ketone R1C(O)R2 using as reductant, for example, sodium cyanoborohydride, to afford compound (1). If the aldehyde R1C(O)H is used in the reductive alkylation instead, compound (1) where R2 is H is formed. Similarly, compound (29) can be submitted to reductive alkylation with the ketone R1C(O)R2 to afford compound (31), or with the aldehyde R1C(O)H to afford compound (31) where R2 is H. Similarly, compound (30) can be submitted to reductive alkylation with the ketone R1C(O)R2 to afford compound (32), or with the aldehyde R1C(O)H to afford compound (32) where R is H.

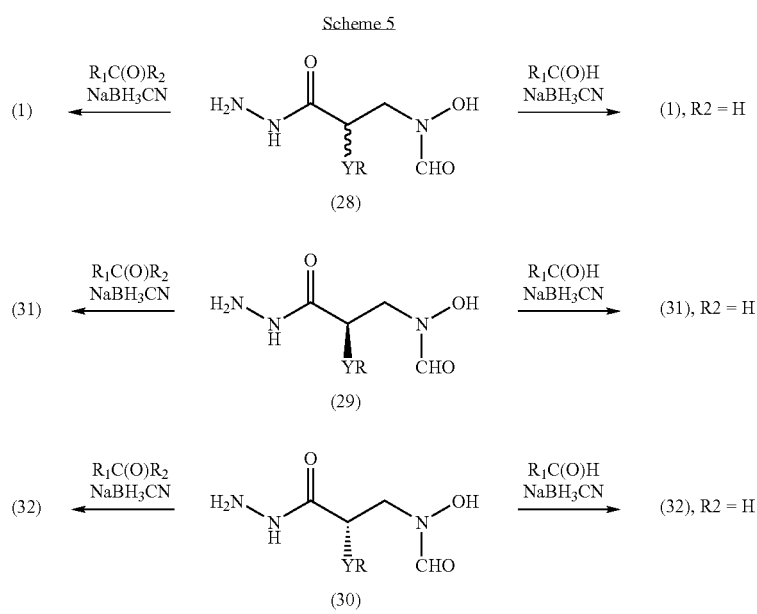

Alternatively, as shown in Scheme 6, the monoprotected hydrazine G1NHNH2 (33), where G1 is benzyloxycarbonyl or tert-butoxycarbonyl, can be reacted with phthalic anhydride to yield intermediate (34). (34) can be coupled to the alcohol R1OH under Mitsunobu conditions to yield (35), which upon hydrazinolysis originates hydrazine (36). Coupling of (36) to acid (8) using conditions such as DMAP/EDCI or EDCI/HOAt/NMM affords (37). (37) can be fully deprotected in one step using hydrogenolysis when G1 is benzyloxycarbonyl and P is benzyl, in one step using acidic conditions when G1 is tert-butoxycarbonyl and P is O-(tetrahydro-2H-pyran-2-yl), or in two steps (by acid treatment and hydrogenolysis) when G1 is benzyloxycarbonyl and P is O-(tetrahydro-2H-pyran-2-yl), or G1 is tert-butoxycarbonyl and P is benzyl. In all three cases, compound (1) where R2 is H is formed. Similarly, compounds (18) and (27) can be submitted to the same procedure to afford, respectively, (31) where R2 is H or (32) where R2 is H.

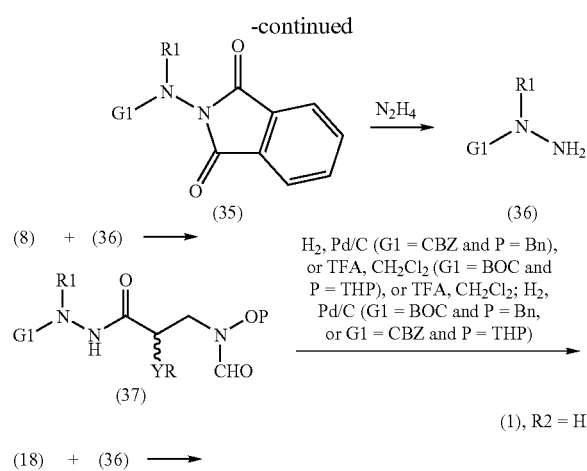

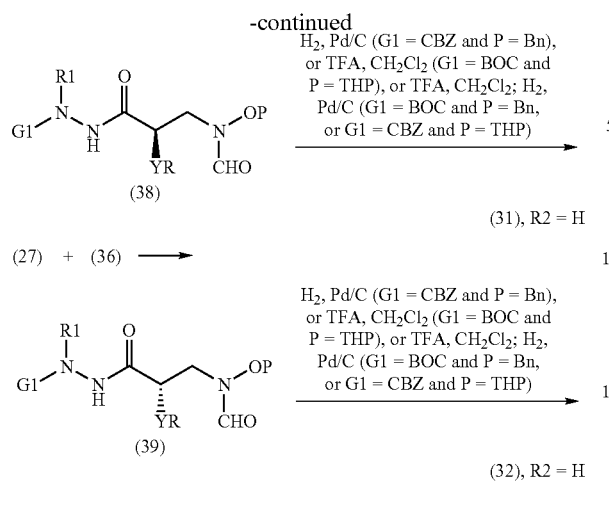

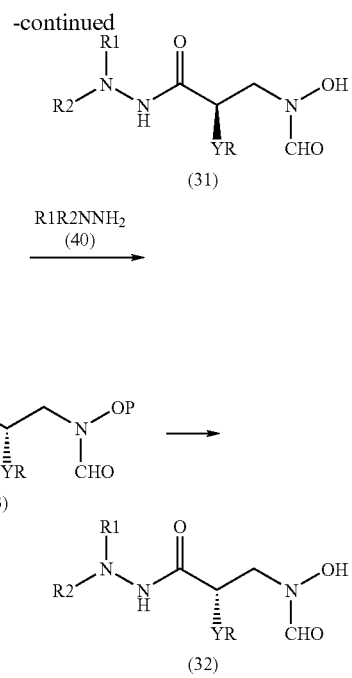

As shown in Scheme 7, coupling of the acid (8) with the hydrazine R1R2NNH$_2$ (40), using conditions such as DMAP-EDCI or EDCI-HOAt-NMM, provides the hydrazide (41). Final deprotection (hydrogenolysis using a catalyst, such as 10% Pd/C, in an appropriate solvent, such as ethanol, in the case that P is Bn; treatment with 80% acetic acid-water at room temperature or 40° C. in the case that P is THP) gives the desired compound (1). Similarly, coupling of the chiral acid (18) or (27) with the hydrazine (40) provides the corresponding hydrazide (42) or (43). Final deprotection gives the final desired compound (31) or (32).

Scheme 7

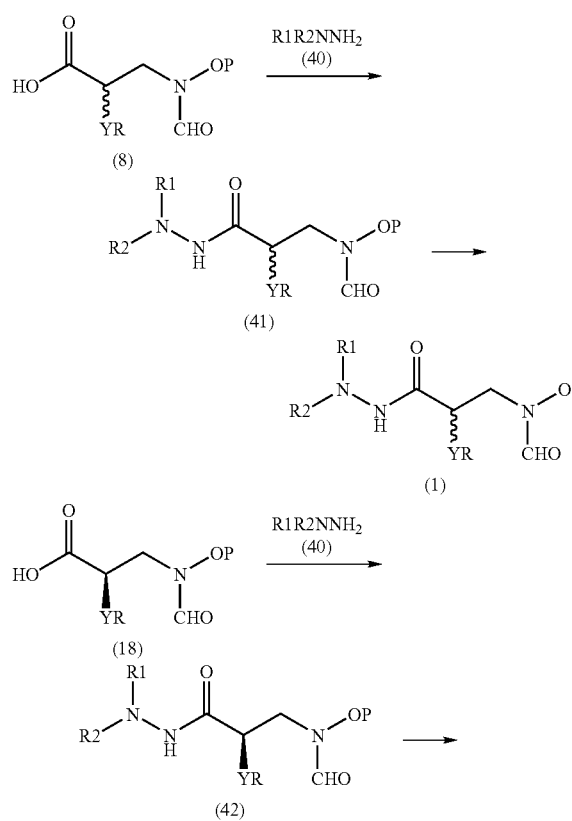

Hydrazines of general structure R1R2NNH$_2$ (40) may be purchased from available commercial sources or prepared according to literature methods by those skilled in the art. The following examples of specific structures of hydrazine (40) and the synthetic methods used to generate them are merely illustrative and are not to be construed as a limitation of the scope of the present invention.

Hydrazines (40) where R2 is alkyl or hydrogen, and R1 has the general structure (44) may be prepared from appropriate precursors shown in Scheme 8, 9 and 10.

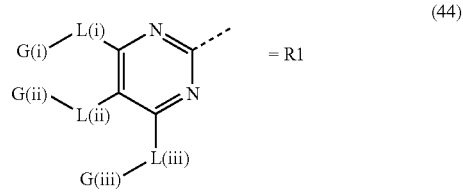

As shown in Scheme 8, hydrazine (40) where R1 is (44) can be prepared from precursor (45) by treatment with an appropriate hydrazine, such as hydrazine monohydrate, in an appropriate solvent, such as methanol. Alternatively, as shown in Scheme 9, hydrazine (40) where R1 is (44) can be prepared from precursor (46) by oxidation to the sulfone via treatment with an appropriate oxidant such as meta-chloroperbenzoic acid (m-CPBA) in an appropriate solvent such as methylene chloride. Further treatment with an appropriate hydrazine, such as hydrazine monohydrate, in an appropriate solvent, such as methanol, then provides the desired product (40) where R1 is (44). Alternatively, as shown in Scheme 10, hydrazine (40) where R1=(44) can be prepared from (47) via treatment with sodium nitrate in an appropriate solvent such as aqueous sulfuric acid to give (48). Compound (48) is then treated with an appropriate halogenating reagent such as phosphorus oxychloride at reflux followed by treatment with an appropriate hydrazine, such as hydrazine monohydrate, in an appropriate solvent, such as methanol, to provide intermediate (40) where R1 is (44). Compounds (45), (46), (47) and (48) are available from commercial sources, or can be prepared via literature methods by those skilled in the art (Pyrimidines. Brown, D. J. In "The Chemistry of Heterocyclic Compounds" vol. 52, Taylor, E. C., ed.; Wiley: New York, 1994).

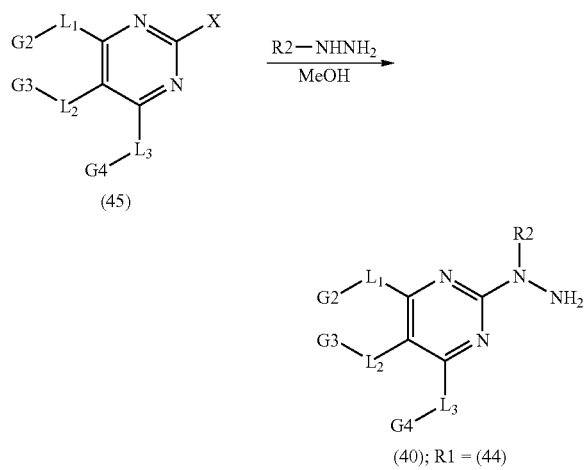

X = halogen; L1, L2, L3 = bond, N—G5, O, S;
G2, G3, G4, G5 = H, Alkyl, Acyl, Heterocyclic, Aryl, Heteroaryl.

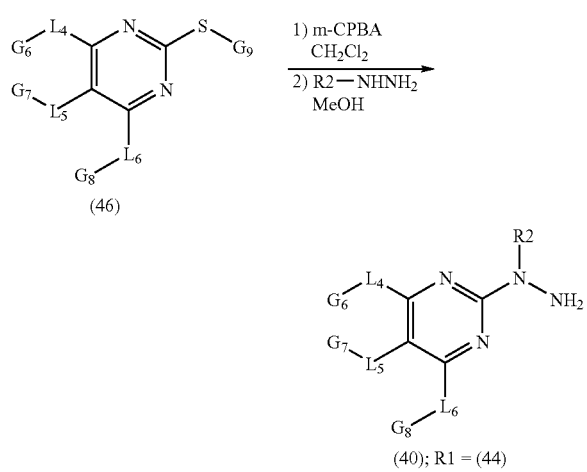

L4, L5, L6 = bond, N—G10, O;
G6, G7, G8, G10 = H, Alkyl, Acyl, Heterocyclic, Aryl, Heteroaryl; G9 = Alkyl, Aryl.

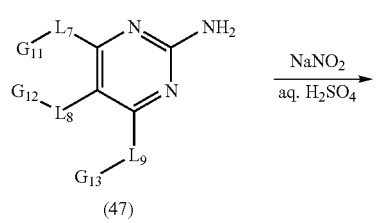

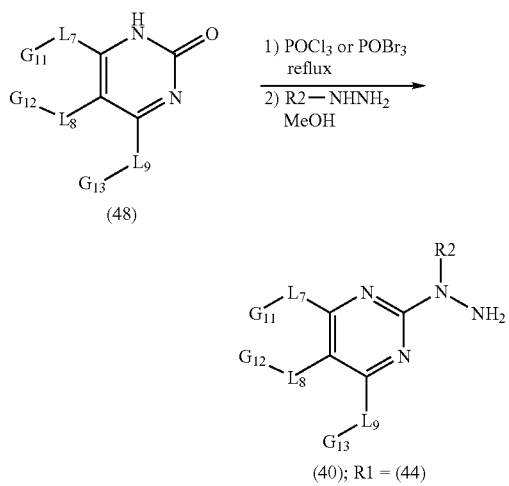

L7, L8, L9 = bond, O S;
G11, G12, G13 = H, Alkyl, Acyl, Heterocyclic, Aryl, Heteroaryl.

Hydrazines (40) where R2 is hydrogen, and R1 has the general structure (49) may be prepared from appropriate precursors shown in Schemes 11 and 12.

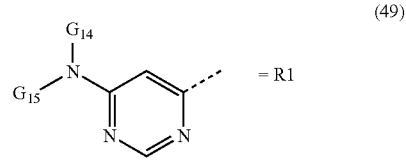

G14, G15 = H, Alkyl, Aryl, Heteroaryl, Heterocyclic

As shown in Scheme 11, 4,6-dichloropyrimidine (50) may be reacted with tert-butylcarbazate in the presence of base, such as diisopropylethylamine, at 100° C. in an appropriate solvent such as ethanol to give compound (51). The amine G14G15NH may be reacted with (51) to afford compound (52), which may be deprotected under acidic conditions, such as trifluoroacetic acid in dichloromethane, to afford compound (40), where R2 is hydrogen and R1 is (49).

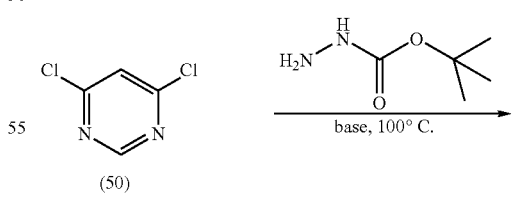

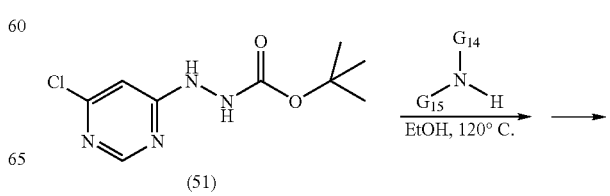

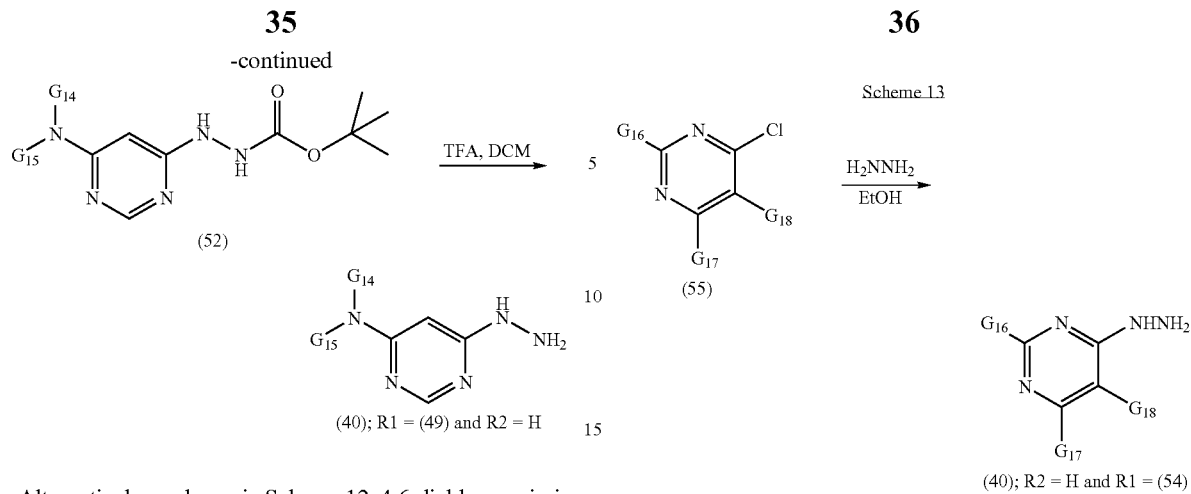

Alternatively, as shown in Scheme 12, 4,6-dichloropyrimidine (50) may be reacted with one equivalent of amine G14G15NH in the presence of base, such as triethylamine or diisopropylethylamine, to afford compound (53), which may be treated with excess hydrazine to afford compound (40), where R2 is hydrogen and R1 is (49).

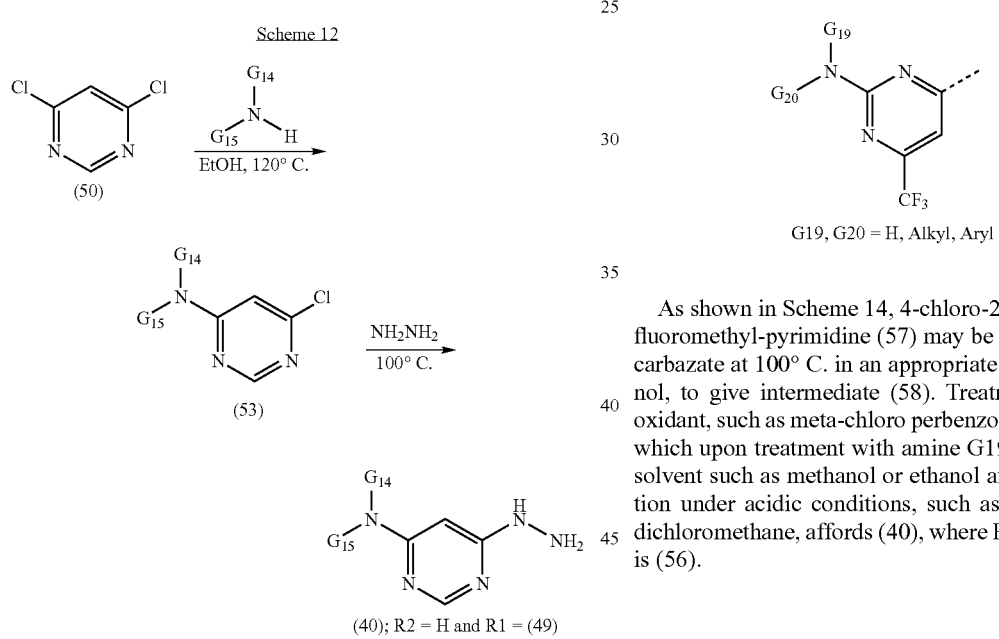

Hydrazines (40) where R2 is hydrogen, and R1 has the general structure (54) may be prepared from an appropriate precursor such as (55), by treatment with anhydrous hydrazine in an appropriate solvent such as ethanol, as shown in Scheme 13.

Hydrazines (40) where R2 is hydrogen and R1 has the general structure (56) may be prepared from an appropriate precursor shown in Scheme 14.

As shown in Scheme 14, 4-chloro-2-methylsulfanyl-6-trifluoromethyl-pyrimidine (57) may be treated with tert-butyl carbazate at 100° C. in an appropriate solvent, such as ethanol, to give intermediate (58). Treatment of (58) with an oxidant, such as meta-chloro perbenzoic acid, produces (59), which upon treatment with amine G19G20NH in a suitable solvent such as methanol or ethanol affords (60). Deprotection under acidic conditions, such as trifluoroacetic acid in dichloromethane, affords (40), where R2 is hydrogen and R1 is (56).

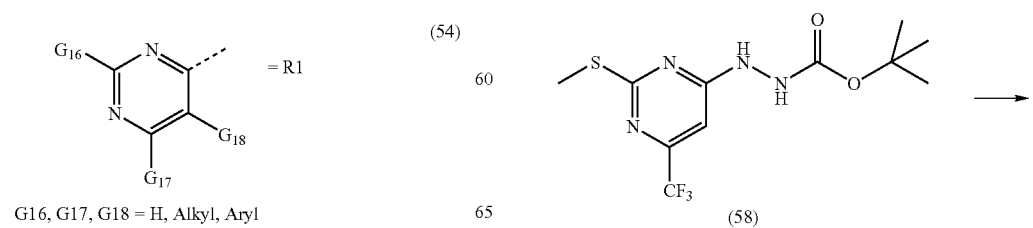

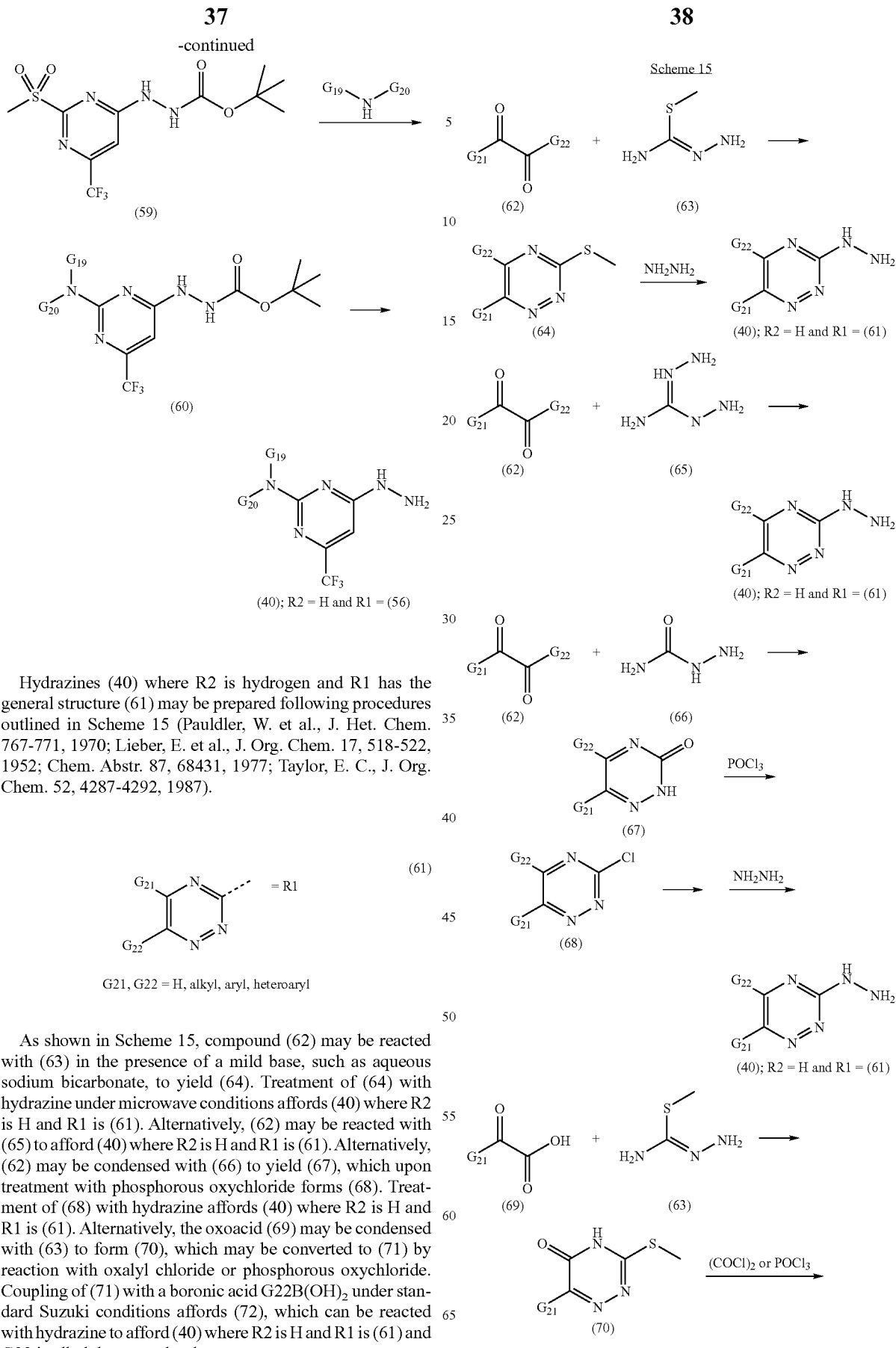

Hydrazines (40) where R2 is hydrogen and R1 has the general structure (61) may be prepared following procedures outlined in Scheme 15 (Pauldler, W. et al., J. Het. Chem. 767-771, 1970; Lieber, E. et al., J. Org. Chem. 17, 518-522, 1952; Chem. Abstr. 87, 68431, 1977; Taylor, E. C., J. Org. Chem. 52, 4287-4292, 1987).

As shown in Scheme 15, compound (62) may be reacted with (63) in the presence of a mild base, such as aqueous sodium bicarbonate, to yield (64). Treatment of (64) with hydrazine under microwave conditions affords (40) where R2 is H and R1 is (61). Alternatively, (62) may be reacted with (65) to afford (40) where R2 is H and R1 is (61). Alternatively, (62) may be condensed with (66) to yield (67), which upon treatment with phosphorous oxychloride forms (68). Treatment of (68) with hydrazine affords (40) where R2 is H and R1 is (61). Alternatively, the oxoacid (69) may be condensed with (63) to form (70), which may be converted to (71) by reaction with oxalyl chloride or phosphorous oxychloride. Coupling of (71) with a boronic acid G22B(OH)$_2$ under standard Suzuki conditions affords (72), which can be reacted with hydrazine to afford (40) where R2 is H and R1 is (61) and G22 is alkyl, heteroaryl only.

-continued

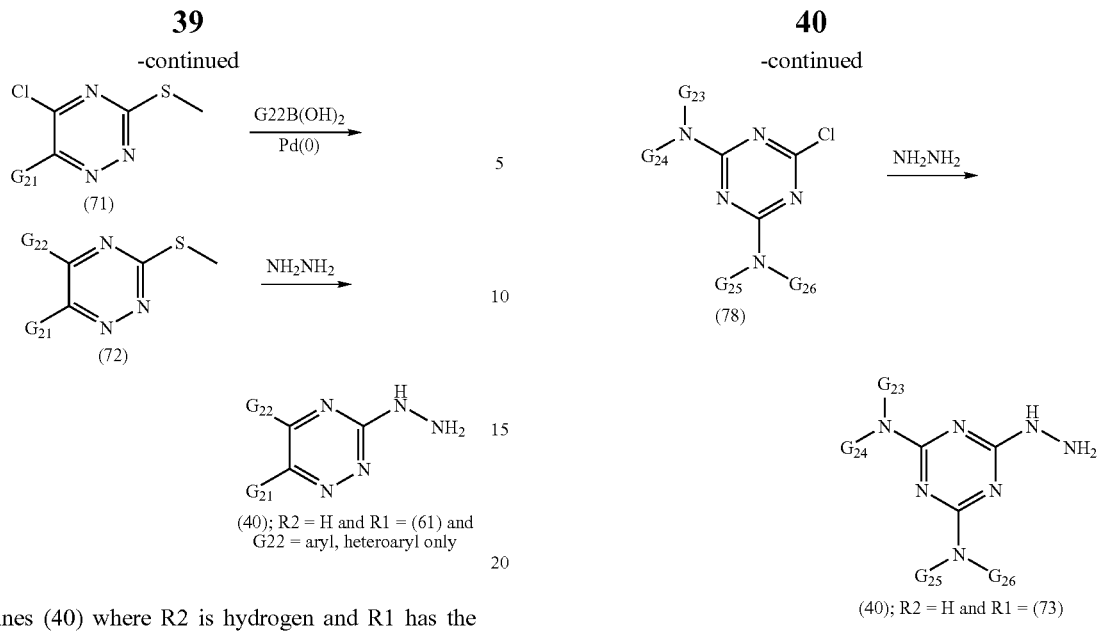

Hydrazines (40) where R2 is hydrogen and R1 has the general structure (73) may be prepared following procedures outlined in Scheme 16.

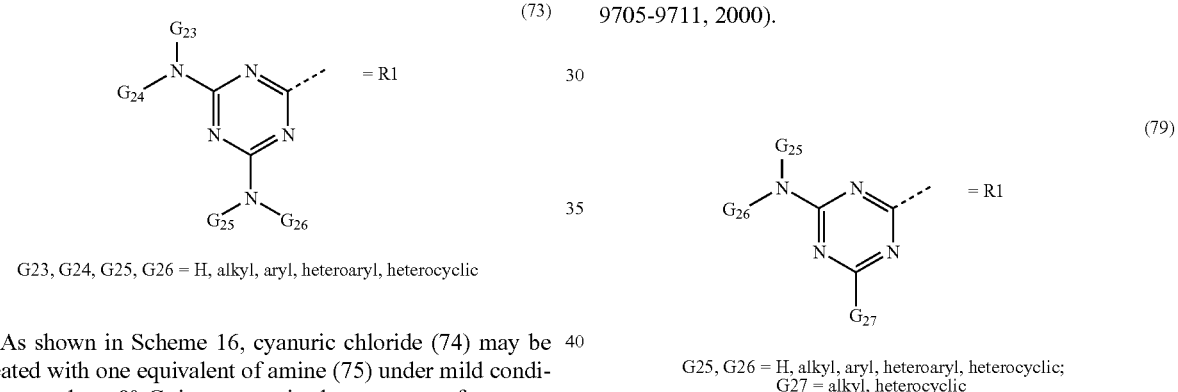

G23, G24, G25, G26 = H, alkyl, aryl, heteroaryl, heterocyclic

As shown in Scheme 16, cyanuric chloride (74) may be treated with one equivalent of amine (75) under mild conditions, such as 0° C. in acetone in the presence of aqueous potassium carbonate, to afford (76). Treatment of (76) with amine (77) under conditions such as 25° C. in acetone in the presence of potassium carbonate yields (78). Displacement of the remaining chloride in (78) with hydrazine affords (40) where R2 is H and R1 is (73).

Scheme 16

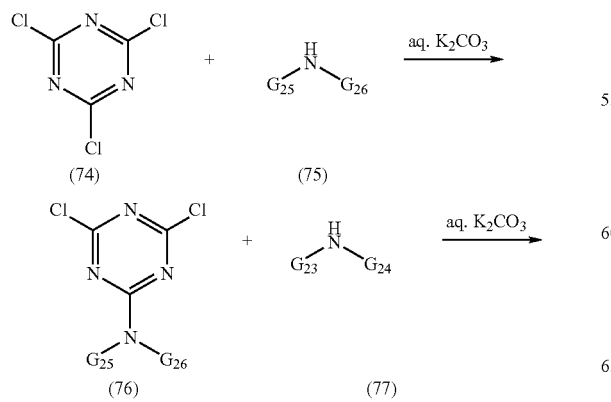

Hydrazines (40) where R2 is hydrogen and R1 has the general structure (79) may be prepared following procedures outlined in Scheme 17 (Menicagli, R. et al., Tetrahedron, 56, 9705-9711, 2000).

G25, G26 = H, alkyl, aryl, heteroaryl, heterocyclic; G27 = alkyl, heterocyclic

As shown in Scheme 17, cyanuric chloride (74) may be reacted with the Grignard compound (80) to form (81), which upon treatment with amine (77) affords monochloride (82). Hydrazinolysis of (82) yields (40) where R2 is H and R1 is (73).

Scheme 17

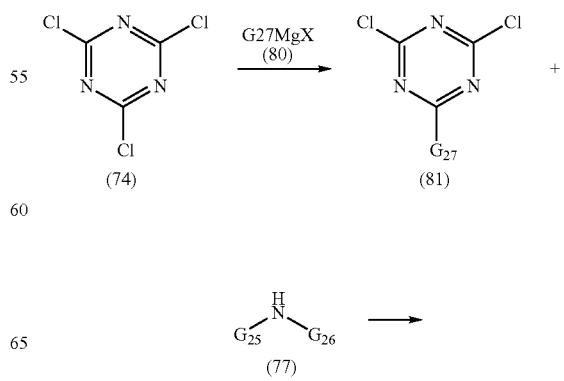

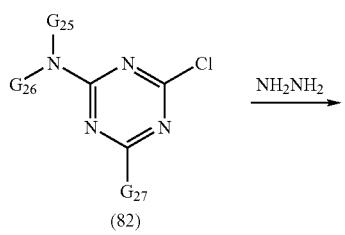

(82)

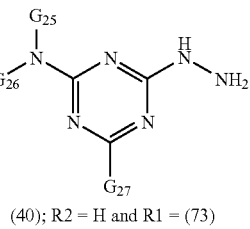

(40); R2 = H and R1 = (73)

Hydrazines (40) where R2 is hydrogen and R1 has the general structure (83) may be prepared following procedures outlined in Scheme 18 (Kobe, J. et al., Monatsh. Chem. 101, 724-735, 1970; Janietz, D. and Bauer, M., Synthesis 33-34, 1993).

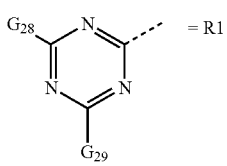

G28 = aryl, heteroaryl; G29 = alkyl, aryl, heteroaryl, heterocyclic, NG30G31;
G30, G31 = aryl, alkyl, heteroaryl, heterocyclic As shown in Scheme 18, compound (84) may be coupled to boronic acid G28B(OH)$_2$ or equivalent under Suzuki coupling protocols to afford (85), which upon hydrazinolysis yields (40) where R2 is H and R1 is (83).

Scheme 18

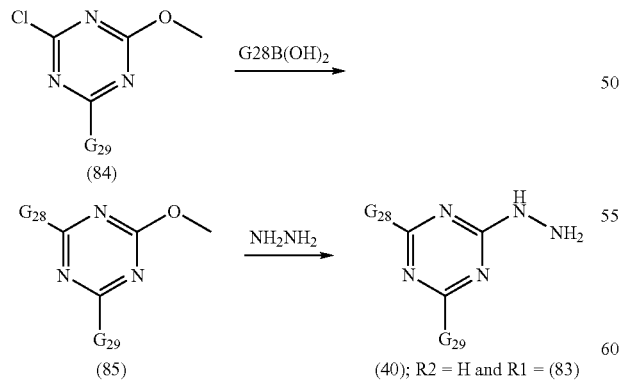

Hydrazines (40) where R2 is hydrogen and R1 has the general structure (86) may be prepared following procedures outlined in Scheme 19.

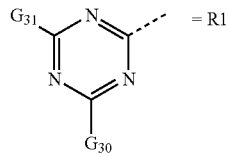

G30, G31 = alkyl, heterocyclic

As shown in Scheme 19, sequential reaction of cyanuric chloride (74) with Grignard compounds G30MgX and G31MgX in a solvent such as benzene affords monochloride (87), which can be treated with hydrazide to afford (40) where R2=H and R1=(86).

Scheme 19

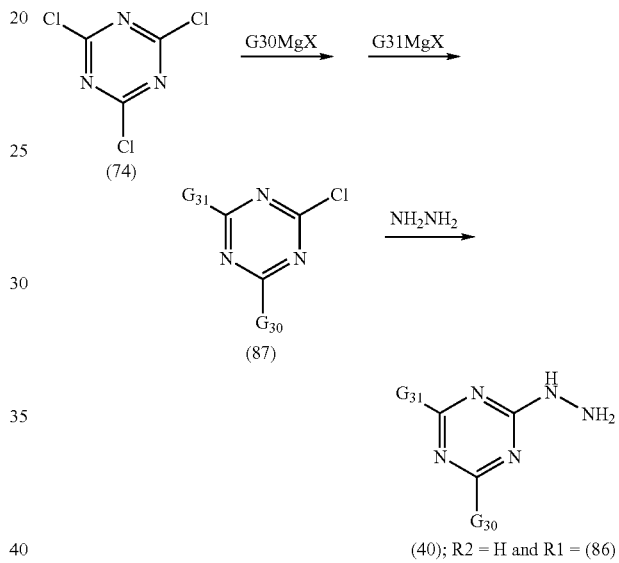

Hydrazines (40) where R2 is hydrogen and R1 has the general structure (88) may be prepared following procedures outlined in Scheme 20.

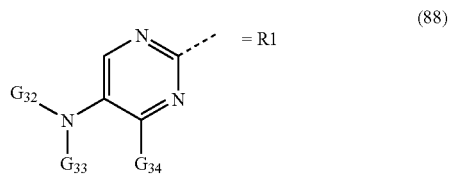

G32 = alkyl, aryl, heteroaryl, heterocyclic;
G33 = hydrogen, alkyl, aryl, heteroaryl, heterocyclic;
G34 = alkyl As shown in Scheme 20, (89) can be reduced to (90) using reducing conditions such as iron and acetic acid. Sequential treatment of (90) with alkylating agents G32X and G33X (where X is halide or trifluoromethylsulfonate) affords (91). Alternatively, treatment of (90) with one equivalent of G32X affords (91) where G33 is H. Oxidation of (91) to the corresponding sulfoxide or sulfone using as oxidant such as meta-chloro perbenzoic acid, and subsequent treatment with hydrazine affords (40) where R2 is H and R1 is (88).

Scheme 20

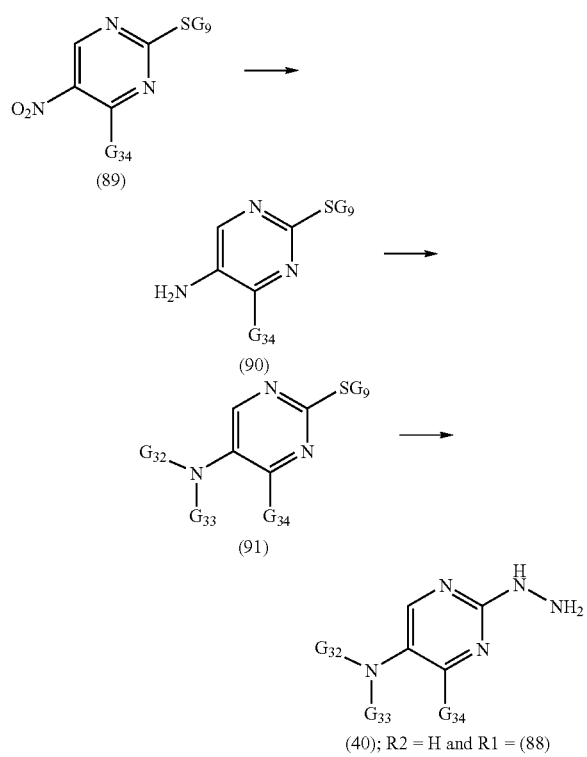

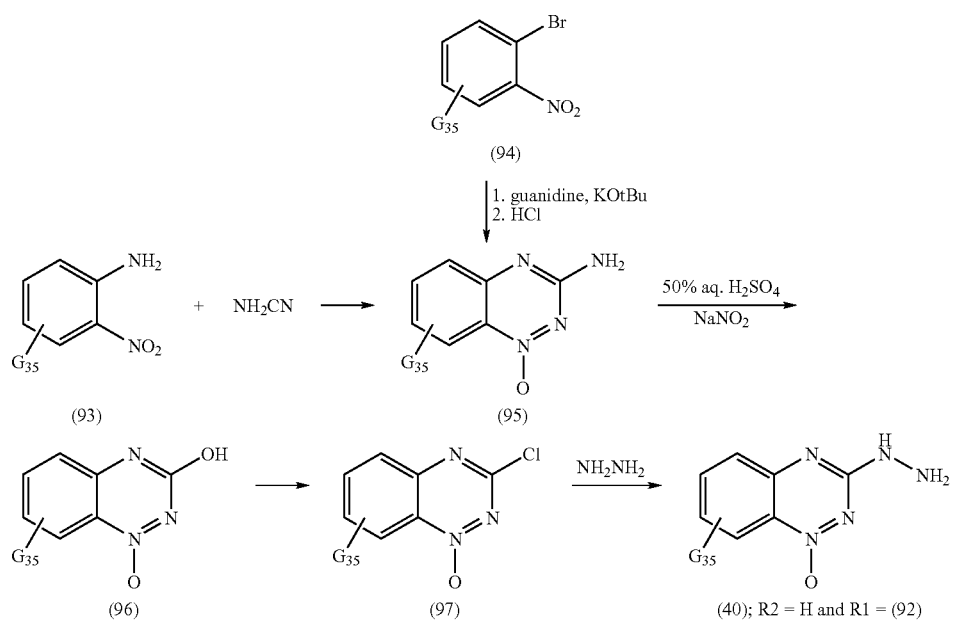

G35 = alkyl, aryl, heteroaryl, heterocyclic, alkoxy, halogen, amino; m, q = 0, 1

As shown in Scheme 21, (93) may be reacted with cyanamide in the presence of a base such as aqueous sodium hydroxide to afford (95). Alternatively, treatment of (94) with guanidine and a base such as potassium tert-butoxide, followed by acidification, affords (95) as well. Reaction of (95) with sodium nitrite in acidic solution yields (96). Conversion of (96) to the respective chloride (97) may be achieved with phosphorous oxychloride, for example. Hydrazinolysis of (97) affords (40) where R2 is H and R1 is (92) and m=0 and q=1; the N-oxide in this molecule may be reduced by hydrogenolysis in the presence of Pd on carbon and the resulting hydrazine may then be coupled to acid (8), (18) or (27). Alternatively, the 1-N-oxide benzotriazine hydrazine may be coupled to the acids (8), (18) or (27), and the resulting compounds may then be submitted to hydrogenolysis in the presence of Pd on carbon in order to reduce the N-oxide group.

Hydrazines (40) where R2 is hydrogen and R1 has the general structure (92) may be prepared following procedures outlined in Scheme 21 (Wolf, F. J. et al., J. Am. Chem. Soc. 76, 3551-3553, 1954; Hay, M. et al., J. Med. Chem. 46, 169-182, 2003) and Scheme 22 (Ley, K. et al., Angew. Chem. Int. Ed. 11, 1009-1010, 1972).

Alternatively, as shown in Scheme 22, (98) may be reacted with disodium cyanamide in a solvent such as a mixture of methanol and water to afford (99), which tautomerizes to (100) in the presence of acid. Treatment of (100) with sodium nitrite in acidic media provides (101). Reaction of (101) with phosphorous oxychloride, followed by hydrazinolysis, affords (40), where R2 is H and R1 is (92) and m=q=1; the N-oxide groups in this molecule may be reduced by hydrogenolysis in the presence of Pd on carbon and the resulting hydrazine may then be coupled to acid (8), (18) or (27). Alternatively, the 1,4-bis-N-oxide benzotriazine hydrazine may be coupled to acid (8), (18) or (27), and the resulting compound may then be reduced by hydrogenolysis in the presence of Pd on carbon.

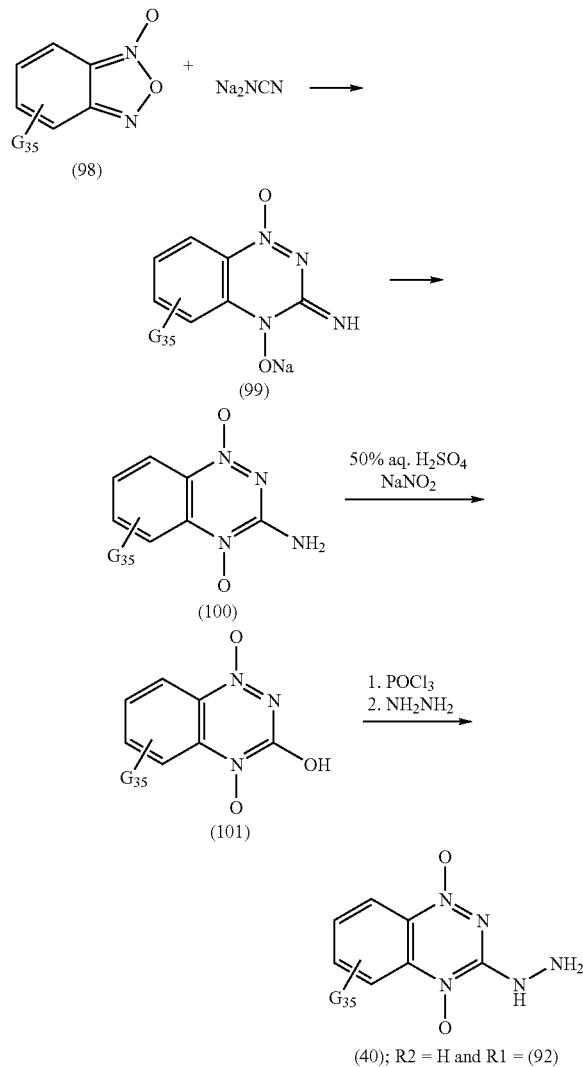

Scheme 22

SYNTHETIC EXAMPLES

The invention will now be described by reference to the following examples which are merely illustrative and are not to be construed as a limitation of the scope of the present invention.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Hz (Hertz);
TLC (thin layer chromatography);
Tr (retention time);
RP (reverse phase);
MeOH (methanol);
i-PrOH (isopropanol);
EtOH (ethanol);
TEA (triethylamine);
TFA (trifluoroacetic acid);
THF (tetrahydrofuran);
DMSO (dimethylsulfoxide);
AcOEt or EtOAc (ethyl acetate);
DCM (dichloromethane);
DMF (N,N-dimethylformamide);
CDI (1,1-carbonyldiimidazole);
HOAc (acetic acid);
HOSu (N-hydroxysuccinimide);
Ac (acetyl);
HOBT (1-hydroxybenzotriazole);
BOC (tert-butyloxycarbonyl);
mCPBA (meta-chloroperbenzoic acid);
FMOC (9-fluorenylmethoxycarbonyl);
DCC (dicyclohexylcarbodiimide);
CBZ (benzyloxycarbonyl);
NMM (N-methyl morpholine);
HOAt (1-hydroxy-7-azabenzotriazole);
DMAP (4-dimethylaminopyridine);
Bn (benzyl);
TBAF (tetra-n-butylammonium fluoride);
THP (tetrahydro-2H-pyran-2-yl)
HPLC (high pressure liquid chromatography);
BOP (bis(2-oxo-3-oxazolidinyl)phosphinic chloride);
EDCI (1-ethyl-3-[3-dimethylaminopropyl]carbodiimide hydrochloride);
HBTU (O-Benzotriazole-1-yl-N,N,N',N'-tetramethyluronium hexafluorophosphate).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

$^1$H NMR (hereinafter also "NMR") spectra were recorded on a Varian VXR-300, a Varian Unity-300, a Varian Unity-400 instrument, a Brucker AVANCE-400, a General Electric QE-300 or a Bruker AM 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 4.5% to 90% CH$_3$CN (0.02% TFA) in 3.2 min with a 0.4 min hold and 1.4 min re-equilibration; detection by MS, UV at 214 nm, and a light scattering detector (ELS). Column: 1×40 mm Aquasil (C18).

For preparative (prep) hplc; ca 50 mg of the final products were injected in 500 uL of DMSO onto a 50×20 mm I. D. YMC CombiPrep ODS-A column at 20 mL/min with a 10 min gradient from 10% CH$_3$CN (0.1% TFA) to 90% CH$_3$CN (0.1% TFA) in H$_2$O (0.1% TFA) and a 2 min hold. Flash chromatography was run over Merck Silica gel 60 (230-400 mesh).

Infrared (IR) spectra were obtained on a Nicolet 510 FT-IR spectrometer using a 1-mm NaCl cell. Most of the reactions were monitored by thin-layer chromatography on 0.25 mm E.

Merck silica gel plates (60F-254), visualized with UV light, 5% ethanolic phosphomolybdic acid or p-anisaldehyde solution.

The following synthetic schemes are merely illustrative of the methods by which the compounds of the invention may be prepared and are not intended to limit the scope of the invention as defined in the appended claims.

The compounds disclosed in Examples 2 to 353 were prepared following the general procedures described in Example 1. The compounds disclosed in Examples 355 to 379 were prepared following the general procedures described in Example 354.

Preparation 1

(4S)-Benzyl-3-heptanoyl-oxazolidin-2-one

To a solution of (S)-(−)-4-benzyl-2-oxazolidinone (3.3 g, 18.6 mmol) in THF (50 mL) at −78° C. was added dropwise n-BuLi (7.4 mL, 2.5M solution in hexane, 18.6 mmol). After stirring for 30 min at the same temperature, the reaction mixture was treated with heptanoyl chloride (2.76 g, 18.6 mmol). The reaction mixture was stirred and allowed to warm to 10° C. over 5 h, and quenched with saturated aqueous NH$_4$Cl solution (100 mL). The aqueous layer was extracted with EtOAc (100 mL×2). The combined organic layers were washed with brine, and dried over MgSO$_4$. Removal of the solvent under reduced pressure yielded 4.63 g (86%) of the title compound. $^1$H NMR (400 MHz, CDCl$_3$) δ 7.37-7.22 (m, 5H), 4.69 (m, 1H), 4.19 (m, 2H), 3.31 (dd, J=13.4, 3.3 Hz, 1H), 2.95 (m, 2H), 2.79 (dd, J=13.4, 9.7 Hz, 1H), 1.71 (m, 2H), 1.42-1.32 (m, 6H), 0.92 (t, J=6.8 Hz, 3H). MH+290.

Preparation 2

(4S)-Benzyl-3-[(2R)-benzyloxymethylheptanoyl] oxazolidin-2-one

To a solution of (S)-4-benzyl-3-heptanoyloxazolidin-2-one (4.63 g, 16.02 mmol) and titanium (IV) chloride (1.9 mL, 16.82 mmol) in dichloromethane (55 mL) at 0° C. was added dropwise diisopropylethylamine (3.1 mL, 17.62 mmol). After stirring at 0° C. for 1 hour, the resulting titanium enolate was reacted with benzylchloromethyl ether (TCI-America, 4.9 mL, 32.04 mmol) at 0° C. for 6 h. The reaction mixture was then quenched with water (100 mL). The aqueous layer was extracted with dichloromethane (100 mL×2). The organic extracts were washed with brine, and dried over MgSO$_4$. After removing the solvent under reduced pressure, purification by flash column chromatography using an eluting system of hexane/EtOAc (5:1) yielded 4.39 g (67%) of the title compound. $^1$H NMR (400 MHz, CDCl$_3$) δ 7.38-7.21 (m, 10H), 4.74 (m, 1H), 4.57 (m, 2H), 4.28-4.13 (m, 3H), 3.82 (t, J=8.7 Hz, 1H), 3.68 (dd, J=9.0, 4.9 Hz, 1H), 3.25 (dd, J=13.5, 3.1 Hz, 1H), 2.71 (dd, J=13.5, 9.3 Hz, 1H), 1.74 (m, 1H), 1.54 (m, 1H), 1.31-1.28 (m, 6H), 0.89 (t, J=6.7 Hz, 3H). MH+410.

Preparation 3

(3R)-Benzyloxy-2-pentylpropionic acid

A 0.05 M solution of (S)-4-benzyl-3-[(R)-2-benzyloxymethylheptanoyl]oxazolidin-2-one (2.0 g, 4.89 mmol) in a 3:1 mixture of THF and H$_2$O was treated with 30% H$_2$O$_2$ (4.5 mL, 39.12 mmol), followed by LiOH (0.48 g, 9.78 mmol) at 0° C. The resulting mixture was stirred and allowed to warm to room temperature overnight. THF was then removed under vacuum. The residue was washed with dichloromethane (50 mL×2) to remove (S)-4-benzyloxazolidin-2-one. The desired product was isolated by EtOAc extraction of the acidified (pH 1~2) aqueous phase. No further purification was required. Standing under high vacuum yielded 1.16 g (95%) of the title compound. $^1$H NMR (400 MHz, CHCl$_3$) δ 11.1 (br s, 1H), 7.36 (m, 5H), 4.57 (s, 2H), 3.69 (m, 1H), 3.58 (dd, J=9.2, 5.2 Hz, 1H), 2.74 (m, 1H), 1.66 (m, 1H), 1.54 (m, 1H), 1.34-1.30 (m, 6H), 0.90 (t, J=6.7 Hz, 3H). MH+251.

Preparation 4

3-Hydroxy-(2R)-pentylpropionic acid

To a solution of (R)-3-benzyloxy-2-pentyl-propionic acid (1.54 g, 6.16 mmol) in EtOH (100 mL) was added 10% Pd/C (310 mg). The reaction mixture was subjected to hydrogenation overnight at room temperature. After the reaction was completed, the reaction mixture was filtered through a pad of Celite, and washed with EtOH (50 mL×3). Removal of the solvent provided the title compound (0.92 g, 93%). No further purification was required. $^1$H NMR (400 MHz, CHCl$_3$) δ 6.30 (br s, 1H), 3.81 (d, J=5.4 Hz, 2H), 2.64 (m, 1H), 1.69 (m, 1H), 1.56 (m, 1H), 1.41-1.27 (m, 6H), 0.91 (t, J=7.7 Hz, 3H). MH+161.

Preparation 5

N-Benzyloxy-3-hydroxy-(2R)-pentylpropionamide

To a mixture of (R)-3-hydroxy-2-pentylpropionic acid (0.92 g, 5.75 mmol), O-benzyl hydroxylamine hydrochloride (0.92 g, 5.75 mmol) and 4-(dimethylamino)pyridine (1.41 g, 11.50 mmol) in dichloromethane (25 mL) at 0° C. was added 1-[3-(dimethylamino)propyl]-3-ethylcarbodiimide hydrochloride (1.11 g, 5.75 mmol). After stirring at room temperature overnight, the reaction was quenched with 1N aqueous HCl solution (25 mL) and extracted using dichloromethane (25 mL×2). The organic extracts were washed with water, brine, and dried over MgSO$_4$. Removal of the solvent under reduced. pressure yielded the title compound (1.43 g, 94%). $^1$H NMR (400 MHz, CHCl$_3$) δ 9.22 (br s, 1H), 7.41-7.28 (m, 5H), 4.89 (q, J=10.6 Hz, 2H), 3.70-3.37 (m, 3H), 2.17 (m, 1H), 1.54 (br s, 1H), 1.27 (m, 6H), 0.88.(t, J=6.9 Hz, 3H). MH+266.

Preparation 6

1-benzyloxy-(3R)-pentylazetidin-2-one

To a mixture of (R)-N-benzyloxy-3-hydroxy-2-pentylpropionamide (1.41 g, 5.32 mmol) and triphenylphosphine (1.68 g, 6.39 mmol) in THF (53 mL) was added dropwise diethyl azodicarboxylate (1.1 mL, 6.39 mmol) at 0° C. The reaction mixture was stirred and allowed to warm to room temperature overnight. The reaction was then quenched with water (50 mL). The aqueous layer was extracted with EtOAc (50 mL×2). The combined organic layers were washed with brine, and dried over MgSO$_4$. After removing the solvent under vacuum, the residue was purified by flash column chromatography (hex:EtOAc 5/1) to provide the title compound (1.17 g, 89%). $^1$H NMR (400 MHz, CHCl$_3$) δ 7.35-7.25 (m, 5H), 4.87 (s, 2H), 3.28 (t, J=4.85 Hx, 1H), 2.84 (q, J 2.35 Hz, 1H), 2.77 (m, 1H), 1.62 (m, 1H), 1.36 (m, 1H), 1.25-1.16 (m, 6H), 0.88 (t, J=6.9 Hz, 3H). MH+248.

Preparation 7

3-benzyloxyamino-(2R)-pentylpropionic acid

To a solution of (R)-1-benzyloxy-3-pentylazetidin-2-one (0.96 g, 3.89 mmol) in a mixture of THF-$H_2O$-MeOH (50 mL, 3:1:1 v/v) was added lithium hydroxide monohydrate (1.91 g, 38.9 mmol). After stirring at room temperature overnight, water (25 mL) was added to the mixture. The solution was acidified to pH 5~6 with 3N aqueous HCl solution. It was extracted with EtOAc (50 mL×2). The combined organic layers were dried over $MgSO_4$. Removal of the solvent under vacuum provided the title compound (0.98 g, 95%). $^1H$ NMR (400 MHz, $CHCl_3$) δ 9.80 (br s, 1H), 7.37 (m, 5H), 4.75 (m, 2H), 3.14 (m, 2H), 2.74 (m, 1H), 1.70 (m, 1H), 1.53 (m, 1H), 1.38-1.25 (m, 6H), 0.91 (t, J=6.8 Hz, 3H). MH+266.

Preparation 8

(2R)-[(benzyloxyformylamino)methyl]heptanoic acid

To a cold solution of (R)-3-benzyloxyamino-2-pentylpropionic acid (1.03 g, 3.89 mmol) in $HCO_2H$ (19 mL) and dichloromethane (19 mL) at 0° C. was added acetic anhydride (3.9 mL, 41.2 mmol). The mixture was stirred at 0° C. for 3 hours. The volatiles were removed by evaporation under vacuum. Dichloromethane (50 mL) was added. The organic solution was washed with brine (50 mL×2), and dried over $MgSO_4$. Filtration and evaporation under vacuum provided the title compound (1.08 g, 95%). $^1H$ NMR (400 MHz, $CHCl_3$) δ 8.07 (br s, 1H), 7.29 (m, 5H), 4.91-4.71 (m, 2H), 3.76 (m, 2H), 2.67 (m, 1H), 1.54 (m, 1H), 1.41(m, 1H), 1.20 (m, 6H), 0.80 (t, J=7.0 Hz, 3H). MH+294.

Example 1

N-Hydroxy-N-[(R)-2-(N'-pyridin-2-yl-hydrazinocarbonyl)-heptyl]-formamide (2R)-[(benzyloxyformylamino)methyl]heptanoic acid (1.2 mmoles), HOAt (1.3 mmoles), N'-pyridin-2-yl-hydrazine (1.2 mmoles) and NMM (5 mmoles) were dissolved in DMF and treated with EDCI (1.3 mmoles) at room temperature for 12 hours. The coupling product N-benzyloxy-N-[(R)-2-(N'-pyridin-2-yl-hydrazinocarbonyl)-heptyl]-formamide was isolated by prep hplc of the crude reaction mixture. This compound was submitted to atmospheric pressure hydrogenation over Pd/C in methanol for 1 hour, yielding the title compound. MH+295.

Preparation 9

2-Hydrazino-5-ethylpyrimidine

To a solution of 2-chloro-5-ethylpyrimidine (0.31 g, 2.2 mmol) in MeOH (5 mL) was added hydrazine monohydrate (1.0 mL, 20.6 mmol). After stirring for 16 h at 50° C., the solution was cooled to room temperature and purified by reverse phase HPLC to give 0.24 g (80%) of the title compound as a white solid. MH+139.

Preparation 10

2-Hydrazino-4-methylpyrimidine

To a finely dispersed suspension of 2-chloropyrimidine (8.01 g, 69.9 mmol) in a 10:1 mixture of $Et_2O$-THF (500 mL) at −30° C. was added dropwise MeLi (46 mL, 1.6M in $Et_2O$, 73.6 mmol). The reaction mixture was stirred at −30° C. for 30 min, and was then warmed to 0° C. and stirred for 30 min. To the reaction mixture was then added a 1:1:20 mixture of $H_2O$—HOAc-THF (100 mL), and the mixture was stirred at 0° C. for 10 min. To the mixture was then added a solution of DDQ (16.7 g, 73.6 mmol) in THF (100 mL), and the mixture was stirred and warmed to room temperature for 30 min. The mixture was then diluted with $Et_2O$ (300 mL) and washed with 1N aq. NaOH (3×100 mL) followed by brine (300 mL). The organic phase was then dried over anhydrous $MgSO_4$, filtered, concentrated in vacuo, and purified by flash chromatography using EtOAc-hexanes (1:2) as eluent to afford 6.06 g of 2-chloro-4-methylpyrimidine (67%) as white crystalline plates.

To a solution of 2-chloro-4-methylpyrimidine (6.06 g, 47.1 mmol) in MeOH (40 mL) was added hydrazine monohydrate (10 mL, 206 mmol). The solution was stirred for 16 h at room temperature and then purified by reverse phase HPLC to provide 4.43 g of the title compound. (76%) as a white solid. MH+125.

Preparation 11

2-Hydrazino-4-morpholino-6-methylpyrimidine

To a solution of 2,4-dichloro-6-methylpyrimidine (0.41 g, 2.50 mmol) in MeOH (5 mL) was added morpholine (0.5 mL, 5.73 mmol). The solution was stirred for 30 min at room temperature, and then hydrazine monohydrate (1.0 mL, 20.6 mmol) was added. The solution was then heated at 60° C. and stirred for 16 h. The solution was then cooled to room temperature and purified by reverse phase HPLC to afford 0.31 g of the title compound (59%) as a waxy white solid. MH+210.

Preparation 12

2-Hydrazino-4-(2,3,4-trimethoxyphenyl)pyrimidine

To a solution of 2-thiomethyl-4-chloropyrimidine (0.3410 g, 2.12 mmol) in 1,4-dioxane (21 mL) was added 2,3,4-trimethoxyphenylboronic acid (0.4950 g, 2.33 mmol) and aq. $Na_2CO_3$ (2.3 mL, 2.0M in water, 4.60 mmol). The mixture was sparged with dry nitrogen gas for 5 min, and then $Pd(Ph_3P)_4$ (123 mg, 0.106 mmol) was added. The mixture was protected from light and heated at 110° C. for 16 h. The mixture was then cooled to room temperature, filtered, concentrated in vacuo, and purified by flash chromatography using EtOAc-hexanes (1:4) as eluent to give 0.5920 g of 2-thiomethyl-4-(2,3,4-trimethoxyphenyl)pyrimidine (95%) as a yellow solid.

To a solution of 2-thiomethyl-4-(2,3,4-trimethoxyphenyl) pyrimidine (0.5920 g, 2.02 mmol) in $CH_2Cl_2$ (10 mL) was added m-chloroperbenzoic acid (1.05 g, 6.08 mmol), and the solution was stirred for 3 h at which time it was observed to be a white suspension. The suspension was concentrated in vacuo, and MeOH (10 mL) was added followed by hydrazine monohydrate (2 mL, 41.2 mmol). The resulting solution was stirred for 16 h and then concentrated to about one-half volume in vacuo. The mixture was allowed to stand for 1 h, and the resulting solid was collected by vacuum filtration and was washed with water. Drying in vacuo afforded 0.3330 g of the title compound (60%) as a light brown solid. MH+277.

Preparation 13

2-Hydrazino-4-morpholino-6-trifluoromethylpyrimidine

To a solution of 2-thiomethyl-4-chloro-6-trifluoromethylpyrimidine (1.9996 g, 8.75 mmol) in MeOH (50 mL) was added morpholine (1.5 mL, 17.2 mmol). The solution was stirred overnight, concentrated in vacuo, and the resulting white solid was collected by vacuum filtration and washed with water. To a solution of the solid in $CH_2Cl_2$ (50 mL) was added m-chloroperbenzoic acid (4.53 g, 26.3 mmol), and the resulting solution was stirred for 2 h at which time it was observed to be a white suspension. The solvent was removed in vacuo, and then MeOH (50 mL) was added followed by hydrazine monohydrate (3.0 mL, 61.8 mmol). The solution was stirred for 16 h, and was then concentrated to about one-half volume in vacuo. Water (100 mL) was then added to the resulting suspension, and the observed white solid was collected by vacuum filtration. This material was then washed with water and dried in vacuo to afford 1.7193 g of the title compound (75%) as a white solid. MH+264.

Preparation 14

2-Hydrazino-5,6,7,8-tetrahydroquinazoline

To a mixture of ethyl 2-cyclohexanonecarboxylate (3.00 g, 17.6 mmol) and 2-methyl-2-thiopseudourea sulfate (3.68 g, 13.2 mmol) was added a solution of potassium carbonate (7.31 g, 52.9 mmol) in water (60 mL). The reaction solution was stirred at room temperature for 16 h, at which time it was observed to be a suspension. The white solid was collected by vacuum filtration, washed with water, and dried in vacuo. A mixture of the solid in phosphorus oxychloride (20 mL) was heated at 110° C. in a sealed tube, at which time it was observed to be a solution. The solution was cooled to room temperature and was then poured over cracked ice and water (300 mL). The mixture was vigorously stirred at 0° C. for 1 h, and the resulting precipitate was collected by vacuum filtration, washed with water, and dried in vacuo to afford 1.61 g of 2-thiomethyl-4-chloro-5,6,7,8-tetrahydroquinazoline (43%) as an off-white solid. To a solution of 2-thiomethyl-4-chloro-5,6,7,8-tetrahydroquinazoline (0.5121 g, 2.39 mmol) in a 10:1 mixture of MeOH—HOAc (30 mL) was added activated zinc dust (500 mg, 7.65 mmol). The mixture was heated at 70° C. for 1 h, and was then cooled to room temperature and filtered. The resulting solution was concentrated in vacuo, and azeotropically dried with toluene (50 mL). The residue was partitioned between EtOAc (150 mL) and 1 N aq. HCl (50 mL), and the organic phase was then washed with saturated aq. $NaHCO_3$ and brine. The organic phase was then dried over anhydrous $MgSO_4$ and concentrated in vacuo to provide 0.1461 g of 2-thiomethyl-5,6,7,8-tetrahydroquinazoline (34%) as a purple oil. To a solution of 2-thiomethyl-5,6,7,8-tetrahydroquinazoline (0.1461 g, 0.81 mmol) in $CH_2Cl_2$ (5 mL) was added m-chloroperbenzoic acid (0.462 g, 2.68 mmol). The solution was stirred at room temperature for 3 h at which time it was observed to be a suspension. The solvent was then removed in vacuo, and MeOH (5 mL) was added followed by hydrazine monohydrate (1 mL, 20.6 mmol). The solution was then heated at 50° C. and stirred for 16 h. The solution was cooled to room temperature and purified by reverse phase HPLC to give 0.1126 g of the title compound (85%) as a colorless oil. MH+165.

Preparation 15

2-Hydrazino-4-(2-pyridyl)pyrimidine

To a solution of 2-amino-4-(2-pyridyl)pyrimidine (10.10 g, 58.66 mmol) in 5% aqueous sulfuric acid (200 mL) was added sodium nitrate (20.24 g, 293.3 mmol) portionwise over 10 min. The solution was stirred at room temperature for 2 h and was then adjusted to pH 10 by addition of 6N aq. NaOH. The resulting mixture was then extracted with 30% i-PrOH in $CHCl_3$ (10×300 mL), and the combined organic phase was dried over anhydrous $MgSO_4$ and concentrated in vacuo. The residue was triturated with hexanes and collected by vacuum filtration to afford 6.89 g of 4-(2-pyridyl)pyrimid-2-one (68%) as a beige solid. A mixture of 4-(2-pyridyl)pyrimid-2-one (6.89 g, 39.8 mmol) in phosphorus oxychloride (30 mL) was heated at 110° C. for 90 min in a sealed tube. The dark brown solution was then cooled to room temperature and poured over cracked ice and water (500 mL). The mixture was vigorously stirred at 0° C. for 1 h, and was then adjusted to pH 14 with 6 N aq NaOH. The mixture was extracted with $CH_2Cl_2$ (2×300 mL), and the combined organic phase was dried over anhydrous $MgSO_4$ and concentrated in vacuo. To a solution of the residue in $CH_2Cl_2$ (10 mL) and MeOH (30 mL) was added hydrazine monohydrate (7.0 mL, 144.2 mmol), and the solution was stirred for 16 h at which time a white precipitate was observed. This solid was collected by vacuum filtration, washed with water, and dried in vacuo to provide 2.20 g of the title compound (30%) as an off-white solid. MH+188.

Preparation 16

(6-Morpholin-4-yl-pyrimidin-4-yl)-hydrazine

A solution of 4,6 dichloropyrimidine (300 mg, 2 mmol), tert-butyl carbazate (280 mg, 2.1 mmol) and Hunig's base (453 µL, 2.6 mmol) in ethanol (3 ml) was stirred at 120° C. for 1 hour under microwave condition. After morpholine (700 µL, 8 mmol) was added, the mixture was then resubmitted to the same microwave condition for another hour. Evaporation of solvent under vacuum gave a white solid which was treated with TFA (3 ml) in DCM (3 ml) for 20 min. After evaporation of solvent, the residue was redissolved in methanol. Treatment with solid $NaHCO_3$ removed the traces of TFA that might have been left over. Filtration followed by evaporation of the solvent gave a residue which was submitted to reverse-phase HPLC purification to produce (6-morpholin-4-yl-pyrimidin-4-yl)-hydrazine (200 mg, 1 mmol, 50% in 3 steps) as a white solid. MH+196. Alternatively, the same compound may be generated by stirring a solution of 4,6 dichloropyrimidine (300 mg, 2 mmol), morpholine (280 mg, 2.1 mmol) and diisopropylethylamine (453 µL, 2.6 mmol) in ethanol (3 ml) for one hour. After addition of hydrazine (370 µL, 6 mmol), the mixture was stirred at 120° C. for 1 hour under microwave condition. After evaporation of the solvent, the compound was dissolved in DMSO before submitted to prep HPLC purificaton which then gave 6-morpholin-4-yl-pyrimidin-4-yl)-hydrazine. MH+196.

Preparation 17

(2-Ethylamine-6-trifluoromethyl-pyrimidin-4-yl)-hydrazine

A solution of (4-chloro-6-trifluoromethyl-pyrimidin-2-yl)-ethyl-amine (100 mg, 0.38 mmol), hydrazine (87 µL, 3.8 mmol) in ethanol was heated at 70° C. over night. Evaporation of the solvent under vacuum gave a residue which was purified by prep HPLC to give (2-ethylamine-6-trifluoromethyl-pyrimidin-4-yl)-hydrazine (74 mg, 75%). MH+256.

Preparation 18

[(4-Methyl-piperazin-1-yl)-trifluoromethyl-pyrimidin-4-yl]-hydrazine

A mixture of 4-chloro-2-methylthiol-6-(trifluomethyl)pyrimidine (228 mg, 1 mmol), tert-butyl carbazate (159 mg. 6, 1.2 mmol) in ethanol was heated to 100° C. in the microwave reactor for 20 min. Evaporation of solvent gave a white solid. The solid was treated with MCPBA in DCM at rt overnight. Evaporation of the solvent gave a white solid which was treated with 1-methylpiperazine at 140° C. for 20 min. in ethanol under microwave conditions. Evaporation of solvents gave a solid which was treated TFA (3 ml) in DCM (3 ml) for 20 min. After the reaction was done, most of TFA and DCM was removed under vacuum. The residue was redissolved in methanol and treated with solid NaHCO$_3$ to remove TFA residue until no gas was generated. Filtration and vacuum evaporation of the filtrate gave a residue which was purified by prep. HPLC to give [(4-Methyl-piperazin-1-yl)-trifluoromethyl-pyrimidin-4-yl]-hydrazine (100 mg, 36%). MH+277.

Example 2

N-Hydroxy-N-{(R)-2-[N'-(3-methoxy-phenyl)-hydrazinocarbonyl]-heptyl}-formamide

MH+=324.

Example 3

N-Hydroxy-N-{(R)-2-[N'-(4-trifluoromethyl-pyrimidin-2-yl)-hydrazinocarbonyl]-heptyl}-formamide

MH+=364.

Example 4

N-{(R)-2-[N'-(4-Cyano-phenyl)-hydrazinocarbonyl]-heptyl}-N-hydroxy-formamide

MH+=319.

Example 5

N-{(R)-2-[N'-(2,6-Dimethyl-pyrimidin-4-yl)-hydrazinocarbonyl]-heptyl}-N-hydroxy-formamide

MH+=324.

Example 6

N-Hydroxy-N-[(R)-2-(N'-quinoxalin-2-yl-hydrazinocarbonyl)-heptyl]-formamide

MH+=346.

Example 7

N-Hydroxy-N-((2R)-2-{N'-(3,4-dihydro-quinoxalin-2-yl)-hydrazinocarbonyl}-heptyl)-formamide

MH+=348.

Example 8

N-Hydroxy-N-{(R)-2-[N'-(1,3,4-trimethyl-1H-pyrazolo[3,4-b]pyridin-6-yl)-hydrazinocarbonyl]-heptyl}-formamide

MH+=377.

Example 9

4-(N'-{(R)-2-[(Formyl-hydroxy-amino)-methyl]-heptanoyl}-hydrazino)-benzenesulfonamide

MH+=373.

Example 10

N-Hydroxy-N-[(2R)-2-(cyclohexylmethyl)-3-oxo-3-{N'-[4-(trifluoromethyl)-pyrimidin-2-yl]-hydrazino}-propyl]-formamide

MH+=390.

Example 11

N-Hydroxy-N-[(2R)-2-(cyclopentylmethyl)-3-oxo-3-{N'-[4-(trifluoromethyl)-pyrimidin-2-yl]-hydrazino}-propyl]-formamide

MH+=376.

Example 12

N-{(R)-2-[N'-(Dimethyl-trifluoromethyl-pyrimidin-4-yl)-hydrazinocarbonyl]-heptyl}-N-hydroxy-formamide

MH+=392.

Example 13

N-Hydroxy-N-{(R)-2[N'-(6-trifluoromethyl-pyridazin-3-yl)-hydrazinocarbonyl]-heptyl}-formamide

MH+=364.

Example 14

N-Hydroxy-N-{(R)-2-[N'-(6-trifluoromethyl-pyrimidin-4-yl)-hydrazinocarbonyl]-heptyl}-formamide

MH+=364.

Example 15

N-Hydroxy-N-{(R)-2-[N'-(5-methyl-[1,2,4]triazolo[1,5-a]pyrimidin-7-yl)-hydrazinocarbonyl]-heptyl}-formamide

MH+=350.

Example 16

N-Hydroxy-N-{(R)-2-[N'-(9H-purin-6-yl)-hydrazinocarbonyl]-heptyl}-formamide

MH+=336.

Example 17

N-{(R)-2-[N'-(5-Cyano-pyrimidin-2-yl)-hydrazinocarbonyl]heptyl}-N-hydroxy-formamide

MH+=321.

Example 18

N-Hydroxy-N-((2R)-2-{[N'-(pyrimidin-2-yl)-hydrazino]carbonyl}-heptyl)-formamide

MH+=296.

Example 19

N-Hydroxy-N-((2R)-2-(cyclobutylmethyl)-3-oxo-3-{N'-[4-(trifluoromethyl)-pyrimidin-2-yl]-hydrazino}-propyl)-formamide

MH+=362.

Example 20

N-Hydroxy-N-{(R)-2-[N'-(6-imidazol-1-yl-pyrimidin-4-yl)-hydrazinocarbonyl]-heptyl}-formamide

MH+=362.

Example 21

N-[(R)-2-(N'-Benzo[1,2,4]triazin-3-yl-hydrazinocarbonyl)-heptyl]-N-hydroxy-formamide

MH+=347.

Example 22

N-Hydroxy-N-{(R)-2-[N'-(7-methoxy-benzo[1,2,4]triazin-3-yl)-hydrazinocarbonyl]-heptyl}-formamide

MH+=377.

Example 23

N-Hydroxy-N-{(R)-2-[N'-(1-methyl-1H-pyrazolo[3,4-d]pyrimidin-6-yl)-hydrazinocarbonyl]-heptyl}-formamide

MH+=350.

Example 24

N-((R)-2-{N'-[6-(5-Chloro-pyridin-3-yl-oxy)-pyridazin-3-yl]-hydrazinocarbonyl}-heptyl)-N-hydroxy-formamide

MH+=423.

Example 25

N-Hydroxy-N-[(2R)-2-({N'-[6-(1H-pyrrol-1-yl)-3-pyridaznyl]-hydrazino}-carbonyl)-heptyl]-formamide

MH+=361.

Example 26

N-Hydroxy-N-((2R)-2-{[N'-(9-methyl-9H-purin-6-yl)-hydrazino]-carbonyl}-heptyl)-formamide

MH+=350.

Example 27

N-Hydroxy-N-{(R)-2-[N-({6-morpholin-4-yl}-9H-purin-2-yl)-hydrazinocarbonyl]-heptyl}-formamide

MH+=421.

Example 28

N-{(R)-2-[N'-(6-Fluoro-pyridin-2-yl)-hydrazinocarbonyl]-heptyl}-N-hydroxy-formamide

MH+=313.

Example 29

N-Hydroxy-N-((2R)-2-{[N'-(1-methyl-1H-pyrazolo[3,4-d]pyrimidin-4-yl)-hydrazino]-carbonyl}-heptyl)-formamide

MH+=350.

Example 30

N-{(R)-2-[N'-(4-Amino-6-isopropyl-[1,3,5]triazin-2-yl)-hydrazinocarbonyl]-heptyl}-N-hydroxy-formamide

MH+=354.

Example 31

N-{(R)-2-[N'-(2,5-Dimethyl-4-nitro-2H-pyrazol-3-yl)-hydrazinocarbonyl]-heptyl}-N-hydroxy-formamide

MH+=357.

Example 32

N-{(R)-2-[N'-(3-Chloro-1-methyl-1H-pyrazolo[3,4-d]pyrimidin-6-yl)-hydrazinocarbonyl]-heptyl}-N-hydroxy-formamide

MH+=384.

Example 33

N-{(R)-2-[N'-(6-Dimethylamino-9H-purin-2-yl)-hydrazinocarbonyl]-heptyl}-N-hydroxy-formamide

MH+=379.

Example 34

N-Hydroxy-N-[(2R)-4-cyclopropyl-2-({N'-[4-(trifluoromethyl)-pyrimidin-2-yl]-hydrazino}-carbonyl)-butyl]-formamide

MH+=362.

Example 35

N-Hydroxy-N-((2R)-2-(cyclopropylmethyl)-3-oxo-3-{N'-[4-(trifluoromethyl)-pyrimidin-2-yl]-hydrazino}-propyl)-formamide

MH+=348.

Example 36

N-Hydroxy-N-{(R)-2-[N'-methyl-N'-(4-trifluoromethyl-pyrimidin-2-yl)-hydrazinocarbonyl]-heptyl}-formamide

MH+=378.

Example 37

2-(N'-{(R)-2-[(Formyl-hydroxy-amino)-methyl]-heptanoyl}-hydrazino)-4-trifluoromethyl-pyrimidine-5-carboxylic acid methyl ester

MH+=422.

Example 38

2-(N'-{(R)-2-[(Formyl-hydroxy-amino)-methyl]-heptanoyl}-hydrazino)-4-trifluoromethyl-pyrimidine-5-carboxylic acid

MH+=408.

Example 39

N-{(R)-2-[N'-(5-Fluoro-4-methoxy-pyrimidin-2-yl)-hydrazinocarbonyl]-heptyl}-N-hydroxy-formamide

MH+=344.

Example 40

N-{(R)-2-[N'-(4-Dimethylamino-pyrimidin-2-yl)-hydrazinocarbonyl]-heptyl}-N-hydroxy-formamide

MH+=339.

Example 41

N-Hydroxy-N{(2R)-2-[(N'-{6-[(2-hydroxyethyl)amino]-1,3-dihydro-2H-purin-2-ylidene}-hydrazino)-carbonyl]-heptyl}-formamide

MH+=395.

Example 42

N-{(R)-2-[N'-(5-Fluoro-4-morpholin-4-yl-pyrimidin-2-yl)-hydrazinocarbonyl]-heptyl}-N-hydroxy-formamide

MH+=399.

Example 43

N-{(R)-2-[N'-(5-Fluoro-4-methylamino-pyrimidin-2-yl)-hydrazinocarbonyl]-heptyl}-N-hydroxy-formamide

MH+=343.

Example 44

2-(N'-{(R)-2-[(Formyl-hydroxy-amino)-methyl]-heptanoyl}-hydrazino)-4-trifluoromethyl-pyrimidine-5-carboxylic acid dimethylamide

MH+=435.

Example 45

N-Hydroxy-N-{(R)-2-[N'-(3-oxo-3,4-dihydro-quinoxalin-2-yl)-hydrazinocarbonyl]-heptyl}-formamide

MH+=362.

Example 46

N-{(R)-2-Butoxy-2-[N'-(4-trifluoromethyl-pyrimidin-2-yl)-hydrazinocarbonyl]-ethyl}-N-hydroxy-formamide

MH+=366.

Example 47

2-(N'-{(R)-2-[(Formyl-hydroxy-amino)-methyl]-heptanoyl}-hydrazino)-4-trifluoromethyl-pyrimidine-5-carboxylic acid (2-fluoro-phenyl)-amide

MH+=501.

Example 48

2-(N'-{(R)-2-[(Formyl-hydroxy-amino)-methyl]-heptanoyl}-hydrazino)-4-trifluoromethyl-pyrimidine-5-carboxylic acid tert-butylamide

MH+=463.

Example 49

N-Hydroxy-N-((R)-2-{N'-[(1-piperidin-1-yl-methanoyl)-trifluoromethyl-pyrimidin-2-yl]-hydrazinocarbonyl}-heptyl)-formamide

MH+=475.

Example 50

N-{(R)-2-[N'-(5-Cyano-4-trifluoromethyl-pyrimidin-2-yl)-hydrazinocarbonyl]-heptyl}-N-hydroxy-formamide

MH+=389.

Example 51

N-Hydroxy-N-[(2R)-2-({N'-[9-(4,4,4-trifluorobutyl)-1,9-dihydro-2H-purin-2-ylidene]-hydrazino}-carbonyl)-heptyl]-formamide

MH+=446.

Example 52

N-Hydroxy-N-((R)-2-{N'-[(1-morpholin-4-yl-methanoyl)-trifluoromethyl-pyrimidin-2-yl]-hydrazinocarbonyl}-heptyl)-formamide

MH+=477.

Example 53

2-(N'-{(R)-2-[(Formyl-hydroxy-amino)-methyl]-heptanoyl}-hydrazino)-4-trifluoromethyl-pyrimidine-5-carboxylic acid benzylamide

MH+=497.

Example 54

N-Hydroxy-N-[(2R)-3-[N'-(1,2,4-benzotriazin-3-yl)-hydrazino]-2-(cyclohexylmethyl)-3-oxopropyl]-formamide

MH+=373.

Example 55

N-Hydroxy-N-((2R)-2-(cyclohexylmethyl)-3-{N'-[7-(methyloxy)-1,2,4-benzotriazin-3-yl]-hydrazino}-3-oxopropyl)-formamide

MH+=403.

Example 56

2-[2-((2R)-2-{[Formyl(hydroxy)amino]methyl}heptanoyl)hydrazino]-N-methyl-N-2-pyridinyl-4-(trifluoromethyl)-5-pyrimidinecarboxamide

MH+=498.

Example 57

2-[2-((2R)-2-{[Formyl(hydroxy)amino]methyl}heptanoyl)hydrazino]-N-methyl-N-phenyl-4-(trifluoromethyl)-5-pyrimidinecarboxamide

MH+=497.

Example 58

2-(N'-{(R)-2-[(Formyl-hydroxy-amino)-methyl]-heptanoyl}-hydrazino)-4-trifluoromethyl-pyrimidine-5-carboxylic acid morpholin-4-ylamide

MH+=492.

Example 59

N-Hydroxy-N-((R)-2-{N'-[(N'-phenyl-hydrazinocarbonyl)-trifluoromethyl-pyrimidin-2-yl]-hydrazinocarbonyl}-heptyl)-formamide

MH+=498.

Example 60

2-(N'-{(R)-2-[(Formyl-hydroxy-amino)-methyl]-heptanoyl}-hydrazino)-4-trifluoromethyl-pyrimidine-5-carboxylic acid piperidin-1-ylamide

MH+=490.

Example 61

2-(N'-{(R)-2-[(Formyl-hydroxy-amino)-methyl]-heptanoyl}-hydrazino)-4-trifluoromethyl-pyrimidine-5-carboxylic acid pyrrol-1-ylamide

MH+=472.

Example 62

N-{(R)-2-[N'-(Dimethylamino-fluoro-pyrimidin-2-yl)-hydrazinocarbonyl]-heptyl}-N-hydroxy-formamide

MH+=357.

Example 63

N-((R)-2-{N'-[(Ethyl-methyl-amino)-fluoro-pyrimidin-2-yl]-hydrazinocarbonyl}-heptyl)-N-hydroxy-formamide

MH+=371.

Example 64

N-Hydroxy-N-((2R)-2-(cyclopentylmethyl)-3-{N'-[7-(methyloxy)-1,2,4-benzotriazin-3-yl]-hydrazino}-3-oxopropyl)-formamide

MH+=389.

Example 65

N-Hydroxy-N-{(R)-2-[N'-(1-methyl-1H-benzoimidazol-2-yl)-hydrazinocarbonyl]-heptyl}-formamide

MH+=348.

Example 66

N-{(R)-2-[N'-(4-Azetidin-1-yl-5-fluoro-pyrimidin-2-yl)-hydrazinocarbonyl]-heptyl}-N-hydroxy-formamide

MH+=369.

Example 67

N-{(R)-2-[N'-(4-Cyclopropylamino-5-fluoro-pyrimidin-2-yl)-hydrazinocarbonyl]-heptyl}-N-hydroxy-formamide

MH+=369.

Example 68

N-[(R)-2-(N-Benzo[1,2,4]triazin-3-yl-hydrazinocarbonyl)-3-cyclopentyl-propyl]-N-hydroxy-formamide

MH+=359.

Example 69

N-Hydroxy-N-{(R)-2-[N'-(morpholin-4-yl-trifluoromethyl-pyrimidin-2-yl)-hydrazinocarbonyl]-heptyl}-formamide

MH+=449.

Example 70

N-Hydroxy-N-[(R)-2-(N'-{[(2-hydroxy-ethyl)-methyl-amino]-trifluoromethyl-pyrimidin-2-yl}-hydrazinocarbonyl)-heptyl]-formamide

MH+=437.

Example 71

N-Hydroxy-N-((R)-2-{N'-[(4-methyl-piperazin-1-yl)-trifluoromethyl-pyrimidin-2-yl]-hydrazinocarbonyl}-heptyl)-formamide

MH+=462.

Example 72

N-Hydroxy-N-((2R)-2-(cyclohexylmethyl)-3-{N'-[4-(cyclopropylamino)-5-fluoro-pyrimidin-2-yl]hydrazino}-3-oxopropyl)-formamide

MH+=395.

Example 73

N-Hydroxy-N-((2R)-2-(cyclopentylmethyl)-3-{N'-[4-(cyclopropylamino)-5-fluoro-pyrimidin-2-yl]hydrazino}-3-oxopropyl)-formamide

MH+=381.

Example 74

N-Hydroxy-N-[(2R)-3-{N'-[4-(azetidin-1-yl)-5-fluoro-pyrimidin-2-yl]-hydrazino}-2-(cyclopentylmethyl)-3-oxopropyl]-formamide

MH+=381.

Example 75

N-Hydroxy-N-[(2R)-5-methyl-2-({N'-[4-(trifluoromethyl)-pyrimidin-2-yl]-hydrazino}-carbonyl)-hexyl]-formamide

MH+=364.

Example 76

N-[(R)-2-(N'-Benzo[1,2,4]triazin-3-yl-hydrazinocarbonyl)-5methyl-hexyl]-N-hydroxy-formamide

MH+=347.

Example 77

N-Hydroxy-N-[(2R)-5-methyl-2-({N'-[7-(methyloxy)-1,2,4-benzotriazin-3-yl]-hydrazino}-carbonyl)-hexyl]-formamide

MH+=377.

Example 78

N-{(R)-2-[N'-(7-Chloro-benzo[1,2,4]triazin-3-yl)-hydrazinocarbonyl]-heptyl}-N-hydroxy-formamide

MH+=381.

Example 79

N-Hydroxy-N-((2R)-2-(cyclopentylmethyl)-3-{N'-[4-(morpholin-4-yl)-6-(trifluoromethyl)-pyrimidin-2-yl]-hydrazino}-3-oxopropyl)-formamide

MH+=461.

Example 80

N-Hydroxy-N-((2R)-2-(cyclopentylmethyl)-3-{N'-[4-[(2-hydroxyethyl)-(methyl)-amino]-6-(trifluoromethyl)-pyrimidin-2-yl]-hydrazino}-3-oxopropyl)-formamide

MH+=449.

Example 81

N-Hydroxy-N-[(2R)-6-methyl-2-({N'-[4-(trifluoromethyl)-pyrimidin-2-yl]-hydrazino}-carbonyl)-heptyl]-formamide

MH+=378.

Example 82

N-Hydroxy-N-((2R)-2-{[N'-(1,2,4-benzotriazin-3-yl)-hydrazino]-carbonyl}-6-methylheptyl)-formamide

MH+=361.

Example 83

N-Hydroxy-N-{(R)-2-[N'-(5-methyl-benzo[1,2,4]triazin-3-yl)-hydrazinocarbonyl]-heptyl}-formamide

MH+=361.

Example 84

N-((R)-2-{N'-[(4-Ethyl-piperazin-1-yl)-trifluoromethyl-pyrimidin-2-yl]-hydrazinocarbonyl}-heptyl)-N-hydroxy-formamide

MH+=476.

Example 85

N-Hydroxy-N-{(R)-2-[N'-(piperazin-1-yl-trifluoromethyl-pyrimidin-2-yl)-hydrazinocarbonyl]-heptyl}-formamide

MH+=448.

Example 86

N-{(R)-2-[N'-(7-Fluoro-benzo[1,2,4]triazin-3-yl)-hydrazinocarbonyl]-heptyl}-N-hydroxy-formamide

MH+=365.

Example 87

N-Hydroxy-N-[(2R)-2-({N'-[4-(4-ethyl-1-piperazinyl)-6-(trifluoromethyl)-pyrimidin-2-yl]-hydrazino}-carbonyl)-6-methylheptyl]-formamide

MH+=490.

Example 88

N-Hydroxy-N-[(2R)-6-methyl-2-({N'-[4-(piperazin-1-yl)-6-(trifluoromethyl)-pyrimidin-2-yl]-hydrazino}-carbonyl)-heptyl]-formamide

MH+=462.

Example 89

N-Hydroxy-N-[(2R)-6-methyl-2-({N'-[4-(4-methyl-piperazin-1-yl)-6-(trifluoromethyl)-pyrimidin-2-yl]-hydrazino}-carbonyl)-heptyl]-formamide

MH+=476.

Example 90

N-Hydroxy-N-((2R)-2-{[N'-(7-chloro-1,2,4-benzotriazin-3-yl)hydrazino]carbonyl}-6-methylheptyl)-formamide

MH+=395.

Example 91

N-Hydroxy-N-((2R)-6-methyl-2-{[N'-(5-methyl-1,2,4-benzotriazin-3-yl)-hydrazino]-carbonyl}-heptyl)-formamide

MH+=375.

Example 92

N-Hydroxy-N-((2R)-2-{[N'-(7-fluoro-1,2,4-benzotriazin-3-yl)-hydrazino]-carbonyl}-6-methylheptyl)-formamide

MH+=379.

Example 93

N-Hydroxy-N-((R)-2-{N'-[(2-methoxy-ethylamino)-trifluoromethyl-pyrimidin-2-yl]-hydrazinocarbonyl}-heptyl)-formamide

MH+=437.

Example 94

N-Hydroxy-N-[(2R)-6-methyl-2-({N'-[7-(methyloxy)-1,2,4-benzotriazin-3-yl]-hydrazino}-carbonyl)-heptyl]-formamide

MH+=391.

Example 95

N-Hydroxy-N-[(R)-2-(N'-{[4-(2-hydroxy-ethyl)-piperazin-1-yl]-trifluoromethyl-pyrimidin-2-yl}-hydrazinocarbonyl)-heptyl]-formamide

MH+=492.

Example 96

N-Hydroxy-N-((R)-2-{N'-[(4-pyrimidin-2-yl-piperazin-1-yl)-trifluoromethyl-pyrimidin-2-yl]-hydrazinocarbonyl}-heptyl)-formamide

MH+=526.

Example 97

N-Hydroxy-N-((R)-2-{N'-[(2-hydroxy-ethylamino)-trifluoromethyl-pyrimidin-2-yl]-hydrazinocarbonyl}-heptyl)-formamide

MH+=423.

Example 98

N-Hydroxy-N-{(R)-2-[N'-(7-trifluoromethyl-benzo[1,2,4]triazin-3-yl)-hydrazinocarbonyl]-heptyl}-formamide

MH+=415.

Example 99

N-Hydroxy-N-{(R)-2[N'-(6-methyl-benzo[1,2,4]triazin-3-yl)-hydrazinocarbonyl]-heptyl}-formamide

MH+=361.

Example 100

N-Hydroxy-N-{(2R)-2-(cyclopentylmethyl)-3-[N'-(5-methyl-1,2,4-benzotriazin-3-yl)hydrazino]-3-oxo-propyl}-formamide

MH+=373.

Example 101

N-Hydroxy-N-[(2R)-2-({N'-[4-(trifluoromethyl)-pyrimidin-2-yl]-hydrazino}-carbonyl)-octyl]-formamide

MH+=378.

Example 102

N-Hydroxy-N-((2R)-2-{[N'-(1,2,4-benzotriazin-3-yl)hydrazino]-carbonyl}-octyl)-formamide

MH+=361.

Example 103

N-Hydroxy-N-[(2R)-2-({N'-[7-(methyloxy)-1,2,4-benzotriazin-3-yl]-hydrazino}-carbonyl)-octyl]-formamide

MH+=391.

Example 104

N-Hydroxy-N-{(R)-2-[N'-(7-methyl-benzo[1,2,4]triazin-3-yl)-hydrazinocarbonyl]-heptyl}-formamide

MH+=361.

Example 105

N-{(R)-2-[N'-(6-Chloro-benzo[1,2,4]triazin-3yl)-hydrazinocarbonyl]-heptyl}-N-hydroxy-formamide

MH+=381.

Example 106

N-Hydroxy-N-{(R)-2-[N'-(5-methoxy-benzo[1,2,4]triazin-3-yl)-hydrazinocarbonyl]-heptyl}-formamide

MH+=377.

Example 107

N-Hydroxy-N-{(R)-2-[N'-(1-methyl-2-oxo-1,2-dihydro-pyridin-4-yl)-hydrazinocarbonyl]-heptyl}-formamide

MH+=325.

Example 108

N-Hydroxy-N-((R)-2-{N'-[(N'-pyridin-2-yl-hydrazino)-trifluoromethyl-pyrimidin-2-yl]-hydrazinocarbonyl}-heptyl)-formamide

MH+=471.

Example 109

N-Hydroxy-N-{(R)-2-[N'-(4-methyl-6-morpholin-4-yl-pyrimidin-2-yl)-hydrazinocarbonyl]-heptyl}-formamide

MH+=395.

Example 110

N-((R)-2-{N'-[4-(4-Ethyl-piperazin-1-yl)-6-methyl-pyrimidin-2-yl]-hydrazinocarbonyl}-heptyl)-N-hydroxy-formamide

MH+=422.

Example 111

N-{(R)-2-[N'-(4,6-Dimethyl-pyrimidin-2-yl)-hydrazinocarbonyl]-heptyl}-N-hydroxy-formamide

MH+=324.

Example 112

N-Hydroxy-N-{(R)-2-[N'-(4-trifluoromethyl-pyridin-2-yl)-hydrazinocarbonyl]-heptyl}-formamide

MH+=363.

Example 113

N-Hydroxy-N-[(R)-2-(N'-isoquinolin-1-yl-hydrazinocarbonyl)heptyl]-formamide

MH+=345.

Example 114

N-Hydroxy-N-[(R)-2-(N'-quinolin-2-yl-hydrazinocarbonyl)-heptyl]-formamide

MH+=345.

Example 115

N-{(R)-2-[N'-(1-Benzyl-2-oxo-1,2-dihydro-pyridin-4-yl)-hydrazinocarbonyl]-heptyl}-N-hydroxy-formamide

MH+=401.

Example 116

N-Hydroxy-N-{(R)-2-[N'-(4-oxo-4H-pyrido[1,2-a][1,3,5]triazin-2-yl)-hydrazinocarbonyl]-heptyl}-formamide

MH+=363.

Example 117

N-Hydroxy-N-{(R)-2-[N'-(4-methyl-pyrimidin-2-yl)-hydrazinocarbonyl]-heptyl}-formamide

MH+=310.

Example 118

N-{(R)-2-[N'-(1-Butyl-2-oxo-1,2-dihydro-pyridin-4-yl)-hydrazinocarbonyl]-heptyl}-N-hydroxy-formamide

MH+=367.

Example 119

N-Hydroxy-N-{(R)-2-[N'-(9-methyl-4-oxo-4H-pyrido[1,2-a][1,3,5]triazin-2-yl)-hydrazinocarbonyl]-heptyl}-formamide

MH+=377.

Example 120

N-Hydroxy-N-{(R)-2-[N'-(6-oxo-4-trifluoromethyl-1,6-dihydro-pyrimidin-2-yl)-hydrazinocarbonyl]-heptyl}-formamide

MH+=380.

Example 121

N-Hydroxy-N-{(R)-2-[N'-(methyl-trifluoromethyl-pyrimidin-2-yl)-hydrazinocarbonyl]-heptyl}-formamide.

MH+=378.

Example 122

N-Hydroxy-N-{(R)-2-[N'-(5-trifluoromethyl-pyridin-2-yl)-hydrazinocarbonyl]-heptyl}-formamide

MH+=363.

Example 123

N-{(R)-2-[N'-(6-Ethoxy-pyridin-2-yl)-hydrazinocarbonyl]-heptyl}-N-hydroxy-formamide

MH+=339.

Example 124

N-Hydroxy-N-[(R)-2-(N'-pyrido[2,3-e]-[1,2,4]triazin-3-yl-hydrazinocarbonyl)-heptyl]-formamide

MH+=348.

Example 125

N-((R)-2-{N'-[1-(1-Ethyl-propyl)-2-oxo-1,2-dihydro-pyridin-4-yl]-hydrazinocarbonyl}-heptyl)-N-hydroxy-formamide

MH+=381.

Example 126

N-Hydroxy-N-((R)-2-{N'-[2-oxo-1-(3-trifluoromethyl-benzyl)-1,2-dihydro-pyridin-4-yl]-hydrazinocarbonyl}-heptyl)-formamide

MH+=469.

Example 127

N-Hydroxy-N-{(R)-2-[N'-(4-methyl-pyridin-2-yl)-hydrazinocarbonyl]-heptyl}-formamide

MH+=309.

Example 128

N-Hydroxy-N-{(R)-2-[N'-(6-methoxy-pyridin-2-yl)-hydrazinocarbonyl]-heptyl}-formamide

MH+=325.

Example 129

N-Hydroxy-N-{(R)-2-[N'-(2-oxo-1-quinolin-8-yl-methyl-1,2-dihydro-pyridin-4-yl)-hydrazinocarbonyl]-heptyl}-formamide

MH+=452.

Example 130

N-Hydroxy-N-[(R)-2-(N'-{2-oxo-1-[2-(5,6,7,8-tetrahydro-[1,8]naphthyridin-2-yl)-ethyl]-dihydro-pyridin-4-yl}-hydrazinocarbonyl)-heptyl]-formamide

MH+=471.

Example 131

N-{(R)-2-[N'-(4,6-Bis-ethylamino-[1,3,5]triazin-2-yl)-hydrazinocarbonyl]-heptyl}-N-hydroxy-formamide

MH+=383.

Example 132

N-{(R)-2-[N'-(Bis-dimethylamino-[1,3,5]triazin-2-yl)-hydrazinocarbonyl]-heptyl}-N-hydroxy-formamide

MH+=383

Example 133

N-{(R)-2-[N'-(4,6-Di-morpholin-4-yl-[1,3,5]triazin-2-yl)-hydrazinocarbonyl]-heptyl}-N-hydroxy-formamide

MH+=467.

Example 134

N-Hydroxy-N-((R)-2-{N'-[4-(4-methyl-piperazin-1-yl)-6-propylamino-[1,3,5]triazin-2-yl]-hydrazinocarbonyl}-heptyl)-formamide

MH+=452.

Example 135

N-{(R)-2-[N'-(Dimethylamino-morpholin-4-yl-[1,3,5]triazin-2-yl)-hydrazinocarbonyl]-heptyl}-N-hydroxy-formamide

MH+=425.

Example 136

N-Hydroxy-N-{(R)-2-[N'-(6-methyl-pyridin-2-yl)-hydrazinocarbonyl]-heptyl}-formamide

MH+=309.

Example 137

N-Hydroxy-N-((R)-2-{N'-[5-(5-phenyl-[1,3,4]oxadiazol-2-yl)-pyridin-2-yl]-hydrazinocarbonyl}-heptyl)-formamide

MH+=439.

Example 138

N-{(R)-2-[N'-(7-tert-Butyl-1,4-dioxo-1,2,3,4-tetrahydro-pyrido[3,4-d]pyridazin-5-yl)-hydrazinocarbonyl]-heptyl}-N-hydroxy-formamide

MH+=435.

Example 139

N-((R)-2-{N'-[4-Ethylamino-6-(4-methyl-[1,4]diazepan-1-yl)-[1,3,5]triazin-2-yl]-hydrazinocarbonyl}-heptyl)-N-hydroxy-formamide

MH+=452.

Example 140

N-((R)-2-{N'-[4-Ethylamino-6-(4-ethyl-piperazin-1-yl)-[1,3,5]triazin-2-yl]-hydrazinocarbonyl}-heptyl)-N-hydroxy-formamide

MH+=452.

Example 141

N-Hydroxy-N-{(R)-2-[N'-(6-trifluoromethyl-pyridin-2-yl)-hydrazinocarbonyl]-heptyl}-formamide

MH+=363.

Example 142

N-Hydroxy-N-{(R)-2-[N'-(4-methyl-6-morpholin-4-yl-methyl-pyrimidin-2-yl)-hydrazinocarbonyl]-heptyl}-formamide

MH+=409.

Example 143

N-Hydroxy-N-{(R)-2-[N'-(4-methyl-6-morpholin-4-yl-[1,3,5]triazin-2-yl)-hydrazinocarbonyl]-heptyl}-formamide

MH+=396.

Example 144

N-Hydroxy-N-{(2R)-2-(cyclopentylmethyl)-3-[N'-(4,6-dimethyl-2-pyrimidinyl)-hydrazino]-3-oxopropyl}-formamide

MH+=336.

Example 145

N-Hydroxy-N-{(R)-2-[N'-(4-methyl-6-pyrrolidin-1-yl-methyl-pyrimidin-2-yl)-hydrazinocarbonyl]-heptyl}-formamide

MH+=393.

Example 146

N-{(R)-2-[N'-(4-Dimethylaminomethyl-6-methyl-pyrimidin-2-yl)-hydrazinocarbonyl]-heptyl}-N-hydroxy-formamide

MH+=367.

Example 147

N-Hydroxy-N-((R)-2-{N'-[4-methyl-6-(4-methyl-piperazin-1-yl-methyl)-pyrimidin-2-yl]-hydrazinocarbonyl}-heptyl)-formamide

MH+=422.

Example 148

N-Hydroxy-N-{(R)-2-[N'-(5-methyl-pyridin-2-yl)-hydrazinocarbonyl]-heptyl}-formamide

MH+=309.

Example 149

N-((R)-2-{N'-[Dimethylamino-(4-methyl-[1,4]diaz-epan-1-yl)-[1,3,5]triazin-2-yl]-hydrazinocarbonyl}-heptyl)-N-hydroxy-formamide

MH+=452.

Example 150

N-Hydroxy-N-{(R)-2-[N'-(4-methyl-6-pyrrolidin-1-yl-[1,3,5]triazin-2-yl)-hydrazinocarbonyl]-heptyl}-formamide

MH+=380.

Example 151

N-Hydroxy-N-((R)-2-{N'-[4-methyl-6-)-4-pyrrolidin-1-yl-piperidin-1-yl]-[1,3,5]triazin-2-yl]-hydrazinocarbonyl}-heptyl)-formamide

MH+=463.

Example 152

N-((R)-2-{N'[(Ethyl-methyl-amino)-methyl-[1,3,5]triazin-2-yl]-hydrazinocarbonyl}-heptyl)-N-hydroxy-formamide

MH+=368.

Example 153

N-((R)-2-{N'-[(4-(4-Ethyl-piperazin-1-yl)-6-methyl-[1,3,5]triazin-2-yl]-hydrazinocarbonyl}-heptyl)-N-hydroxy-formamide

MH+=423.

Example 154

N-Hydroxy-N-[(2R)-7,7,7-trifluoro-2-({N'-[4-(trifluoromethyl)-pyrimidin-2-yl]-hydrazino}-carbonyl)-heptyl]-formamide

MH+=418.

Example 155

N-Hydroxy-N-((2R)-7,7,7-trifluoro-2-{[N'-(5-methyl-1,2,4-benzotriazin-3-yl)-hydrazino]-carbonyl}-heptyl)-formamide

MH+=415.

Example 156

N-Hydroxy-N-((2R)-7,7,7-trifluoro-2-{[N'-(7-methyl-1,2,4benzotriazin-3-yl)-hydrazino]-carbonyl}-heptyl)formamide

MH+=415.

Example 157

N-Hydroxy-N-{(R)-2-[N'-(4-methylamino-6-morpholin-4-yl-[1,3,5]-2-yl)-hydrazinocarbonyl]-heptyl}-formamide

MH+=411.

Example 158

N-((R)-2-{N'-[4-(4-Ethyl-piperazin-1-yl)-6-methylamino-[1,3,5]triazin-2-yl]-hydrazinocarbonyl}-heptyl)-N-hydroxy-formamide

MH+=438.

Example 159

N-{(R)-2-[N'-(4-Ethylamino-6-morpholin-4-yl-[1,3,5]triazin-2-yl)-hydrazinocarbonyl]-heptyl}-N-hydroxy-formamide

MH+=425.

Example 160

N-Hydroxy-N-{(R)-2-[N'-(4,6,7-trimethyl-7,8-dihydro-pterin-2-yl)-hydrazinocarbonyl]-heptyl}-formamide

MH+=392.

Example 161

N-Hydroxy-N-{(R)-2-[N'-(4,6,7-trimethyl-pteridin-2-yl)-hydrazinocarbonyl]-heptyl}-formamide

MH+=390.

Example 162

N-Hydroxy-N-{(R)-2-[N'-(methoxymethoxymethyl-trifluoromethyl-pyrimidin-2-yl)-hydrazinocarbonyl]-heptyl}-formamide

MH+=438.

Example 163

N-Hydroxy-N-((R)-2-{N'-[4-methyl-6-(1-piperidin-1-yl-methanoyl)-pyrimidin-2-yl]-hydrazinocarbonyl}-heptyl)-formamide

MH+=421.

Example 164

2-(N'-{(R)-2-[(Formyl-hydroxy-amino)-methyl]-heptanoyl}-hydrazino)-6-methyl-pyrimidine-4-carboxylic acid cyclopropylamide

MH+=393.

Example 165

2-(N'-{(R)-2-[(Formyl-hydroxy-amino)-methyl]-heptanoyl}-hydrazino)-6-methyl-pyrimidine-4-carboxylic acid diisopropylamide

MH+=437.

Example 166

N-{(R)-2-[N'-(5-Cyano-pyridin-2-yl)-hydrazinocarbonyl]-heptyl}-N-hydroxy-formamide

MH+=320.

Example 167

N-{(R)-2-[N'-(4,6-Diethyl-[1,3,5]triazin-2-yl)-hydrazinocarbonyl]-heptyl}-N-hydroxy-formamide

MH+=353.

Example 168

N-{(R)-4-Cyclopentyl-2-[N'-(4-trifluoromethyl-pyrimidin-2-yl)-hydrazinocarbonyl]-butyl}-N-hydroxy-formamide

MH+=390.

Example 169

N-{(R)-4-Cyclopentyl-2-[N'-(7-methyl-benzo[1,2,4]triazin-3-yl)-hydrazinocarbonyl]-butyl}-N-hydroxy-formamide

MH+=387.

Example 170

N-{(R)-4-Cyclopentyl-2-[N'-(5-methyl-benzo[1,2,4]triazin-3-yl)-hydrazinocarbonyl]-butyl}-N-hydroxy-formamide

MH+=387.

Example 171

N-Hydroxy-N-((R)-2-{N'-[6-(4-methyl-piperazin-1-yl-methyl)-pyridin-2-yl]-hydrazinocarbonyl}-heptyl)-formamide

MH+=407.

Example 172

N-((R)-2-{N'-[5-(4,6-Dimethoxy-pyrimidin-2-yl)-pyridin-2-yl]-hydrazinocarbonyl}-heptyl)-N-hydroxy-formamide

MH+=433.

Example 173

N-{(R)-2-[N'-(Diethylamino-methyl-[1,3,5]triazin-2-yl)-hydrazinocarbonyl]-heptyl}-N-hydroxy-formamide

MH+=382.

Example 174

N-Hydroxy-N-[(R)-2-(N'-{[(2-methoxy-ethyl)-methyl-amino]-methyl-[1,3,5]triazin-2-yl}-hydrazinocarbonyl)-heptyl]-formamide

MH+=397.

Example 175

N-((R)-1-{N'-[4-(2,6-Dimethyl-morpholin-4-yl)-6-methyl-[1,3,5]triazin-2-yl]-hydrazinocarbonyl}-heptyl)-N-hydroxy-formamide

MH+=424.

Example 176

N-{(R)-2-[N'-(5-Fluoro-4-methyl-6-morpholin-4-yl-pyrimidin-2-yl)-hydrazinocarbonyl]-heptyl}-N-hydroxy-formamide

MH+=413.

Example 177

N-{(R)-2-[N'-(4-Ethyl-6-morpholin-4-yl-[1,3,5]triazin-2-yl)-hydrazinocarbonyl]-heptyl}-N-hydroxy-formamide

MH+=410.

Example 178

N-{(R)-2-[N'-(Ethyl-methyl-amino)-[1,3,5]triazin-2-yl)-hydrazinocarbonyl]-heptyl}-N-hydroxy-formamide

MH+=382.

Example 179

N-((R)-2-{N'-[4-Ethyl-6-(4-ethyl-piperazin-1-yl)-[1,3,5]triazin-2-yl]-hydrazinocarbonyl}-heptyl)-N-hydroxy-formamide

MH+=437.

Example 180

N-((R)-2-{N'-[5-Fluoro-4-methyl-6-(4-methyl-piperazin-1-yl)-pyrimidin-2-yl]-hydrazinocarbonyl}-heptyl)-N-hydroxy-formamide

MH+=426.

Example 181

N-{(R)-2-[N'-(Dimethylamino-ethyl-[1,3,5]triazin-2-yl)-hydrazinocarbonyl]-heptyl}-N-hydroxy-formamide

MH+=368.

Example 182

N-((R)-2-{N'-[5-Fluoro-4-methyl-6-(4-methyl-[1,4]diazepan-1-yl)-pyrimidin-2-yl]-hydrazinocarbonyl}-heptyl)-N-hydroxy-formamide

MH+=440.

Example 183

N-{(R)-4-Cyclopentyl-2-[N'-(morpholin-4-yl-trifluoromethyl-pyrimidin-2-yl)-hydrazinocarbonyl]-butyl}-N-hydroxy-formamide

MH+=475.

Example 184

N-[(R)-2-(N'-{Ethyl-[(2-methoxy-ethyl)-methyl-amino]-[1,3,5]triazin-2-yl}-hydrazinocarbonyl)-heptyl]-N-hydroxy-formamide

MH+=412.

Example 185

N-{(R)-2-[N'-(Dimethylamino-methyl-pyrimidin-2-yl)-hydrazinocarbonyl]-heptyl}-N-hydroxy-formamide

MH+=353.

Example 186

N-{(R)-2-[N'-(4-Cyclopropylamino-6-methyl-pyrimidin-2-yl)hydrazinocarbonyl]-heptyl}-N-hydroxy-formamide

MH+=365.

Example 187

N-{(R)-2-Cyclohexyl-2-[N'-(4-trifluoromethyl-pyrimidin-2-yl)-hydrazinocarbonyl]-ethyl}-N-hydroxy-formamide

MH+=376.

Example 188

N-{(R)-2-Cyclohexyl-2-[N'-(7-methoxy-benzo[1,2,4]triazin-3-yl)-hydrazinocarbonyl]-ethyl}-N-hydroxy-formamide

MH+=389.

Example 189

N-{(R)-2-Cyclohexyl-2-[N'-(5-methyl-benzo[1,2,4]triazin-3-yl)-hydrazinocarbonyl]-ethyl}-N-hydroxy-formamide

MH+=373.

Example 190

N-{(R)-4,4-Dimethyl-2-[N'-(4-trifluoromethyl-pyrimidin-2-yl)-hydrazinocarbonyl]-pentyl}-N-hydroxy-formamide

MH+364.

Example 191

N-{(R)-4,4-Dimethyl-2-[N'-(7-methyl-benzo[1,2,4]triazin-3-yl)-hydrazinocarbonyl]-pentyl}-N-hydroxy-formamide

MH+=361.

Example 192

N-{(R)-4,4-Dimethyl-2-[N'-(5-methyl-benzo[1,2,4]triazin-3-yl)-hydrazinocarbonyl]-pentyl}-N-hydroxy-formamide

MH+=361.

Example 193

N-{(R)-4,4-Dimethyl-2-[N'-(morpholin-4-yl-trifluoromethyl-pyrimidin-2-yl)-hydrazinocarbonyl]-pentyl}-N-hydroxy-formamide

MH+=449.

Example 194

N-((R)-2-{N'-[Ethyl-(methyl-pyridin-2-yl-amino)-[1,3,5]triazin-2-yl]-hydrazinocarbonyl}-heptyl)-N-hydroxy-formamide

MH+=431.

Example 195

N-{(R)-2-[N'-(4-Cyclopropylamino-6-ethyl-[1,3,5]triazin-2-yl)-hydrazinocarbonyl]-heptyl}-N-hydroxy-formamide

MH+=380.

Example 196

N-Hydroxy-N-[(R)-2-[N'-(5-methyl-benzo[1,2,4]triazin-3-yl)-hydrazinocarbonyl]-3-(1-methyl-cyclopentyl)-propyl]-formamide

MH+=387.

Example 197

N-Hydroxy-N-[(R)-2-[N'-(7-methoxy-benzo[1,2,4]triazin-3-yl)-hydrazinocarbonyl]-3-(1-methyl-cyclopentyl)-propyl]-formamide

MH+=403

Example 198

N-Hydroxy-N-{(R)-3-(1-methyl-cyclopentyl)-2-[N'-(4-trifluoromethyl-pyrimidin-2-yl)-hydrazinocarbonyl]-propyl}-formamide

MH+=390.

Example 199

N-Hydroxy-N-{(R)-2-[N'-(4-isopropyl-6-morpholin-4-yl-[1,3,5]triazin-2-yl)-hydrazinocarbonyl]-heptyl}-formamide

MH+=424.

Example 200

N-Hydroxy-N-{(2R)-2-(cyclopentylmethyl)-3-[N'-(4-methyl-2-pyrimidinyl)-hydrazino]-3-oxopropyl}-formamide

MH+=322.

Example 201

N-Hydroxy-N-[(2R)-6,6,6-trifluoro-2-({N'-[4-(trifluoromethyl)-pyrimidin-2-yl]-hydrazino}-carbonyl)-hexyl]-formamide

MH+=404.

Example 202

N-{(R)-2-[N'-(5,7-Dimethyl-benzo[1,2,4]triazin-3-yl)-hydrazinocarbonyl]-heptyl}-N-hydroxy-formamide

MH+=375.

Example 203

N-{(R)-2-[N'-(3,6-Dimethyl-pyrazin-2-yl)-hydrazinocarbonyl]-heptyl}-N-hydroxy-formamide

MH+=324.

Example 204

N-((R)-2-{N'-[4-(4-Ethyl-piperazine-1-yl)-6-isopropyl-[1,3,5]triazin-2-yl]-hydrazinocarbonyl}-heptyl)-N-hydroxy-formamide

MH+=451.

Example 205

N-{(R)-2-[N'-(4-Dimethylamino-6-isopropyl-[1,3,5]triazin-2-yl)-hydrazinocarbonyl]-heptyl}-N-hydroxy-formamide

MH+=382.

Example 206

N-Hydroxy-N-{(R)-2-[N'-(methyl-trifluoromethyl-pyridin-2-yl)-hydrazinocarbonyl]-heptyl}-formamide

MH+=377.

Example 207

2-(N'-{(R)-2-[(Formyl-hydroxy-amino)-methyl]-heptanoyl}-hydrazino)-6,N,N-trimethyl-isonicotinamide

MH+=380.

Example 208

N-Hydroxy-N[(2R)-2-({N'-[3-amino-6-(trifluoromethyl)-pyridin-2-yl]-hydrazino}-carbonyl)-heptyl]-formamide

MH+=378.

Example 209

N-Hydroxy-N-[(R)-2-(N'-{4-isopropyl-6-[(2-methoxy-ethyl)-methyl-amino]-[1,3,5]triazin-2-yl}-hydrazinocarbonyl)-heptyl]-formamide

MH+=426.

Example 210

N-{(R)-3-Cyclopentyl-2-[N'-(4-ethyl-6-morpholin-4-yl-[1,3,5]triazin-2-yl)-hydrazinocarbonyl]-propyl}-N-hydroxy-formamide

MH+=422.

Example 211

N-Hydroxy-N-{(R)-2-[N'-(4-morpholin-4-yl-6-propyl-[1,3,5]triazin-2-yl)-hydrazinocarbonyl]-heptyl}-formamide

MH+=424.

Example 212

N-((R)-2-{N'-[4-(4-Ethyl-piperazin-1-yl)-6-propyl-[1,3,5]triazin-2-yl]-hydrazinocarbonyl}-heptyl)-N-hydroxy-formamide

MH+=451.

Example 213

N-{(R)-5,5-Dimethyl-2-[N'-(4-trifluoromethyl-pyrimidin-2-yl)-hydrazinocarbonyl]-hexyl}-N-hydroxy-formamide

MH+=378.

Example 214

N-{(R)-5,5-Dimethyl-2-[N'-(7-methyl-benzo[1,2,4]triazin-3-yl)-hydrazinocarbonyl]-hexyl}-N-hydroxy-formamide

MH+=375.

Example 215

N-{(R)-5,5-Dimethyl-2-[N'-(5-methyl-benzo[1,2,4]triazin-3-yl)-hydrazinocarbonyl]-hexyl}-N-hydroxy-formamide

MH+=375.

Example 216

N-{(R)-5,5-Dimethyl-2-[N'-(morpholin-4-yl-trifluoromethyl-pyrimidin-2-yl)-hydrazinocarbonyl]-hexyl}-N-hydroxy-formamide

MH+=463.

Example 217

N-{(R)-4-Ethyl-2-[N'-(4-trifluoromethyl-pyrimidin-2-yl)-hydrazino carbonyl]-hexyl}-N-hydroxy-formamide

MH+=378.

Example 218

N-{(R)-4-Ethyl-2-[N'-(7-methyl-benzo[1,2,4]triazin-3-yl)-hydrazinocarbonyl]-hexyl}-N-hydroxy-formamide

MH+=375.

Example 219

N-{(R)-4-Ethyl-2-[N'-(morpholin-4-yl-trifluoromethyl-pyrimidin-2-yl)-hydrazinocarbonyl]-hexyl}-N-hydroxy-formamide

MH+=463.

Example 220

N-((R)-3-Cyclopentyl-2-{N'-[4-ethyl-6-(4-ethyl-piperazin-1-yl)-[1,3,5]triazin-2-yl]-hydrazinocarbonyl}-propyl)-N-hydroxy-formamide

MH+=449.

Example 221

N-{(R)-3-Cyclopentyl-2-[N'-(4-cyclopropylamino-6-ethyl-[1,3,5]triazin-2-yl)-hydrazinocarbonyl]-propyl}-N-hydroxy-formamide

MH+=392.

Example 222

N-{(R)-4-Ethyl-2-[N'-(5-methyl-benzo[1,2,4]triazin-3-yl)-hydrazinocarbonyl]-hexyl}-N-hydroxy-formamide

MH+=375.

Example 223

N-Hydroxy-N-[(R)-2-(N'-{[(2-methoxy-ethyl)-methyl-amino]-propyl-[1,3,5]triazin-2-yl}-hydrazinocarbonyl)-heptyl]-formamide

MH+=426.

Example 224

N-{(R)-2-[N'-(Dimethylamino-propyl-[1,3,5]triazin-2-yl)-hydrazinocarbonyl]-heptyl}-N-hydroxy-formamide

MH+=382.

Example 225

N-{(R)-2-[N'-(4-Ethyl-pyrimidin-2-yl)-hydrazinocarbonyl]-heptyl}-N-hydroxy-formamide

MH+=324.

Example 226

N-Hydroxy-N-{(R)-2-[N'-(4-isopropyl-pyrimidin-2-yl)-hydrazinocarbonyl]-heptyl}-formamide

MH+=338.

Example 227

N-{(R)-2-[N'-(4-Cyclopropyl-6-morpholin-4-yl-[1,3,5]triazin-2-yl)-hydrazinocarbonyl]-heptyl}-N-hydroxy-formamide

MH+=422.

Example 228

N-Hydroxy-N-[(2R)-2-({N'-[4-(pyridin-2-yl)-pyrimidin-2-yl]-hydrazino}-carbonyl)-heptyl]-formamide

MH+=373.

Example 229

N-((R)-2-{N'-[4-Cyclopropyl-6-(4-ethyl-piperazin-1-yl)-[1,3,5]triazin-2-yl]-hydrazinocarbonyl}-heptyl)-N-hydroxy-formamide

MH+=449.

Example 230

N-{(R)-2-[N'-(Cyclopropyl-dimethylamino-[1,3,5]triazin-2-yl)-hydrazinocarbonyl]-heptyl}-N-hydroxy-formamide

MH+=380.

Example 231

N-((R)-2-{N'-[Cyclopropyl-(ethyl-methyl-amino)-[1,3,5]triazin-2-yl]-hydrazinocarbonyl}-heptyl)-N-hydroxy-formamide

MH+=394.

Example 232

N-{(R)-2-[N'-(4-Cyclopropyl-6-pyrrolidin-1-yl[1,3,5]triazin-2-yl)-hydrazinocarbonyl]-heptyl}-N-hydroxy-formamide

MH+=406.

Example 233

N-{(R)-2-[N'-(4,6-Dicyclopropyl-[1,3,5]triazin-2-yl)-hydrazinocarbonyl]-heptyl}N-hydroxy-formamide

MH+=377.

Example 234

N-Hydroxy-N-[(R)-2[N'-(5-methyl-benzo[1,2,4]triazin-3-yl)-hydrazinocarbonyl]-3-(2-methyl-cyclopentyl)-propyl]-formamide

MH+=387.

Example 235

N-[(R)-2-[N'-(Dimethylamino-ethyl-[1,3,5]triazin-2-yl)-hydrazinocarbonyl]-3-(2-methyl-cyclopentyl)-propyl]-N-hydroxy-formamide

MH+=394.

Example 236

N-Hydroxy-N-[(R)-2-[N'-(4-trifluoromethyl-pyrimidin-2-yl)-hydrazinocarbonyl]-3-(2-methyl-cyclopentyl)-propyl]-formamide

MH+=390.

Example 237

N-{(R)-2-[N'-(5-Ethyl-pyrimidin-2-yl)-hydrazinocarbonyl]-heptyl}-N-hydroxy-formamide

MH+=324.

Example 238

N-Hydroxy-N-{(2R)-2-(cyclopentylmethyl)-3-[N'-(7-methyl-1,2,4-benzotriazin-3-yl)-hydrazino]-3-oxopropyl}-formamide

MH+=373.

Example 239

N-Hydroxy-N-[(2R)-2-(cyclopentylmethyl)-3-(N'-{4-ethyl-6-[ethyl(methyl)amino]-1,3,5-triazin-2-yl}-hydrazino)-3-oxopropyl]-formamide

MH+=394.

Example 240

N-Hydroxy-N-((2R)-2-(cyclopentylmethyl)-3-{N'-[4-(dimethylamino)-6-ethyl-1,3,5-triazin-2-yl]-hydrazino}-3-oxopropyl)-formamide

MH+=380.

Example 241

N-((R)-2-{N'-[4-Ethyl-6-(4-isopropyl-piperazin-1-yl)-[1,3,5]triazin-2-yl]-hydrazinocarbonyl}-heptyl)-N-hydroxy-formamide

MH+=451.

Example 242

N-Hydroxy-N-[(2R)-3-[N'-(6-chloro-1,2,4-benzotriazin-3-yl)-hydrazino]-2-(cyclopentylmethyl)-3-oxopropyl]-formamide

MH+=393.

Example 243

N-{(R)-4,4-Dimethyl-2-[N'-(4-trifluoromethyl-pyrimidin-2-yl)-hydrazinocarbonyl]-hexyl}-N-hydroxy-formamide

MH+=378.

Example 244

N-{(R)-4,4-Dimethyl-2-[N'-(7-methyl-benzo[1,2,4]triazin-3-yl)-hydrazinocarbonyl]-hexyl}-N-hydroxy-formamide

MH+=375.

Example 245

N-{(R)-4,4-Dimethyl-2-[N'-(5-methyl-benzo[1,2,4]triazin-3-yl)-hydrazinocarbonyl]-hexyl}-N-hydroxy-formamide

MH+=375.

Example 246

N-{(R)-4,4-Dimethyl-2-[N'-(morpholin-4-yl-trifluoromethyl-pyrimidin-2-yl)-hydrazinocarbonyl]-hexyl}-N-hydroxy-formamide

MH+=463.

Example 247

N-Hydroxy-N-{(R)-2-[N'-(5-phenyl-[1,2,4]triazin-3-yl)-hydrazinocarbonyl]-heptyl}-formamide

MH+=373.

Example 248

N-{(R)-2-[N'-(4-Ethyl-6-morpholin-4-yl-pyrimidin-2-yl)-hydrazinocarbonyl]-heptyl}-N-hydroxy-formamide

MH+=409.

Example 249

N-((R)-2-{N'-[4-Ethyl-6-(4-methyl-piperazin-1-yl)-pyrimidin-2-yl]-hydrazinocarbonyl}-heptyl)-N-hydroxy-formamide

MH+=422.

Example 250

N-{(R)-2-[N'-(5-Ethyl-4-methyl-pyrimidin-2-yl)-hydrazinocarbonyl]-heptyl}-N-hydroxy-formamide

MH+=338.

Example 251

N-((R)-2-{N'-[4-Ethyl-6-(4-propyl-piperazin-1-yl)-[1,3,5]triazin-2-yl]-hydrazinocarbonyl}-heptyl)-N-hydroxy-formamide

MH+=451.

Example 252

N-Hydroxy-N-((R)-2-{N'-[6-(4-pyrimidin-2-yl-piperazin-1-yl-methyl)-pyridin-2-yl]-hydrazinocarbonyl}-heptyl)-formamide

MH+=471.

Example 253

N-Hydroxy-N-((R)-2-{N'-[6-(3-[1,2,4]triazol-1-yl-methyl-[1,2,4]triazol-1-yl)-pyridin-2-yl]-hydrazinocarbonyl}-heptyl)-formamide

MH+=443.

Example 254

N-{(R)-3-Bicyclo[2.2.1]hept-7-yl-2-[N'-(4-trifluoromethyl-pyrimidin-2-yl)-hydrazinocarbonyl]-propyl}-N-hydroxy-formamide

MH+=402.

Example 255

N-{(R)-3-Bicyclo[2.2.1]hept-7-yl-2-[N'-(morpholin-4-yl-trifluoromethyl-pyrimidin-2-yl)-hydrazinocarbonyl]-propyl}-N-hydroxy-formamide

MH+=487.

Example 256

N-hydroxy-N-[(R)-2-(N'-pyridin-3-yl-hydrazinocarbonyl)-heptyl]-formamide

MH+=295.

Example 257

4-{4-Ethyl-6-[2-((2R)-2-{[formyl(hydroxy)amino]-methyl}-heptanoyl)-hydrazino]-1,3,5-triazin-2-yl}-1-methyl-1-propylpiperazin-1-ium iodide

MH+=465.

Example 258

N-{(R)-3-Bicyclo[2.2.1]hept-7-yl-2-[N'-(5-methyl-benzo[1,2,4]triazin-3-yl)-hydrazinocarbonyl]-propyl}-N-hydroxy-formamide

MH+=399.

Example 259

N-{(R)-2-[N'-(4-Azetidin-1-yl-6-ethyl-[1,3,5]triazin-2-yl)-hydrazinocarbonyl]-heptyl}-N-hydroxy-formamide

MH+=380.

Example 260

N-{(R)-2-Cyclopentyl-2-[N'-(4-trifluoromethyl-pyrimidin-2-yl)-hydrazinocarbonyl]-ethyl}-N-hydroxy-formamide

MH+=362.

Example 261

N-{(R)-2-Cyclopentyl-2-[N'-(morpholin-4-yl-4-trifluoromethyl-pyrimidin-2-yl)-hydrazinocarbonyl]-ethyl}-N-hydroxy-formamide

MH+=447.

Example 262

N-{(R)-2-Cyclopentyl-2-[N'-(4-methyl-pyridin-2-yl)-hydrazinocarbonyl]-ethyl}-N-hydroxy-formamide

MH+=307.

Example 263

N-{(R)-2-Cyclopentyl-2-[N'-(dimethylamino-ethyl-[1,3,5]triazin-2-yl)-hydrazinocarbonyl]-ethyl}-N-hydroxy-formamide

MH+=366.

Example 264

N-{(R)-2-Cyclopentyl-2-[N'-(7-methyl-benzo[1,2,4]triazin-3-yl)-hydrazinocarbonyl]-ethyl}-N-hydroxy-formamide

MH+=359.

Example 265

N-{(R)-2-Cyclopentyl-2-[N'-(5-methyl-benzo[1,2,4]triazin-3-yl)-hydrazinocarbonyl]-ethyl}-N-hydroxy-formamide

MH+=359.

Example 266

N-Hydroxy-N-{(R)-2-[N'-(5-methyl-benzo[1,2,4]triazin-3-yl)-hydrazinocarbonyl]-2-(4-methyl-cyclohexyl)-ethyl}-formamide

MH+=387.

Example 267

N-Hydroxy-N-{(R)-2-[N'-(7-methyl-benzo[1,2,4]triazin-3-yl)-hydrazinocarbonyl]-2-(4-methyl-cyclohexyl)-ethyl}-formamide

MH+=387.

Example 268

N-Hydroxy-N-{(R)-2-(4-methyl-cyclohexyl)-2-[N'-(4-trifluoromethyl-pyrimidin-2-yl)-hydrazinocarbonyl]-ethyl}-formamide

MH+=390.

Example 269

N-Hydroxy-N-{(R)-2-(4-methyl-cyclohexyl)-2-[N'-(morpholin-4-yl-trifluoromethyl-pyrimidin-2-yl)-hydrazinocarbonyl]-ethyl}-formamide

MH+=475.

Example 270

N-Hydroxy-N-{(R)-2-(4-methyl-cyclohexyl)-2-[N'-(4-methyl-pyridin-2-yl)-hydrazinocarbonyl]-ethyl}-formamide

MH+=335.

Example 271

N-{(R)-2-[N'-(Dimethylanino-ethyl-[1,3,5]triazin-2-yl)-hydrazinocarbonyl]-2-(4-methyl-cyclohexyl)-ethyl}-N-Hydroxy-formamide

MH+=394.

Example 272

N-{(R)-2-[N'-(6,7-Dihydro-5H-cyclopentapyrimidin-2-yl)-hydrazinocarbonyl]-heptyl}-N-hydroxy-formamide

MH+=336.

Example 273

N-((R)-2-[N'-[4-Ethyl-6-((S)-2-hydroxymethyl-pyrrolidin-1-yl)-[1,3,5]triazin-2-yl]-hydrazinocarbonyl]-heptyl)-N-hydroxy-formamide

MH+=424.

Example 274

N-{(R)-2-[N'-(Dimethylamino-pyridin-3-yl-pyrimidin-2-yl)-hydrazinocarbonyl]-heptyl}-N-hydroxy-formamide

MH+=416.

Example 275

N-{(R)-2-[N'-(Dimethylamino-pyridin-4-yl-pyrimidin-2-yl)-hydrazinocarbonyl]-heptyl}-N-hydroxy-formamide

MH+=416.

Example 276

N-Hydroxy-N-{(R)-2-N'-(5,6,7,8-tetrahydro-benzo[1,2,4]triazin-3-yl)-hydrazinocarbonyl]-heptyl}-formamide

MH+=351.

Example 277

N-{(R)-2-[N'-(5,6-Diethyl-[1,2,4]triazin-3-yl)-hydrazinocarbonyl]-heptyl}-N-hydroxy-formamide

MH+=353.

Example 278

N-Hydroxy-N-{(R)-2-[N'-[5-(4-hydroxy-phenyl)-[1,2,4]triazin-3-yl]-hydrazinocarbonyl}-heptyl)-formamide

MH+=389.

Example 279

N-[(R)-2-(N'-{[(2-Dimethylamino-ethyl)-methyl-amino]-ethyl-[1,3,5]triazin-2-yl}-hydrazinocarbonyl)-heptyl]-N-hydroxy-formamide

MH+=425.

Example 280

N-{(R)-2-[N'-(2-Dimethylamino-quinazolin-4-yl)-hydrazinocarbonyl]-heptyl}-N-hydroxy-formamide

MH+=389.

Example 281

N-Hydroxy-N-{(R)-2-[N'-(3-methanesulfonyl-4,6-dimethyl-pyridin-2-yl)-hydrazinocarbonyl]-heptyl}-formamide

MH+=401.

Example 282

N-((R)-2-{N'-[4-Ethyl-6-(3-hydroxy-piperidin-1-yl)-[1,3,5]triazin-2-yl]-hydrazinocarbonyl}-heptyl)-N-hydroxy-formamide

MH+=424.

Example 283

N-[(R)-2-(N'-[4,5']Bipyrimidinyl-2-yl-hydrazinocarbonyl)-heptyl]-N-hydroxy-formamide

MH+=374.

Example 284

N-((R)-2-{N'-[(Cyclopropyl-methyl-amino)-ethyl-[1,3,5]triazin-2-yl]-hydrazinocarbonyl}-heptyl)-N-hydroxy-formamide

MH+=394.

Example 285

N-((R)-2-{N'-[4-Ethyl-6-((R)-3-hydroxy-pyrrolidin-1-yl)-[1,3,5]triazin-2-yl]-hydrazinocarbonyl}-heptyl)-N-hydroxy-formamide

MH+=410.

Example 286

N-Hydroxy-N-[(R)-2-(N'-[3,3']Bipyridinyl-5-yl-hydrazinocarbonyl)-heptyl]-formamide

MH+=372.

Example 287

N-Hydroxy-N-[(R)-2-(N'-(5-morpholin-4-yl-pyridin-3-yl)-hydrazinocarbonyl)-heptyl]-formamide

MH+=380.

Example 288

N-Hydroxy-N-{(R)-2-[N'-(4-pyridin-3-yl-pyrimidin-2-yl)-hydrazinocarbonyl]-heptyl}-formamide

MH+=373.

Example 289

N-Hydroxy-N-{(R)-2-[N'-(5,6,7,8-tetrahydro-quinazolin-2-yl)-hydrazinocarbonyl]-heptyl}-formamide

MH+=350.

Example 290

N-[(R)-2-(N'-{[Cyclopropyl-1-(1-methyl-piperidin-4-yl)amino]-ethyl-[1,3,5]triazin-2-yl}-hydrazinocarbonyl)-heptyl]-N-hydroxy-formamide

MH+=477.

Example 291

N-((R)-2-{N'-[4-((R)-3-Dimethylamino-pyrrolidin-1-yl)-6-ethyl-[1,3,5]triazin-2-yl]-hydrazinocarbonyl}-heptyl)-N-hydroxy-formamide

MH+=437.

Example 292

N-Hydroxy-N-[(R)-2-(N'-[5-(1H-pyrrol-2-yl)-pyridin-3-yl]-hydrazinocarbonyl)-heptyl]-formamide

MH+=360.

Example 293

N-Hydroxy-N-[(R)-2-(N'-[(4-methyl-piperazin-1-yl)-trifluoromethyl-pyrimidin-4-yl]-hydrazinocarbonyl)-heptyl]-formamide

MH+=462.

Example 294

N-Hydroxy-N-[(R)-2-(N'-(5-Furan-3-yl-pyridin-3-yl)-hydrazinocarbonyl)-heptyl]-formamide

MH+=361.

Example 295

N-{(R)-5,5-Dimethyl-2-[N'-(4-trifluoromethyl-pyrimidin-2-yl)-hydrazinocarbonyl]-heptyl}-N-hydroxy-formamide

MH+=392.

Example 296

N-{(R)-5,5-Dimethyl-2-[N'-(7-methyl-benzo[1,2,4]triazin-3-yl)-hydrazinocarbonyl]-heptyl}-N-hydroxy-formamide

MH+=389.

Example 297

N-{(R)-5,5-Dimethyl-2-(4-methyl-pyridin-2-yl)-hydrazinocarbonyl]-heptyl}-N-hydroxy-formamide

MH+=337.

Example 298

N-{(R)-2-Cycloheptyl-2-[N'-(4-trifluoromethyl-pyrimidin-2-yl)-hydrazinocarbonyl]-ethyl}-N-hydroxy-formamide

MH+=390.

Example 299

N-{(R)-2-Cycloheptyl-2-[N'-(4-methyl-pyridin-2-yl)-hydrazinocarbonyl]-ethyl}-N-hydroxy-formamide

MH+=335.

Example 300

N-{(R)-2-Cycloheptyl-2-[N'-(dimethylamino-ethyl-[1,3,5]triazin-2-yl)-hydrazinocarbonyl]-ethyl}-N-hydroxy-formamide

MH+=394.

Example 301

N-{(R)-2-Cycloheptyl-2-[N'-(7-methyl-benzo[1,2,4]triazin-3-yl)-hydrazinocarbonyl]-ethyl}-N-hydroxy-formamide

MH+=387.

Example 302

N-((R)-2-{N'-[4-Ethyl-6-(4-hydroxy-piperidin-1-yl)-[1,3,5]triazin-2-yl]-hydrazinocarbonyl}-heptyl)-N-hydroxy-formamide

MH+=424.

Example 303

N-{(R)-5,5-Dimethyl-2-[N'-(5-methyl-benzo[1,2,4]triazin-3-yl)-hydrazinocarbonyl]-heptyl}-N-hydroxy-formamide

MH+=389.

Example 304

N-{(R)-2-[N'-(4-Dimethylamino-quinazolin-2-yl)-hydrazinocarbonyl]-heptyl}-N-hydroxy-formamide

MH+=389.

Example 305

N-Hydroxy-N-{(R)-2-[N'-(4-pyridin-4-yl-pyrimidin-2-yl)-hydrazinocarbonyl]-heptyl}-formamide

MH+=373.

Example 306

N-Hydroxy-N-((R)-2-{N'-[4-(3-hydroxymethyl-phenyl)-pyrimidin-2-yl]-hydrazinocarbonyl}-heptyl)-formamide

MH+=402.

Example 307

N-Hydroxy-N-((R)-2-{N'-[4-(4-hydroxymethyl-phenyl)-pyrimidin-2-yl]-hydrazinocarbonyl}-heptyl)-formamide

MH+=402.

Example 308

N-((R)-2-{N'-[4-Ethyl-6-(3-methoxy-piperidin-1-yl)-[1,3,5]triazin-2-yl]-hydrazinocarbonyl}-heptyl)-N-hydroxy-formamide

MH+=438.

Example 309

N-Hydroxy-N-{(R)-2-[N'-(7-methyl-benzo[1,2,4]triazin-3-yl)-hydrazinocarbonyl]-2-(4-methyl-cyclohexyl)-ethyl}-formamide

MH+=387.

Example 310

N-[(R)-2-{N'-[Ethyl-(ethyl-methylamino)-[1,3,5]triazin-2-yl]-hydrazinocarbonyl}-2-(4-methyl-cyclohexyl)-ethyl}-N-hydroxy-formamide

MH+=408.

Example 311

N-[(R)-2-{N'-[Ethyl-(ethyl-methylamino)-[1,3,5]triazin-2-yl]-hydrazinocarbonyl}-2-(4-methyl-cyclohexyl)-ethyl}-N-hydroxy-formamide

MH+=408.

Example 312

N-Hydroxy-N-{(R)-2-[N'-(7-methyl-benzo[1,2,4]triazin-3-yl)-hydrazinocarbonyl]-2-(4-methyl-cyclohexyl)-ethyl}-formamide

MH+=387.

Example 313

N-((R)-2-{N'-[4-(2,6-Dimethoxy-phenyl)-pyrimidin-2-yl]-hydrazinocarbonyl}-heptyl)-N-hydroxy-formamide

MH+=432.

Example 314

N-((R)-2-{N'-[4-Ethyl-6-((R)-3-methoxy-pyrrolidin-1-yl)-[1,3,5]triazin-2-yl]-hydrazinocarbonyl}-heptyl)-N-hydroxy-formamide

MH+=424.

Example 315

N-((R)-2-{N'-[4-Ethyl-6-(4-methoxy-piperidin-1-yl)-[1,3,5]triazin-2-yl]-hydrazinocarbonyl}-heptyl)-N-hydroxy-formamide

MH+=438.

Example 316

N-Hydroxy-N-[(R)-2-(N'-(6-pyrrolidin-1-yl-pyrimidin-4-yl)-hydrazinocarbonyl)-heptyl]-formamide

MH+=365.

Example 317

N-Hydroxy-N-[(R)-2-(N'-[6-(4-methyl-piperazin-1-yl)-pyrimidin-4-yl])-hydrazinocarbonyl)-heptyl]-formamide

MH+=394.

Example 318

N-{(R)-2-[N'-(6-Dimethylamino-pyrimidin-4-yl)-hydrazinocarbonyl]-heptyl}-N-hydroxy-formamide

MH+=339.

Example 319

N-{(R)-2-[N'-(Pyridin-4-yl-trifluoromethyl-pyrimidin-4-yl)-hydrazinocarbonyl]-heptyl}-N-hydroxy-formamide

MH+=441.

Example 320

N-{(R)-2-[N'-(Pyridin-3-yl-trifluoromethyl-pyrimidin-4-yl)-hydrazinocarbonyl]-heptyl}-N-hydroxy-formamide

MH+=441.

Example 321

N-{(R)-2-[N'-(2-Ethylamino-6-trifluoromethyl-pyrimidin-4-yl)-hydrazinocarbonyl]-heptyl}-N-hydroxy-formamide

MH+=407.

Example 322

N-Hydroxy-N-((R)-2-{N'-[5-(4-methoxy-phenyl)-[1,2,4]triazin-3-yl]-hydrazinocarbonyl}-heptyl)-formamide

MH+=403.

Example 323

N-Hydroxy-N-((R)-2-{N'-[4-(2,3,4-trimethoxy-phenyl)-pyrimidin-2-yl]-hydrazinocarbonyl}-heptyl)-formamide

MH+=462.

Example 324

N-{(R)-4,4-Dimethyl-2-[N'-(4-trifluoromethyl-pyrimidin-2-yl)-hydrazinocarbonyl]-heptyl}-N-hydroxy-formamide

MH+=392.

Example 325

N-{(R)-4,4-Dimethyl-2-[N'-(7-methyl-benzo[1,2,4]triazin-3-yl)-hydrazinocarbonyl]-heptyl}-N-hydroxy-formamide

MH+=389.

Example 326

N-{(R)-4,4-Dimethyl-2-[N'-(5-methyl-benzo[1,2,4]triazin-3-yl)-hydrazinocarbonyl]-heptyl}-N-hydroxy-formamide

MH+=389.

Example 327

N-{(R)-4,4-Dimethyl-2-[N'-(4-methyl-pyridin-2-yl)-hydrazinocarbonyl]-heptyl}-N-hydroxy-formamide

MH+=337.

Example 328

N-Hydroxy-N-{(R)-2-[N'-(6-morpholin-4-yl-pyrimidin-4-yl)-hydrazinocarbonyl]-heptyl}-formamide

MH+=381.

Example 329

N-Hydroxy-N-[(R)-2-(N'-{5-[4-(2-hydroxy-ethoxy)-phenyl]-[1,2,4]triazin-3-yl}-hydrazinocarbonyl)-heptyl]-formamide

MH+=433.

Example 330

N-{(R)-2-[N'-(4-Furan-2-yl-pyrimidin-2-yl)-hydrazinocarbonyl]-heptyl}-N-hydroxy-formamide

MH+=362.

Example 331

N-((R)-2-{N'-[4-(3,5-Dimethyl-isoxazol-4-yl)-pyrimidin-2-yl]-hydrazinocarbonyl}-heptyl)-N-hydroxy-formamide

MH+=391.

Example 332

N-Hydroxy-N-{(R)-2-[N'-(4-methyl-1-oxy-pyridin-2-yl)-hydrazinocarbonyl]-heptyl}-formamide

MH+=325.

Example 333

2-(N'-{(R)-2-[(Formyl-hydroxy-amino)-methyl]-heptanoyl}-hydrazino)-6-methyl-nicotinic acid

MH+=353.

Example 334

N-Hydroxy-N-{(R)-2-[N'-(3-methoxy-pyridin-2-yl)hydrazinocarbonyl]-heptyl}-formamide

MH+=325.

Example 335

N-Hydroxy-N-{(2R)-2-[(N'-{4-[4-(methylsulfonyl)phenyl]-pyrimidin-2-yl}-hydrazino)-carbonyl]-heptyl}-formamide

MH+=450.

Example 336

N-Hydroxy-N-[(2R)-2-({N'-[4-(furan-3-yl)-pyrimidin-2-yl]-hydrazino}-carbonyl)-heptyl]-formamide

MH+=362.

Example 337

N-[(2R)-2-({N'-[4-(2-aminophenyl)-pyrimidin-2-yl]-hydrazino}-carbonyl)-heptyl]-N-hydroxy-formamide

MH+=387.

Example 338

N-Hydroxy-N-[(2R)-2-({N'-[5-(5-methyl-1,3,4-oxadiazol-2-yl)-4-(trifluoromethyl)-pyrimidin-2-yl]-hydrazino}-carbonyl)-heptyl]-formamide

MH+=446.

Example 339

N-Hydroxy-N-((2R)-2-(cyclopentylmethyl)-3-{N'-[5-(5-methyl-1,3,4-oxadiazol-2-yl)-4-(trifluoromethyl)-pyrimidin-2-yl]-hydrazino}-3-oxopropyl)-formamide

MH+=458.

Example 340

N-[(2R)-2-({N'-[6-(dimethylamino)-2-methyl-pyrimidin-4-yl]-hydrazino}-carbonyl)-heptyl]-N-hydroxy-formamide

MH+=353.

Example 341

N-[(2R)-2-({N'-[2-Cyclopropyl-6-(dimethylamino)-pyrimidin-4-yl]-hydrazino}-carbonyl)-heptyl]-N-hydroxy-formamide

MH+=379.

Example 342

N-Hydroxy-N-[(2R)-4-(2-thienyl)-2-({N'-[4-(trifluoromethyl)-pyrimidin-2-yl]-hydrazino}-carbonyl)-butyl]-formamide

MH+=404.

Example 343

N-Hydroxy-N-[(2R)-2-{[N'-(4-methyl-pyrimidin-2-yl)hydrazino]carbonyl}-4-(2-thienyl)-butyl]-formamide

MH+=350.

Example 344

N-[(2R)-2-[(N'-{4-Ethyl-6-[ethyl(methyl)amino]-1,3,5-triazin-2-yl}-hydrazino)-carbonyl]-4-(2-thienyl)butyl]-N-hydroxy-formamide

MH+=422.

Example 345

N-Hydroxy-N-((2R)-3-oxo-2-(2-thienylmethyl)-3-{N'-[4-(trifluoromethyl)-pyrimidin-2-yl]-hydrazino}-propyl)-formamide

MH+=390.

Example 346

N-Hydroxy-N-[(2R)-3-[N'-(4-methyl-pyrimidin-2-yl)hydrazino]-3-oxo-2-(2-thienylmethyl)-propyl]-formamide

MH+=336.

Example 347

N-[(2R)-3-(N'-{4-Ethyl-6-[ethyl(methyl)amino]-1,3,5-triazin-2-yl}hydrazino)-3-oxo-2-(2-thienylmethyl)-propyl]-N-hydroxy-formamide

MH+=408.

Example 348

N-Hydroxy-N-[(2R)-2-({N'-[2-methyl-6-(pyridin-2-yl)-pyrimidin-4yl]-hydrazino}-carbonyl)-heptyl]-formamide

MH+=387.

Example 349

N-Hydroxy-N-[(2R)-2-({N'-[6-(pyridin-2-yl-methyl)-pyridazin-3-yl]-hydrazino}-carbonyl)-heptyl]-formamide

MH+=387.

Example 350

N-Hydroxy-N-[(2R)-2-({N'-[2-methyl-6-(morpholin-4-yl)-pyrimidin-4-yl]-hydrazino}-carbonyl)-heptyl]-formamide

MH+=395.

Example 351

N-Hydroxy-N-[(2R)-2-({N'-[6-(morpholin-4-yl)-2-(trifluoromethyl)-pyrimidin-4-yl]-hydrazino}-carbonyl)-heptyl]-formamide

MH+=449.

Example 352

N-Hydroxy-N-{(2R)-2-[(N'-{4-[methyl-(pyridin-2-yl)-amino]-pyrimidin-2-yl}-hydrazino)-carbonyl]-heptyl}-formamide

MH+=402.

Example 353

N-Hydroxy-N-((2R)-2-(cyclopentylmethyl)-3-{N'-[4-cyclopropyl-6-(dimethylamino)-1,3,5-triazin-2-yl]-hydrazino}-3-oxopropyl)-formamide

MH+=392.

Preparation 19

(1,3-Dioxo-1,3-dihydro-isoindol-2-yl)-carbamic acid tert-butyl ester

To a mixture of tert-butyl carbazate (5.15 g, 38.97 mmol) and phthalic anhydride (5.77 g, 38.97 mmol) was added CHCl$_3$ (70 mL). The reaction mixture was refluxed for 18 h. Removal of the solvent under reduced pressure yielded 8.20 g (80%) of the title compound as a white solid. MH+263.

Preparation 20

Benzo[1,3]dioxol-5-yl-methyl-(1,3-dioxo-1,3-dihydro-isoindol-2-yl)-carbamic acid dimethyl-ethyl ester To a solution of (1,3-dioxo-1,3dihydro-isoindol-2-yl)-carbamic acid tert-butyl ester (0.31 g, 1.18 mmol), piperonyl alcohol (0.18 g, 1.18 mmol) and triphenylphosphine (0.40 g, 1.54 mmol) in THF (12 mL) at 0° C. was added dropwise diisopropyl azodicarboxylate (0.30 mL, 1.54 mmol). The reaction mixture was stirred and allowed to warm up to room temperature overnight. Removal of the solvent under reduced pressure, followed by purification by hplc yielded 0.28 g (60%) of the title compound. MH+397.

Preparation 21

N-Benzo[1,3]dioxol-5-yl-methyl-hydrazinecarboxylic acid tert-butyl ester

To N-benzo[1,3]dioxol-5-yl-methyl-(1,3-dioxo-1,3-dihydro-isoindol-2-yl)-carbamic acid dimethyl-ethyl ester (0.28 g, 0.71 mmol) in EtOH (3.6 mL) was added hydrazine monohydrate (0.14 mL, 2.84 mmol) in one portion at room temperature. The reaction mixture was stirred for 21 hrs. Toluene (5 mL) was added to the mixture, and the white solid was collected by filtration. The filtrate was evaporated in vacuo. Further standing under high vacuum yielded 0.17 g (89%) of the title compound. MH+267.

Preparation 22

N-Benzo[1,3]dioxol-4-yl-methyl-N'-{(R)-2-[(benzyloxy-formyl-amino)-methyl]-heptanoyl}-hydrazinecarboxylic acid tert-butyl ester To a mixture of N-benzo[1,3]dioxol-5-yl-methyl-hydrazinecarboxylic acid tert-butyl ester (168 mg, 0.632 mmol), (R)-2-[(benzyloxy-formyl-amino)-methyl]-heptanoic acid (185 mg, 0.632 mmol), 4-dimethylaminopyridine (100 mg, 0.822 mmol) in methylene chloride (7 mL) was added 1-(3-dimethylaminopropyl)-3-ethylcarbodiimde hydrochloride (158 mg, 0.822 mmol) at room temperature. The reaction mixture was stirred for 19 h at room temperature and then treated with aqueous 1N HCl solution. Separation of the organic layer, drying over anhydrous $MgSO_4$ and removal of the solvent provided the title compound No further purification was required. MH+542.

Preparation 23

N-[(R)-2-(N'-Benzo[1,3]dioxol-5-yl-methyl-hydrazinocarbonyl)-heptyl]-N-benzyloxy-formamide To the crude N-benzo[1,3]dioxol-4-ylmethyl-N'-{R-2-[(benzyloxy-formyl-amino)-methyl]-heptanoyl}-hydrazinecarboxylic acid tert-butyl ester obtained in Preparation 12 was added 5% TFA in methylene dichloride (20 mL) at room temperature. The resulting solution was stirred for 6 hours, and then washed with saturated aqueous $NaHCO_3$ solution (20 mL×3). The organic layer was separated and dried ($MgSO_4$). Filtration and evaporation provided the title. compound (0.221 g, 79% in two steps). MH+442.

Example 354

N-[(R)-2-(N'-Benzo[1,3]dioxol-5-yl-methyl-hydrazinocarbonyl)-heptyl]-N-hydroxy-formamide To a solution of N-[(R)-2-(N'-Benzo[1,3]dioxol-5-yl-methyl-hydrazinocarbonyl)-heptyl]-N-benzyloxy-formamide (0.221 g, 0.501 mmol) in EtOH (10 mL) was added 10% Pd/C (50 mg). The mixture was subjected to hydrogenation for 5 h at room temperature. The mixture was filtered through Celite. The filtrate was evaporated and purified by HPLC to afford the title compound (0.10 g, 57%) in a white solid. MH+352.

Example 355

N-{(R)-2-[N'-(2,3-Dihydro-[1,4]dioxino[2,3-b]pyridin-7-yl-methyl)-hydrazinocarbonyl]-heptyl}-N-hydroxy-formamide

MH+366.

Example 356

N-{(R)-2-[N'-(4-Dimethylamino-benzyl)-hydrazinocarbonyl]-heptyl}-N-hydroxy-formamide

MH+351.

Example 357

N-Hydroxy-N-((R)-2-{N'-[2-(5,6,7,8-tetrahydro-[1,8]naphthyridin-2-yl)-ethyl]-hydrazinocarbonyl]-heptyl}-N-hydroxy-formamide

MH+378.

Example 358

N-Hydroxy-N-[(R)-2-(N'-quinolin-2-yl-methyl-hydrazinocarbonyl)-heptyl]-formamide

MH+359.

Example 359

N-Hydroxy-N-{(R)-2-[N'-(1,2,3,4-tetrahydro-quinolin-2-yl-methyl)-hydrazinocarbonyl]-heptyl}-formamide

MH+363.

Example 360

N-Hydroxy-N-[(R)-2-(N'-quinolin-6-yl-methyl-hydrazinocarbonyl)-heptyl]-formamide

MH+359.

Example 361

N-[(R)-2-(N'-Benzofuran-2-yl-methyl-hydrazinocarbonyl)-heptyl]-N-hydroxy-formamide

MH+348.

Example 362

N-[(R)-2-(N'-Cyclopropylmethyl-hydrazinocarbonyl)-heptyl]-N-hydroxy-formamide

MH+272.

Example 363

N-{(R)-2-[N'-(6-Fluoro-4H-benzo[1,3]dioxin-8-yl-methyl)-hydrazinocarbonyl]-heptyl}-N-hydroxy-formamide

MH+384

Example 364

N-Hydroxy-N-{(R)-2-[N'-(4-methoxy-benzyl)-hydrazinocarbonyl]-heptyl}-formamide

MH+=338.

Example 365

N-Hydroxy-N-{(R)-2-[N'-(2-methoxy-benzyl)-hydrazinocarbonyl]-heptyl}-formamide

MH+=338.

Example 366

N-Hydroxy-N-{(R)-2-[N'-(tetrahydro-furan-3-yl-methyl)-hydrazinocarbonyl]-heptyl}-formamide

MH+=302.

Example 367

N-[(R)-2-(N'-Furan-3-yl-methyl-hydrazinocarbonyl)-heptyl]-N-hydroxy-formamide

MH+=298.

Example 368

N-{(R)-2-[N'-(2,3-Dihydro-benzo[1,4]dioxin-6-yl-methyl)-hydrazinocarbonyl]-hepyl}-N-hydroxy-formamide

MH+=366.

Example 369

N-{(R)-2-[N'-(2,3-Dihydro-benzo[1,4]dioxin-2-yl-methyl)-hydrazinocarbonyl]-heptyl}-N-hydroxy-formamide

MH+=366.

Example 370

N-Hydroxy-N-{(R)-2-[N'-(2-phenoxy-ethyl)-hydrazinocarbonyl]-heptyl}-formamide

MH+=338.

Example 371

N-{(R)-2-[N'-((S)-2,3-Dihydroxy-propyl)-hydrazinocarbonyl]-heptyl}-N-hydroxy-formamide

MH+=292.

Example 372

N-Hydroxy-N-{(R)-2-[N'-(5-methyl-isoxazol-3-yl-methyl)-hydrazinocarbonyl]-heptyl}-formamide

MH+=313.

Example 373

N-((R)-2-{N'-[1-(1-Benzo[1,3]dioxol-5-yl-methanoyl)-piperidin-4-yl]-hydrazinocarbonyl}-heptyl)-N-hydroxy-formamide

MH+=449.

Example 374

N-((R)-2-{N'-[1-(1-Benzofuran-2-yl-methanoyl)-piperidin-4-yl]-hydrazinocarbonyl}-heptyl)-N-hydroxy-formamide

MH+=445.

Example 375

N-Hydroxy-N-[(R)-2-(N'-{1-[1-(7-methoxy-benzofuran-2-yl)-methanoyl]-piperidin-4-yl}-hydrazinocarbonyl)-heptyl]-formamide

MH+=475.

Example 376

N-{(R)-2-[N'-(1-Benzyl-piperidin-4-yl)-hydrazinocarbonyl]-heptyl}-N-hydroxy-formamide

MH+=391.

Example 377

N-[(R)-2-(N'-{1-[1-(3,4-Dichloro-phenyl)-methanoyl]-piperidin-4-yl}-hydrazinocarbonyl)-heptyl]-N-hydroxy-formamide

MH+=474.

Example 378

N-[(R)-2-(N'-{1-[1-(2,3-Dichloro-phenyl)-methanoyl]-piperidin-4-yl}-hydrazinocarbonyl)-heptyl]-N-hydroxy-formamide

MH+=474.

Example 379

N-Hydroxy-N-[(R)-2-(N'-{1-[1-(4-methyl-piperazin-1-yl)-methanoyl]-pentyl}-hydrazinocarbonyl)-heptyl]-formamide

MH+=414.

Preparation 24

N-[(R)-2-(Hydrazinocarbonyl)-heptyl]-N-hydroxy-formamide

To a solution of N'-{(R)-2-[(Benzyloxyformylamino)methyl]heptanoyl]-hydrazinecarboxylic acid benzyl ester (1 mmol) in EtOH (10 mL) was added 10% Pd/C (50 mg). The mixture was subjected to hydrogenation for 5 hours at room temperature and then filtered through Celite. The filtrate was evaporated and purified by hplc to afford N-[(R)-2-(Hydrazinocarbonyl)-heptyl]-N-hydroxy-formamide as a glass. MH+218.

Example 380

N-[(R)-2-(N'-Benzyl-hydrazinocarbonyl)-heptyl]-N-hydroxy-formamide

N-[(R)-2-(Hydrazinocarbonyl)-heptyl]-N-hydroxy-formamide (50 mg, 0.23 mmoles) and benzaldehyde (24 mg, 0.23 mmoles) were dissolved in methanol (2 mL) under argon in the. presence of 4 Å molecular sieves (50 mg), stirred for 1 hour and cooled to 0° C. To the mixture was added one crystal of methyl orange indicator and enough methanolic HCl to keep the solution acidic (red color). Sodium cyanoborohydride (17 mg, 0.28 mmoles) was added, along with enough methanolic HCl to keep the solution acidic (red indicator).

The system was warmed to room temperature, stirred for two days, neutralized with sodium bicarbonate solution, and extracted with ethyl acetate (3×). The organic layer was dried over anhydrous sodium sulfate, concentrated to dryness and purified by prep hplc to afford the title compound. MH+308.

Compositions, Administration and Biological Assays

Compounds of Formula (1) and their pharmaceutically acceptable salts may be administered in a standard manner for antibiotics, for example orally, parenterally, sub-lingually, dermally, transdermally, rectally, via inhalation or via buccal administration.

Compositions of Formula (1) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils, and incorporated in a soft gelatin capsule shell.

Typical parenteral compositions consist of a solution or suspension of a compound or salt in a sterile aqueous or non-aqueous carrier optionally containing a parenterally acceptable oil, for example, polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example, polymeric glycols, gelatins, cocoa-butter or other low melting vegetable waxes or fats or their synthetic analogs.

Typical dermal and transdermal formulations comprise a conventional aqueous or non-aqueous vehicle, for example, a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1-400 mg and preferably 10 to 200 mg per person. A topical formulation contains suitably 0.01 to 5.0% of a compound of Formula (1).

The daily dosage regimen for oral administration is suitably about 0.01 mg/Kg to 40 mg/Kg of a compound of Formula (1) or a pharmaceutically acceptable salt thereof calculated as the free acid. The daily dosage regimen for parenteral administration is suitably about 0.001 mg/Kg to 40 mg/Kg of a compound of Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (1) are demonstrated by the following test:

Biological Assay.

*S. aureus* or *E. coli* PDF activity is measured at 25° C., using a continuous enzyme-linked assay developed by Lazennec & Meinnel ("Formate dehydrogenase-coupled spectrophotometric assay of peptide deformylase", Anal. Biochem. 1997, 244, pp. 180-182), with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay.

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: Staphylococcus aureus Oxford, Staphylococcus aureus WCUH29, Enterococcus faecalis I, Enterococcus faecalis 7, Haemophilus influenzae Q1, Haemophilus influenzae NEMC1, Moraxella catarrhalis 1502, Streptococcus pneumoniae 1629, Streptococcus pneumoniae N1387, Streptococcus pneumoniae N1387, E. coli 7623 (AcrABEFD+) and E. coli 120 (AcrAB−). The minimum inhibitory concentration (NEC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (1):

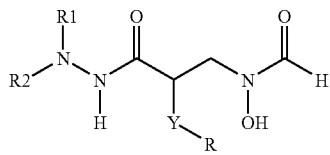

wherein:
R is selected from the group consisting of:
C$_{2-6}$ alkyl optionally substituted by alkoxy or halogen; C$_{2-6}$ alkenyl optionally substituted by alkoxy or halogen; C$_{2-6}$ alkynyl optionally substituted by alkoxy or halogen; (CH$_2$)$_n$—C$_{3-6}$ carbocycle optionally substituted by alkoxy or halogen; and (CH$_2$)$_n$—R4, wherein R4 is selected from the group consisting of phenyl, furanyl, benzofuranyl, thienyl, benzothienyl, tetrahydrofuranyl, tetrahydropyranyl, dioxanyl, 1,4-benzodioxanyl and benzo[1,3]dioxonyl; and wherein R4 is optionally substituted by one or more substituents selected from the group consisting of Cl, Br, I and C$_{1-3}$ alkyl optionally substituted by one to three F;
R1 and R2 are independently selected from the group consisting of:
hydrogen, optionally substituted aryl, optionally substituted heteroaryl, optionally substituted heterocyclic, and C$_{1-3}$ substituted alkyl;
wherein said C$_{1-3}$ substituted alkyl is substituted with at least one substituent selected from the group consisting of: C$_{1-3}$ alkyl optionally substituted by one to three fluorines; C$_{2-3}$ alkenyl; C$_{2-3}$ alkynyl; C$_{1-2}$ alkoxy optionally substituted by one to three fluorines; sulfanyl; sulfinyl; sulfonyl; hydroxyl; mercapto; amino; guanidino; carboxy; aminocarbonyl; aryl; aryloxy; heteroaryl; heteroaryloxy; heterocyclic; aminosulfonyl; sulfonylamino; carboxyamide; ureido; nitro; cyano; and halogen
Y represents O, CH$_2$ or a covalent bond; and
n is an integer from 0 to 2;
or a pharmaceutically acceptable salt thereof.

2. A compound according to claim 1, wherein R2 represents hydrogen; or a pharmaceutically acceptable salt thereof.

3. A compound according to claim 2, with the following absolute configuration:

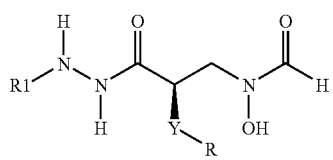

or a pharmaceutically acceptable salt thereof.

4. A compound according to claim 3 wherein:
R is selected from the group consisting of:
C$_{2-6}$ alkyl optionally substituted by alkoxy or halogen; (CH$_2$)$_n$—C$_{3-6}$ carbocycle optionally substituted by alkoxy or halogen; and (CH$_2$)$_n$—R4, wherein R4 is selected from the group consisting of phenyl, furanyl, benzofuranyl, thienyl, benzothienyl, tetrahydrofuranyl, tetrahydropyranyl, dioxanyl, 1,4-benzodioxanyl and benzo[1,3]dioxonyl; and wherein R4 is optionally substituted by one or more substituents selected from the group consisting of Cl, Br, I and C$_{1-3}$ alkyl optionally substituted by one to three F;
R1 is selected from the group consisting of:
hydrogen, optionally substituted aryl, optionally substituted heteroaryl, optionally substituted heterocyclic, and C$_{1-3}$ substituted alkyl;
wherein said C$_{1-3}$ substituted alkyl is substituted with at least one substituent selected from the group consisting of: C$_{1-3}$ alkyl optionally substituted by one to three fluorines; C$_{1-2}$ alkoxy optionally substituted by one to three fluorines; hydroxyl; aryl; aryloxy; heteroaryl; heteroaryloxy; and heterocyclic;
Y represents O, CH$_2$ or a covalent bond; and
n is an integer from 0 to 2;
or a pharmaceutically acceptable salt thereof.

5. A compound according to claim 3 wherein:
R is selected from the group consisting of:
C$_{2-6}$ alkyl optionally substituted by alkoxy or halogen; (CH$_2$)$_n$—C$_{3-6}$ carbocycle optionally substituted by alkoxy or halogen; and (CH$_2$)$_n$—R4, wherein R4 is selected from the group consisting of phenyl, furanyl, benzofuranyl, thienyl, benzothienyl, tetrahydrofuranyl, tetrahydropyranyl, dioxanyl, 1,4-benzodioxanyl and benzo[1,3]dioxonyl; and wherein R4 is optionally substituted by one or more substituents selected from the group consisting of Cl, Br, I and C$_{1-3}$ alkyl optionally substituted by one to three F;
R1 is selected from the group consisting of:
hydrogen, optionally substituted aryl, optionally substituted heteroaryl, optionally substituted heterocyclic, and C$_{1-3}$ substituted alkyl;
wherein said C$_{1-3}$ substituted alkyl is substituted with at least one substituent selected from the group consisting of: C$_{1-3}$ alkyl optionally substituted by one to three fluorines; C$_{2-3}$ alkenyl; C$_{2-3}$ alkynyl; C$_{1-2}$ alkoxy optionally substituted by one to three fluorines; sulfanyl; sulfinyl; sulfonyl; hydroxyl; mercapto; amino; guanidino; carboxy; aminocarbonyl; aryl; aryloxy; heteroaryl; heteroaryloxy; heterocyclic; aminosulfonyl; sulfonylamino; carboxyamide; ureido; nitro; cyano; and halogen;
Y represents CH$_2$ or a covalent bond; and
n is an integer from 0 to 2;
or a pharmaceutically acceptable salt thereof.

6. A compound according to claim 3 wherein Y is a covalent bond; or a pharmaceutically acceptable salt thereof.

7. A compound according to claim 3 wherein Y is CH$_2$; or a pharmaceutically acceptable salt thereof.

8. A compound according to claim 3 wherein R is C$_{2-6}$ alkyl optionally substituted by alkoxy or halogen; or a pharmaceutically acceptable salt thereof.

9. A compound according to claim 8 wherein R is unsubstituted C$_{2-6}$ alkyl; or a pharmaceutically acceptable salt thereof.

10. A compound according to claim 3 wherein R is unsubstituted (CH$_2$)$_n$—C$_{3-6}$ carbocycle; or a pharmaceutically acceptable salt thereof.

11. A compound according to claim 10 wherein R is cyclopropyl, cyclobutyl, cyclopentyl or cyclohexyl; or a pharmaceutically acceptable salt thereof.

12. A compound according to claim 3 wherein R is unsubstituted (CH$_2$)$_n$—R4 and R4 is thienyl; or a pharmaceutically acceptable salt thereof.

13. A compound according to claim 3 wherein R1 is C$_{1-3}$ substitued alkyl or a pharmaceutically acceptable salt thereof.

14. A compound according to claim 13 wherein R1 is $C_{1-3}$ alkyl substituted by at least one substituent selected from the group consisting of: hydroxyl, aryl, aryloxy, heteroaryl, and heterocyclic; or a pharmaceutically acceptable salt thereof.

15. A compound according to claim 3 wherein R1 is optionally substituted aryl; or a pharmaceutically acceptable salt thereof.

16. A compound according to claim 3 wherein R1 is optionally substituted heteroaryl; or a pharmaceutically acceptable salt thereof.

17. A compound according to claim 16 wherein the optionally substituted heteroaryl R1 is benzoimidazolyl, benzothiazolyl, benzoisothiazolyl, benzothiophenyl, benzopyrazinyl, benzotriazolyl, benzotriazinyl, benzo[1,4]dioxanyl, benzofuranyl, 9H-a-carbolinyl, cinnolinyl, 2,3-dihydro-[1,4]dioxino[2,3-b]-pyridinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyrazolopyrimidinyl, pyrazolopyridinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl or thiazolidinyl, 18. A compound according to claim 17 wherein the R1 heteroaryl is substituted by one or more of the following: heteroaryl; heterocyclic; aryl; $C_{1-3}$ alkoxy optionally substituted by one to three F; aryloxy; aralkoxy; acyl; aroyl; heteroaroyl; acyloxy; aroyloxy; heteroaroyloxy; sulfanyl; sulfinyl; sulfonyl; aminosulfonyl; sulfonylamino; carboxyamide; aminocarbonyl; carboxy; oxo; hydroxy; mercapto; amino; nitro; cyano; halogen; ureido; or $C_{1-3}$ substituted alkyl;
wherein said $C_{1-3}$ substituted alkyl is substituted with at least one substituent selected from the group consisting of: $C_{1-3}$ alkyl optionally substituted by one to three fluorines; $C_{2-3}$ alkenyl; $C_{2-3}$ alkynyl; $C_{1-2}$ alkoxy optionally substituted by one to three fluorines; sulfanyl; sulfinyl; sulfonyl; oxo; hydroxy; mercapto; amino; guanidino; carboxy; aminocarbonyl; aryl; aryloxy; heteroaryl; heteroaryloxy; heterocyclic; aminosulfonyl; sulfonylamino; carboxyamide; ureido; nitro; cyano; and halogen.

19. A compound according to claim 3 wherein R1 is optionally substituted heterocyclic; or a pharmaceutically acceptable salt thereof.

20. A pharmaceutical composition comprising a compound according to claim 3 or a pharmaceutically acceptable salt thereof and a pharmaceutical carrier.

21. A compound which is:
N-Hydroxy-N-[(R)-2-(N'-pyridin-2-yl-hydrazinocarbonyl)-heptyl]-formamide;
N-Hydroxy-N-{(R)-2-[N'-(3-methoxy-phenyl)-hydrazinocarbonyl]-heptyl}-formamide;
N-{(R)-2-[N'-(4-Cyano-phenyl)-hydrazinocarbonyl]-heptyl}-N-hydroxy-formamide;
N-{(R)-2-[N'-(2,6-Dimethyl-pyrimidin-4-yl)-hydrazinocarbonyl]-heptyl}-N-hydroxy-formamide;
N-Hydroxy-N-[(R)-2-(N'-quinoxalin-2-yl-hydrazinocarbonyl)-heptyl]-formamide;
N-Hydroxy-N-((2R)-2-{N'-(3,4-dihydro-quinoxalin-2-yl)-hydrazinocarbonyl]-heptyl)-formamide;
N-Hydroxy-N-{(R)-2-[N'-(1,3,4-trimethyl-1H-pyrazolo[3,4-b]pyridin-6-yl)-hydrazinocarbonyl]-heptyl}-formamide;
4-(N'-{(R)-2-[(Formyl-hydroxy-amino)-methyl]-heptanoyl}-hydrazino)-benzenesulfonamide;
N-Hydroxy-N-[(2R)-2-(cyclohexylmethyl)-3-oxo-3-{N'-[4-(trifluoromethyl)-pyrimidin-2-yl]-hydrazino}-propyl]-formamide;
N-{(R)-2-[N'-(Dimethyl-trifluoromethyl-pyrimidin-4-yl)-hydrazinocarbonyl]-heptyl}-N-hydroxy-formamide;
N-Hydroxy-N-{(R)-2-[N'-(6-trifluoromethyl-pyridazin-3-yl)-hydrazinocarbonyl]-heptyl}-formamide;
N-Hydroxy-N-{(R)-2-[N'-(6-trifluoromethyl-pyrimidin-4-yl)-hydrazinocarbonyl]-heptyl}-formamide;
N-Hydroxy-N-{(R)-2-[N'-(5-methyl-[1,2,4]triazolo[1,5-a]pyrimidin-7-yl)-hydrazinocarbonyl]-heptyl}-formamide;
N-Hydroxy-N-{(R)-2-[N'-(9H-purin-6-yl)-hydrazinocarbonyl]-heptyl}-formamide;
N-{(R)-2-[N'-(5-Cyano-pyrimidin-2-yl)-hydrazinocarbonyl]-heptyl}-N-hydroxy-formamide;
N-Hydroxy-N-((2R)-2-{[N'-(pyrimidin-2-yl)-hydrazino]carbonyl}-heptyl)-formamide;
N-Hydroxy-N-((2R)-2-(cyclobutylmethyl)-3-oxo-3-{N'-[4-(trifluoromethyl)-pyrimidin-2-yl]-hydrazino}-propyl)-formamide;
N-Hydroxy-N-{(R)-2-[N'-(6-imidazol-1-yl-pyrimidin-4-yl)-hydrazinocarbonyl]-heptyl}-formamide;
N-[(R)-2-(N'-Benzo[1,2,4]triazin-3-yl-hydrazinocarbonyl)-heptyl]-N-hydroxy-formamide;
N-Hydroxy-N-{(R)-2-[N'-(7-methoxy-benzo[1,2,4]triazin-3-yl)-hydrazinocarbonyl]-heptyl}-formamide;
N-Hydroxy-N-{(R)-2-[N'-(1-methyl-1H-pyrazolo[3,4-d]pyrimidin-6-yl)-hydrazinocarbonyl]-heptyl}-formamide;
N-((R)-2-{N'-[6-(5-Chloro-pyridin-3-yl-oxy)-pyridazin-3-yl]-hydrazinocarbonyl}-heptyl)-N-hydroxy-formamide;
N-Hydroxy-N-[(2R)-2-({N'-[6-(1H-pyrrol-1-yl)-3-pyridazinyl]-hydrazino}-carbonyl)-heptyl]-formamide;
N-Hydroxy-N-((2R)-2-{[N'-(9-methyl-9H-purin-6-yl)-hydrazino]-carbonyl}-heptyl)-formamide;
N-Hydroxy-N-{(R)-2-[N-({6-morpholin-4-yl}-9H-purin-2-yl)-hydrazinocarbonyl]-heptyl}-formamide;
N-{(R)-2-[N'-(6-Fluoro-pyridin-2-yl)-hydrazinocarbonyl]-heptyl}-N-hydroxy-formamide;
N-Hydroxy-N-((2R)-2-{[N'-(1-methyl-1H-pyrazolo[3,4-d]pyrimidin-4-yl)-hydrazino]-carbonyl}-heptyl)-formamide;
N-{(R)-2-[N'-(4-Amino-6-isopropyl-[1,3,5]triazin-2-yl)-hydrazinocarbonyl]-heptyl}-N-hydroxy-formamide;
N-{(R)-2-[N'-(2,5-Dimethyl-4-nitro-2H-pyrazol-3-yl)-hydrazinocarbonyl]-heptyl}-N-hydroxy-formamide;
N-{(R)-2-[N'-(3-Chloro-1-methyl-1H-pyrazolo[3,4-d]pyrimidin-6-yl)-hydrazinocarbonyl]-heptyl}-N-hydroxy-formamide;
N-{(R)-2-[N'-(6-Dimethylamino-9H-purin-2-yl)-hydrazinocarbonyl]-heptyl}-N-hydroxy-formamide;
N-Hydroxy-N-[(2R)-4-cyclopropyl-2-({N'-[4-(trifluoromethyl)-pyrimidin-2-yl]-hydrazino}-carbonyl)-butyl]-formamide;
N-Hydroxy-N-((2R)-2-(cyclopropylmethyl)-3-oxo-3-{N'-[4-(trifluoromethyl)-pyrimidin-2-yl]-hydrazino}-propyl)-formamide;
N-Hydroxy-N-{(R)-2-[N'-methyl-N'-(4-trifluoromethyl-pyrimidin-2-yl)-hydrazinocarbonyl]-heptyl}-formamide;

-2-(N'-{(R)-2-[(Formyl-hydroxy-amino)-methyl]-heptanoyl}-hydrazino)-4-trifluoromethyl-pyrimidine-5-carboxylic acid;
N-{(R)-2-[N'-(5-Fluoro-4-methoxy-pyrimidin-2-yl)-hydrazinocarbonyl]-heptyl}-N-hydroxy-formamide;
N-{(R)-2-[N'-(4-Dimethylamino-pyrimidin-2-yl)-hydrazinocarbonyl]-heptyl}-N-hydroxy-formamide;
N-Hydroxy-N-{(2R)-2-[(N'-{6-[(2-hydroxyethyl)amino]-1,3-dihydro-2H-purin-2-ylidene}-hydrazino)-carbonyl]-heptyl}-formamide;
2-(N'-{(R)-2-[(Formyl-hydroxy-amino)-methyl]-heptanoyl}-hydrazino)-4-trifluoromethyl-pyrimidine-5-carboxylic acid dimethylamide;
N-Hydroxy-N-{(R)-2-[N'-(3-oxo-3,4-dihydro-quinoxalin-2-yl)-hydrazinocarbonyl]-heptyl}-formamide;
N-{(R)-2-Butoxy-2-[N'-(4-trifluoromethyl-pyrimidin-2-yl)-hydrazinocarbonyl]-ethyl}-N-hydroxy-formamide;
2-(N'-{(R)-2-[(Formyl-hydroxy-amino)-methyl]-heptanoyl}-hydrazino)4-trifluoromethyl-pyrimidine-5-carboxylic acid (2-fluoro-phenyl)-amide;
2-(N'-{(R)-2-[(Formyl-hydroxy-amino)-methyl]-heptanoyl}-hydrazino)-4-trifluoromethyl-pyrimidine-5-carboxylic acid tert-butylamide;
N-Hydroxy-N-((R)-2-{N'-[(1-piperidin-1-yl-methanoyl)-trifluoromethyl-pyrimidin-2-yl]-hydrazinocarbonyl}-heptyl)-formamide;
N-{(R)-2-[N'-(5-Cyano-4-trifluoromethyl-pyrimidin-2-yl)-hydrazinocarbonyl]-heptyl}-N-hydroxy-formamide;
N-Hydroxy-N-[(2R)-2-({N'-[9-(4,4,4-trifluorobutyl)-1,9-dihydro-2H-purin-2-ylidene]-hydrazino}-carbonyl)-heptyl]-formamide;
N-Hydroxy-N-((R)-2-{N'-[(1-morpholin-4-yl-methanoyl)-trifluoromethyl-pyrimidin-2-yl]-hydrazinocarbonyl}-heptyl)-formamide;
2-(N'-{(R)-2-[(Formyl-hydroxy-amino)-methyl]-heptanoyl}-hydrazino)-4-trifluoromethyl-pyrimidine-5-carboxylic acid benzylamide;
2-[2-((2R)-2-{[Formyl(hydroxy)amino]methyl}heptanoyl)hydrazino]-N-methyl-N-2-pyridinyl-4-(trifluoromethyl)-5-pyrimidinecarboxamide;
2-[2-((2R)-2-{[Formyl(hydroxy)amino]methyl}heptanoyl)hydrazino]-N-methyl-N-phenyl-4-(trifluoromethyl)-5-pyrimidinecarboxamide;
2-(N'-{(R)-2-[(Formyl-hydroxy-amino)-methyl]-heptanoyl}-hydrazino)-4-trifluoromethyl-pyrimidine-5-carboxylic acid morpholin-4-ylamide;
N-Hydroxy-N-((R)-2-{N'-[(N'-phenyl-hydrazinocarbonyl)-trifluoromethyl-pyrimidin-2-yl]-hydrazinocarbonyl}-heptyl)-formamide;
2-(N'-{(R)-2-[(Formyl-hydroxy-amino)-methyl]-heptanoyl}-hydrazino)-4-trifluoromethyl-pyrimidine-5-carboxylic acid piperidin-1-ylamide;
2-(N'-{(R)-2-[(Formyl-hydroxy-amino)-methyl]-heptanoyl}-hydrazino)-4-trifluoromethyl-pyrimidine-5-carboxylic acid pyrrol-1-ylamide;
N-Hydroxy-N-{(R)-2-[N'-(1-methyl-1H-benzoimidazol-2-yl)-hydrazinocarbonyl]-heptyl}-formamide;
N-{(R)-2-[N'-(4-Cyclopropylamino-5-fluoro-pyrimidin-2-yl)-hydrazinocarbonyl]-heptyl}-N-hydroxy-formamide;
N-[(R)-2-(N-Benzo[1,2,4]triazin-3-yl-hydrazinocarbonyl)-3-cyclopentyl-propyl]-N-hydroxy-formamide;
N-Hydroxy-N-[(R)-2-N'-{[(2-hydroxy-ethyl)-methyl-amino]-trifluoromethyl-pyrimidin-2-yl}-hydrazinocarbonyl)-heptyl]-formamide;
N-Hydroxy-N-((2R)-2-(cyclopentylmethyl)-3-{N'-[4-(cyclopropylamino)-5-fluoro-pyrimidin-2-yl]hydrazino}-3-oxopropyl)-formamide;
N-Hydroxy-N-[(2R)-3-{N'-[4-(azetidin-1-yl)-5-fluoropyrimidin-2-yl]-hydrazino}-2-(cyclopentylmethyl)-3-oxopropyl]-formamide;
N-Hydroxy-N-[(2R)-5-methyl-2-({N'-[4-(trifluoromethyl)-pyrimidin-2-yl]-hydrazino}-carbonyl)-hexyl]-formamide;
N-[(R)-2-(N'-Benzo[1,2,4]triazin-3-yl-hydrazinocarbonyl)-5-methyl-hexyl]-N-hydroxy-formamide;
N-{(R)-2-[N'-(7-Chloro-benzo[1,2,4]triazin-3-yl)-hydrazinocarbonyl]-heptyl}-N-hydroxy-formamide;
N-Hydroxy-N-[(2R)-6-methyl-2-({N'-[4-(trifluoromethyl)-pyrimidin-2-yl]-hydrazino}-carbonyl)-heptyl]-formamide;
N-Hydroxy-N-{(R)-2-[N'-(5-methyl-benzo[1,2,4]triazin-3-yl)-hydrazinocarbonyl]-heptyl}-formamide;
N-((R)-2-{N'-[(4-Ethyl-piperazin-1-yl)-trifluoromethyl-pyrimidin-2-yl]-hydrazinocarbonyl}-heptyl)-N-hydroxy-formamide;
N-Hydroxy-N-{(R)-2-[N'-(piperazin-1-yl-trifluoromethyl-pyrimidin-2-yl)-hydrazinocarbonyl]-heptyl}-formamide;
N-{(R)-2-[N'-(7-Fluoro-benzo[1,2,4]triazin-3-yl)-hydrazinocarbonyl]-heptyl}-N-hydroxy-formamide;
N-Hydroxy-N-[(2R)-2-({N'-[4-(4-ethyl-1-piperazinyl)-6-(trifluoromethyl)-pyrimidin-2-yl]-hydrazino}-carbonyl)-6-methylheptyl]-formamide;
N-Hydroxy-N-[(2R)-6-methyl-2-({N'-[4-(piperazin-1-yl)-6-(trifluoromethyl)-pyrimidin-2-yl]-hydrazino}-carbonyl)-heptyl]-formamide;
N-Hydroxy-N-[(2R)-6-methyl-2-({N'-[4-(4-methyl-piperazin-1-yl)-6-(trifluoromethyl)-pyrimidin-2-yl]-hydrazino}-carbonyl)-heptyl]-formamide;
N-Hydroxy-N-((R)-2-{N'-[(2-methoxy-ethylamino)-trifluoromethyl-pyrimidin-2-yl]-hydrazinocarbonyl}-heptyl)-formamide;
N-Hydroxy-N-[(R)-2-(N'-{[4-(2-hydroxy-ethyl)-piperazin-1-yl]-trifluoromethyl-pyrimidin-2-yl}-hydrazinocarbonyl)-heptyl]-formamide;
N-Hydroxy-N-((R)-2-{N'-[(2-hydroxy-ethylamino)-trifluoromethyl-pyrimidin-2-yl]-hydrazinocarbonyl}-heptyl)-formamide;
N-Hydroxy-N-{(R)-2-[N'-(7-trifluoromethyl-benzo[1,2,4]triazin-3-yl)-hydrazinocarbonyl]-heptyl}-formamide;
N-Hydroxy-N-{(R)-2-[N'-(6-methyl-benzo[1,2,4]triazin-3-yl)-hydrazinocarbonyl]-heptyl}-formamide;
N-Hydroxy-N-[(2R)-2-({N'-[4-(trifluoromethyl)-pyrimidin-2-yl]-hydrazino}-carbonyl)-octyl]-formamide;
N-Hydroxy-N-{(R)-2-[N'-(7-methyl-benzo[1,2,4]triazin-3-yl)-hydrazinocarbonyl]-heptyl}-formamide;
N-{(R)-2-[N'-(6-Chloro-benzo[1,2,4]triazin-3-yl)-hydrazinocarbonyl]-heptyl}-N-hydroxy-formamide;
N-Hydroxy-N-{(R)-2-[N'-(5-methoxy-benzo[1,2,4]triazin-3-yl)-hydrazinocarbonyl]-heptyl}-formamide;
N-Hydroxy-N-{(R)-2-[N'-(1-methyl-2-oxo-1,2-dihydropyridin-4-yl)-hydrazinocarbonyl]-heptyl}-formamide;
N-Hydroxy-N-((R)-2-{N'-[(N'-pyridin-2-yl-hydrazino)-trifluoromethyl-pyrimidin-2-yl]-hydrazinocarbonyl}-heptyl)-formamide;
N-Hydroxy-N-{(R)-2-[N'-(4-methyl-6-morpholin-4-yl-pyrimidin-2-yl)-hydrazinocarbonyl]-heptyl}-formamide;

N-((R)-2-{N'-[4-(4-Ethyl-piperazin-1-yl)-6-methyl-pyrimidin-2-yl]-hydrazinocarbonyl}-heptyl)-N-hydroxy-formamide;
N-{(R)-2-[N'-(4,6-Dimethyl-pyrimidin-2-yl)-hydrazinocarbonyl]-heptyl}-N-hydroxy-formamide;
N-Hydroxy-N-{(R)-2-[N'-(4-trifluoromethyl-pyridin-2-yl)-hydrazinocarbonyl]-heptyl}-formamide;
N-Hydroxy-N-[(R)-2-(N'-isoquinolin-1-yl-hydrazinocarbonyl)-heptyl]-formamide;
N-Hydroxy-N-[(R)-2-(N'-quinolin-2-yl-hydrazinocarbonyl)-heptyl]-formamide;
N-{(R)-2-[N'-(1-Benzyl-2-oxo-1,2-dihydro-pyridin-4-yl)-hydrazinocarbonyl]-heptyl}-N-hydroxy-formamide;
N-Hydroxy-N-{(R)-2-[N'-(4-oxo-4H-pyrido[1,2-a][1,3,5]triazin-2-yl)-hydrazinocarbonyl]-heptyl}-formamide;
N-Hydroxy-N-{(R)-2-[N'-(4-methyl-pyrimidin-2-yl)-hydrazinocarbonyl]-heptyl}-formamide;
N-{(R)-2-[N'-(1-Butyl-2-oxo-1,2-dihydro-pyridin-4-yl)-hydrazinocarbonyl]-heptyl}-N-hydroxy-formamide;
N-Hydroxy-N-{(R)-2-[N'-(9-methyl-4-oxo-4H-pyrido[1,2-a][1,3,5]triazin-2-yl)-hydrazinocarbonyl]-heptyl}-formamide;
N-Hydroxy-N-{(R)-2-[N'-(6-oxo-4-trifluoromethyl-1,6-dihydro-pyrimidin-2-yl)-hydrazinocarbonyl]-heptyl}-formamide;
N-Hydroxy-N-{(R)-2-[N'-(methyl-trifluoromethyl-pyrimidin-2-yl)-hydrazinocarbonyl]-heptyl}-formamide;
N-Hydroxy-N-{(R)-2-[N'-(5-trifluoromethyl-pyridin-2-yl)-hydrazinocarbonyl]-heptyl}-formamide;
N-{(R)-2-[N'-(6-Ethoxy-pyridin-2-yl)-hydrazinocarbonyl]-heptyl}-N-hydroxy-formamide;
N-Hydroxy-N-[(R)-2-(N'-pyrido[2,3-e]-[1,2,4]triazin-3-yl-hydrazinocarbonyl)-heptyl]-formamide;
N-((R)-2-{N'-[1-(1-Ethyl-propyl)-2-oxo-1,2-dihydro-pyridin-4-yl]-hydrazinocarbonyl}-heptyl)-N-hydroxy-formamide;
N-Hydroxy-N-((R)-2-{N'-[2-oxo-1-(3-trifluoromethyl-benzyl)-1,2-dihydro-pyridin-4-yl]-hydrazinocarbonyl}-heptyl)-formamide;
N-Hydroxy-N-{(R)-2-[N'-(4-methyl-pyridin-2-yl)-hydrazinocarbonyl]-heptyl}-formamide;
N-Hydroxy-N-{(R)-2-[N'-(6-methoxy-pyridin-2-yl)-hydrazinocarbonyl]-heptyl}-formamide;
N-Hydroxy-N-{(R)-2-[N'-(2-oxo-1-quinolin-8-yl-methyl-1,2-dihydro-pyridin-4-yl)-hydrazinocarbonyl]-heptyl}-formamide;
N-Hydroxy-N-[(R)-2-(N'-{2-oxo-1-[2-(5,6,7,8-tetrahydro-[1,8]naphthyridin-2-yl)-ethyl]-dihydro-pyridin-4-yl}-hydrazinocarbonyl)-heptyl]-formamide;
N-{(R)-2-[N'-(4,6-Bis-ethylamino-[1,3,5]triazin-2-yl)-hydrazinocarbonyl]-heptyl}-N-hydroxy-formamide;
N-{(R)-2-[N'-(Bis-dimethylamino-[1,3,5]triazin-2-yl)-hydrazinocarbonyl]-heptyl}-N-hydroxy-formamide;
N-{(R)-2-[N'-(4,6-Di-morpholin-4-yl-[1,3,5]triazin-2-yl)-hydrazinocarbonyl]-heptyl}-N-hydroxy-formamide;
N-Hydroxy-N-((R)-2-{N'-[4-(4-methyl-piperazin-1-yl)-6-propylamino-[1,3,5]triazin-2-yl]-hydrazinocarbonyl}-heptyl)-formamide;
N-{(R)-2-[N'-(Dimethylamino-morpholin-4-yl-[1,3,5]triazin-2-yl)-hydrazinocarbonyl]-heptyl}-N-hydroxy-formamide;
N-Hydroxy-N-{(R)-2-[N'-(6-methyl-pyridin-2-yl)-hydrazinocarbonyl]-heptyl}-formamide;
N-Hydroxy-N-((R)-2-{N'-[5-(5-phenyl-[1,3,4]oxadiazol-2-yl)-pyridin-2-yl]-hydrazinocarbonyl}-heptyl)-formamide;
N-{(R)-2-[N'-(7-tert-Butyl-1,4-dioxo-1,2,3,4-tetrahydropyrido[3,4-d]pyridazin-5-yl)-hydrazinocarbonyl]-heptyl}-N-hydroxy-formamide;
N-((R)-2-{N'-[4-Ethylamino-6-(4-methyl-[1,4]diazepan-1-yl)-[1,3,5]triazin-2-yl]-hydrazinocarbonyl}-heptyl)-N-hydroxy-formamide;
N-((R)-2-{N'-[4-Ethylamino-6-(4-ethyl-piperazin-1-yl)-[1,3,5]triazin-2-yl]-hydrazinocarbonyl}-heptyl)-N-hydroxy-formamide;
N-Hydroxy-N-{(R)-2-[N'-(6-trifluoromethyl-pyridin-2-yl)-hydrazinocarbonyl]-heptyl}-formamide;
N-Hydroxy-N-{(R)-2-[N'-(4-methyl-6-morpholin-4-yl-methyl-pyrimidin-2-yl) hydrazinocarbonyl]-heptyl}-formamide;
N-Hydroxy-N-{(R)-2-[N'-(4-methyl-6-morpholin-4-yl-[1,3,5]triazin-2-yl)-hydrazinocarbonyl]-heptyl}-formamide;
N-Hydroxy-N-{(2R)-2-(cyclopentylmethyl)-3-[N'-(4,6-dimethyl-2-pyrimidinyl)-hydrazino]-3-oxopropyl}-formamide;
N-Hydroxy-N-{(R)-2-[N'-(4-methyl-6-pyrrolidin-1-yl-methyl-pyrimidin-2-yl)-hydrazinocarbonyl]-heptyl}-formamide;
N-{(R)-2-[N'-(4-Dimethylaminomethyl-6-methyl-pyrimidin-2-yl)-hydrazinocarbonyl]-heptyl}-N-hydroxy-formamide;
N-Hydroxy-N-((R)-2-{N'-[4-methyl-6-(4-methyl-piperazin-1-yl-methyl)-pyrimidin-2-yl]-hydrazinocarbonyl}-heptyl)-formamide;
N-Hydroxy-N-{(R)-2-[N'-(5-methyl-pyridin-2-yl)-hydrazinocarbonyl]-heptyl}-formamide;
N-((R)-2-{N'-[Dimethylamino-(4-methyl-[1,4]diazepan-1-yl)-[1,3,5]triazin-2-yl]-hydrazinocarbonyl}-heptyl)-N-hydroxy-formamide;
N-Hydroxy-N-{(R)-2-[N'-(4-methyl-6-pyrrolidin-1-yl-[1,3,5]triazin-2-yl)-hydrazinocarbonyl]-heptyl}-formamide;
N-Hydroxy-N-((R)-2-{N'-[4-methyl-6-)4-pyrrolidin-1-yl-piperidin-1-yl)-[1,3,5]triazin-2-yl]-hydrazinocarbonyl}-heptyl)-formamide;
N-((R)-2-{N'[(Ethyl-methyl-amino)-methyl-[1,3,5]triazin-2-yl]-hydrazinocarbonyl}-heptyl)-N-hydroxy-formamide;
N-((R)-2-{N'-[(4-(4-Ethyl-piperazin-1-yl)-6-methyl-[1,3,5]triazin-2-yl]-hydrazinocarbonyl}-heptyl)-N-hydroxy-formamide;
N-Hydroxy-N-[(2R)-7,7,7-trifluoro-2-({N'-[4-(trifluoromethyl)-pyrimidin-2-yl]-hydrazino}-carbonyl)-heptyl]-formamide;
N-Hydroxy-N-{(R)-2-[N'-(4-methylamino-6-morpholin-4-yl-[1,3,5]-2-yl)-hydrazinocarbonyl]-heptyl}-formamide;
N-((R)-2-{N'-[4-(4-Ethyl-piperazin-1-yl)-6-methylamnino-[1,3,5]triazin-2-yl]-hydrazinocarbonyl}-heptyl)-N-hydroxy-formamide;
N-{(R)-2-[N'-(4-Ethylamino-6-morpholin-4-yl-[1,3,5]triazin-2-yl)-hydrazinocarbonyl]-heptyl}-N-hydroxy-formamide;
N-Hydroxy-N-{(R)-2-[N'-(4,6,7-trimethyl-7,8-dihydropterin-2-yl)-hydrazinocarbonyl]-heptyl}-formamide;
N-Hydroxy-N-{(R)-2-[N'-(4,6,7-trimethyl-pteridin-2-yl)-hydrazinocarbonyl]-heptyl}-formamide;

N-Hydroxy-N-{(R)-2-[N'-(methoxymethoxymethyl-trifluoromethyl-pyrimidin-2-yl)-hydrazinocarbonyl]-heptyl}-formamide;
N-Hydroxy-N-((R)-2-{N'-[4-methyl-6-(1-piperidin-1-yl-methanoyl)-pyrimidin-2-yl]-hydrazinocarbonyl}-heptyl)-formamide;
2-(N'-{(R)-2-[(Formyl-hydroxy-amino)-methyl]-heptanoyl}-hydrazino)-6-methyl-pyrimidine-4-carboxylic acid cyclopropylamide;
2-(N'-{(R)-2-[(Formyl-hydroxy-amino)-methyl]-heptanoyl}-hydrazino)-6-methyl-pyrimidine-4-carboxylic acid diisopropylamide;
N-{(R)-2-[N'-(5-Cyano-pyridin-2-yl)-hydrazinocarbonyl]-heptyl}-N-hydroxy-formamide;
N-{(R)-2-[N'-(4,6-Diethyl-[1,3,5]triazin-2-yl)-hydrazinocarbonyl]-heptyl}-N-hydroxy-formamide;
N-{(R)-4-Cyclopentyl-2-[N'-(7-methyl-benzo[1,2,4]triazin-3-yl)-hydrazinocarbonyl]-butyl}-N-hydroxy-formamide;
N-{(R)-4-Cyclopentyl-2-[N'-(5-methyl-benzo[1,2,4]triazin-3-yl)-hydrazinocarbonyl]-butyl}-N-hydroxy-formamide;
N-Hydroxy-N-((R)-2-{N'-[6-(4-methyl-piperazin-1-yl-methyl)-pyridin-2-yl]-hydrazinocarbonyl}-heptyl)-formamide;
N-((R)-2-{N'-[5-(4,6-Dimethoxy-pyrimidin-2-yl)-pyridin-2-yl]-hydrazinocarbonyl}-heptyl)-N-hydroxy-formamide;
N-{(R)-2-[N'-(Diethylamino-methyl-[1,3,5]triazin-2-yl)-hydrazinocarbonyl]-heptyl}-N-hydroxy-formamide;
N-Hydroxy-N-[(R)-2-(N'-{[(2-methoxy-ethyl)-methyl-amino]-methyl-[1,3,5]triazin-2-yl}-hydrazinocarbonyl)-heptyl]-formamide;
N-((R)-1-{N'-[4-(2,6-Dimethyl-morpholin-4-yl)-6-methyl-[1,3,5]triazin-2-yl]-hydrazinocarbonyl}-heptyl)-N-hydroxy-formamide;
N-{(R)-2-[N'-(5-Fluoro-4methyl-6-morpholin-4-yl-pyrimidin-2-yl)-hydrazinocarbonyl]-heptyl }-N-hydroxy-formamide;
N-{(R)-2-[N'-(Ethyl-methyl-amino)-[1,3,5]triazin-2-yl)-hydrazinocarbonyl]-heptyl}-N-hydroxy-formamide;
N-((R)-2-{N'-[4-Ethyl-6-(4-ethyl-piperazin-1-yl)-[1,3,5]triazin-2-yl]-hydrazinocarbonyl}-heptyl)-N-hydroxy-formamide;
N-((R)-2-{N'-[5-Fluoro-4-methyl-6-(4-methyl-piperazin-1-yl)-pyrimidin-2-yl]-hydrazinocarbonyl}-heptyl)-N-hydroxy-formamide;
N-{(R)-2-[N'-(Dimethylamino-ethyl-[1,3,5]triazin-2-yl)-hydrazinocarbonyl]-heptyl}-N-hydroxy-formamide;
N-((R)-2-{N'-[5-Fluoro-4-methyl-6-(4-methyl-[1,4]diazepan-1-yl)-pyrimidin-2-yl]-hydrazinocarbonyl}-heptyl)-N-hydroxy-formamide;
N-{(R)-4-Cyclopentyl-2-N'-(morpholin-4-yl-trifluoromethyl-pyrimidin-2-yl)-hydrazinocarbonyl]-butyl}-N-hydroxy-formamide;
N-[(R)-2-(N'-{Ethyl-[(2-methoxy-ethyl)-methyl-amino]-[1,3,5]triazin-2-yl}-hydrazinocarbonyl)-heptyl]-N-hydroxy-formamide;
N-{(R)-2-[N'-(Dimethylamino-methyl-pyrimidin-2-yl)-hydrazinocarbonyl]-heptyl}-N-hydroxy-formamide;
N-{(R)-2-[N'-(4-Cyclopropylamino-6-methyl-pyrimidin-2-yl)-hydrazinocarbonyl]-heptyl}-N-hydroxy-formamide;
N-{(R)-2-Cyclohexyl-2-[N'-(4-trifluoromethyl-pyrimidin-2-yl)-hydrazinocarbonyl]-ethyl}-N-hydroxy-formamide;
N-{(R)-2-Cyclohexyl-2-[N'-(7-methoxy-benzo[1,2,4]triazin-3-yl)-hydrazinocarbonyl]-ethyl}-N-hydroxy-formamide;
N-{(R)-2-Cyclohexyl-2-[N'-(5-methyl-benzo[1,2,4]triazin-3-yl)-hydrazinocarbonyl]-ethyl}-N-hydroxy-formamide;
N-{(R)-4,4-Dimethyl-2-[N'-(4-trifluoromethyl-pyrimidin-2-yl)-hydrazinocarbonyl]-pentyl}-N-hydroxy-formamide;
N-{(R)-4,4-Dimethyl-2-[N'-(7-methyl-benzo[1,2,4]triazin-3-yl)-hydrazinocarbonyl]-pentyl}-N-hydroxy-formamide;
N-{(R)-4,4-Dimethyl-2-[N'-(5-methyl-benzo[1,2,4]triazin-3-yl)-hydrazinocarbonyl]-pentyl}-N-hydroxy-formamide;
N-{(R)-4,4-Dimethyl-2-[N'-(morpholin-4-yl-trifluoromethyl-pyrimidin-2-yl)-hydrazinocarbonyl]-pentyl}-N-hydroxy-formamide;
N-((R)-2-{N'-[Ethyl-(methyl-pyridin-2-yl-amino)-[1,3,5]triazin-2-yl]-hydrazinocarbonyl}-heptyl)-N-hydroxy-formamide;
N-{(R)-2-[N'-(4-Cyclopropylamino-6-ethyl-[1,3,5]triazin-2-yl)-hydrazinocarbonyl]-heptyl}-N-hydroxy-formamide;
N-Hydroxy-N-[(R)-2-[N'-(5-methyl-benzo[1,2,4]triazin-3-yl)-hydrazinocarbonyl]-3-(1-methyl-cyclopentyl)-propyl]-formamide;
N-Hydroxy-N-[(R)-2-[N'-(7-methoxy-benzo[1,2,4]triazin-3-yl)-hydrazinocarbonyl]-3-(1-methyl-cyclopentyl)-propyl]-formamide;
N-Hydroxy-N-{(R)-3-(1-methyl-cyclopentyl)-2-[N'-(4-trifluoromethyl-pyrimidin-2-yl)-hydrazinocarbonyl]-propyl}-formamide;
N-Hydroxy-N-{(R)-2-[N'-(4-isopropyl-6-morpholin-4-yl-[1,3,5]triazin-2-yl)-hydrazinocarbonyl]-heptyl}-formamide;
N-Hydroxy-N-{(2R)-2-(cyclopentylmethyl)-3-[N'-(4-methyl-2-pyrimidinyl)-hydrazino]-3-oxopropyl}-formamide;
N-Hydroxy-N-[(2R)-6,6,6-trifluoro-2-({N'-[4-(trifluoromethyl)-pyrimidin-2-yl]-hydrazino}-carbonyl)-hexyl]-formamide;
N-{(R)-2-[N'-(5,7-Dimethyl-benzo[1,2,4]triazin-3-yl)-hydrazinocarbonyl]-heptyl}-N-hydroxy-formamide;
N-{(R)-2-[N'-(3,6-Dimethyl-pyrazin-2-yl)-hydrazinocarbonyl]-heptyl}-N-hydroxy-formamide;
N-((R)-2-{N'-[4-(4-Ethyl-piperazine-1-yl)-6-isopropyl-[1,3,5]triazin-2-yl]-hydrazinocarbonyl}-heptyl)-N-hydroxy-formamide;
N-{(R)-2-[N'-(4-Dimethylamino-6-isopropyl-[1,3,5]triazin-2-yl)-hydrazinocarbonyl]-heptyl}-N-hydroxy-formamide;
N-Hydroxy-N-{(R)-2-[N'-(methyl-trifluoromethyl-pyridin-2-yl)-hydrazinocarbonyl]-heptyl}-formamide;
2-(N'-{(R)-2-[(Formyl-hydroxy-amino)-methyl]-heptanoyl}-hydrazino)-6,N,N-trimethyl-isonicotinamide;
N-Hydroxy-N[(2R)-2-({N'-[3-amino-6-(trifluoromethyl)-pyridin-2-yl]-hydrazino}-carbonyl)-heptyl]-formamide;
N-Hydroxy-N-{(R)-2-[N'-(4-morpholin-4-yl-6-propyl-[1,3,5]triazin-2-yl)-hydrazinocarbonyl]-heptyl}-formamide;
N-((R)-2-{N'-[4-(4-Ethyl-piperazin-1-yl)-6-propyl-[1,3,5]triazin-2-yl]-hydrazinocarbonyl}-heptyl)-N-hydroxy-formamide;

N-{(R)-5,5-Dimethyl-2-[N'(4-trifluoromethyl-pyrimidin-2-yl)-hydrazinocarbonyl]-hexyl}-N-hydroxy-formamide;

N-{(R)-5,5-Dimethyl-2-[N'-(7-methyl-benzo[1,2,4]triazin-3-yl)-hydrazinocarbonyl]-hexyl}-N-hydroxy-formamide;

N-{(R)-5,5-Dimethyl-2-[N'-(5-methyl-benzo[1,2,4]triazin-3-yl)-hydrazinocarbonyl]-hexyl}-N-hydroxy-formamide;

N-{(R)-5,5-Dimethyl-2-[N'(morpholin-4-yl-trifluoromethyl-pyrimidin-2-yl)-hydrazinocarbonyl]-hexyl}-N-hydroxy-formamide;

N-{(R)-4-Ethyl-2-[N'-(4trifluoromethyl-pyrimidin-2-yl)-hydrazino carbonyl]-hexyl}-N-hydroxy-formamide;

N-{(R)-4-Ethyl-2-[N'-(7-methyl-benzo[1,2,4]triazin-3-yl)-hydrazinocarbonyl]-hexyl}-N-hydroxy-formamide;

N-{(R)-4-Ethyl-2-[N'-(morpholin-4-yl-trifluoromethyl-pyrimidin-2-yl)-hydrazinocarbonyl]-hexyl}-N-hydroxy-formamide;

N-{(R)-4-Ethyl-2-[N'-(5-methyl-benzo[1,2,4]triazin-3-yl)-hydrazinocarbonyl]-hexyl}-N-hydroxy-formamide;

N-Hydroxy-N-[(R)-2-(N'-{[(2-methoxy-ethyl)-methyl-amino]-propyl-[1,3,5]triazin-2-yl}-hydrazinocarbonyl)-heptyl]-formamide;

N-{(R)-2-[N'-(4-Ethyl-pyrimidin-2-yl)-hydrazinocarbonyl]-heptyl}-N-hydroxy-formamide;

N-Hydroxy-N-{(R)-2-[N'-(4-isopropyl-pyrimidin-2-yl)-hydrazinocarbonyl]-heptyl}-formamide;

N-Hydroxy-N-[(2R)-2-({N'-[4(pyridin-2-yl)-pyrimidin-2-yl]-hydrazino}-carbonyl)-heptyl]-formamide;

N-{(R)-2-[N'-(4,6-Dicyclopropyl-[1,3,5]triazin-2-yl)-hydrazinocarbonyl]-heptyl}-N-hydroxy-formamide;

N-Hydroxy-N-[(R)-2-[N'-(5-methyl-benzo[1,2,4]triazin-3-yl)-hydrazinocarbonyl]-3-(2-methyl-cyclopentyl)-propyl]-formamide;

N-[(R)-2-[N'-(Dimethylamino-ethyl-[1,3,5]triazin-2-yl)-hydrazinocarbonyl]-3-(2-methyl-cyclopentyl)-propyl]-N-hydroxy-formamide;

N-Hydroxy-N-[(R)-2-[N'-(4-trifluoromethyl-pyrimidin-2-yl)-hydrazinocarbonyl]-3-(2-methyl-cyclopentyl)-propyl]-formamide;

N-{(R)-2-[N'-(5-Ethyl-pyrimidin-2-yl)-hydrazinocarbonyl]-heptyl}-N-hydroxy-formamide;

N-((R)-2-{N'-[4-Ethyl-6-(4-isopropyl-piperazin-1-yl)-[1,3,5]triazin-2-yl]-hydrazinocarbonyl}-heptyl)-N-hydroxy-formamide;

N-{(R)-4,4-Dimethyl-2-[N'-(4-trifluoromethyl-pyrimidin-2-yl)-hydrazinocarbonyl]-hexyl}-N-hydroxy-formamide;

N-{(R)-4,4-Dimethyl-2-[N'-(7-methyl-benzo[1,2,4]triazin-3-yl)-hydrazinocarbonyl]-hexyl}-N-hydroxy-formamide;

N-{(R)-4,4-Dimethyl-2-[N'-(5-methyl-benzo[1,2,4]triazin-3-yl)-hydrazinocarbonyl]-hexyl}-N-hydroxy-formamide;

N-{(R)-4,4-Dimethyl-2-[N'-(morpholin-4-yl-trifluoromethyl-pyrimidin-2-yl)-hydrazinocarbonyl]-hexyl}-N-hydroxy-formamide;

N-Hydroxy-N-{(R)-2-[N'-(5-phenyl-[1,2,4]triazin-3-yl)-hydrazinocarbonyl]-heptyl}-formamide;

N-{(R)-2-[N'(5-Ethyl-4-methyl-pyrimidin-2-yl)-hydrazinocarbonyl]-heptyl}-N-hydroxy-formamide;

N-((R)-2-{N'-[4Ethyl-6-(4-propyl-piperazin-1-yl)-[1,3,5]triazin-2-yl]-hydrazinocarbonyl}-heptyl)-N-hydroxy-formamide;

N-Hydroxy-N-((R)-2-{N'-[6-(4-pyrimidin-2-yl-piperazin-1-yl-methyl)-pyridin-2-yl]-hydrazinocarbonyl}-heptyl)-formamide;

N-Hydroxy-N-((R)-2-{N'-[6-(3-[1,2,4]triazol-1-yl-methyl-[1,2,4]triazol-1-yl)-pyridin-2-yl]-hydrazinocarbonyl}-heptyl)-formamide;

N-{(R)-3-Bicyclo[2.2.1]hept-7-yl-2-[N'-(4-trifluoromethyl-pyrimidin-2-yl)-hydrazinocarbonyl]-propyl}-N-hydroxy-formamide;

N-{(R)-3-Bicyclo[2.2.1]hept-7-yl-2-[N'-(morpholin-4-yl-trifluoromethyl-pyrimidin-2-yl)-hydrazinocarbonyl]-propyl}-N-hydroxy-formamide;

N-hydroxy-N-[(R)-2-(N'-pyridin-3-yl-hydrazinocarbonyl)-heptyl]-formamide;

4-{4-Ethyl-6-[2-((2R)-2-{[formyl(hydroxy)amino]-methyl}-heptanoyl)-hydrazino]-1,3,5-triazin-2-yl}-1-methyl-1-propylpiperazin-1-ium iodide;

N-{(R)-3-Bicyclo[2.2.1]hept-7-yl-2-[N'-(5-methyl-benzo[1,2,4]triazin-3-yl)-hydrazinocarbonyl]-propyl}-N-hydroxy-formamide;

N-{(R)-2-[N'-(4-Azetidin-1-yl-6-ethyl-[1,3,5]triazin-2-yl)-hydrazinocarbonyl]-heptyl}-N-hydroxy-formamide;

N-{(R)-2-Cyclopentyl-2-[N'-(4-trifluoromethyl-pyrimidin-2-yl)-hydrazinocarbonyl]-ethyl}-N-hydroxy-formamide;

N-{(R)-2-Cyclopentyl-2-[N'-(4-methyl-pyridin-2-yl)-hydrazinocarbonyl]-ethyl}-N-hydroxy-formamide;

N-{(R)-2-Cyclopentyl-2-[N'-(dimethylamino-ethyl-[1,3,5]triazin-2-yl)-hydrazinocarbonyl]-ethyl}-N-hydroxy-formamide;

N-{(R)-2-Cyclopentyl-2-[N'-(7-methyl-benzo[1,2,4]triazin-3-yl)-hydrazinocarbonyl]-ethyl}-N-hydroxy-formamide;

N-{(R)-2-Cyclopentyl-2-[N'-(5-methyl-benzo[1,2,4]triazin-3-yl)-hydrazinocarbonyl]-ethyl}-N-hydroxy-formamide;

N-Hydroxy-N-{(R)-2-[N'-(5-methyl-benzo[1,2,4]triazin-3-yl)-hydrazinocarbonyl]-2-(4-methyl-cyclohexyl)-ethyl}-formamide;

N-Hydroxy-N-{(R)-2-[N'-(7-methyl-benzo[1,2,4]triazin-3-yl)-hydrazinocarbonyl]-2-(4-methyl-cyclohexyl)-ethyl}-formamide;

N-Hydroxy-N-{(R)-2-(4-methyl-cyclohexyl)-2-[N'-(4-trifluoromethyl-pyrimidin-2-yl)-hydrazinocarbonyl]-ethyl}-formamide;

N-Hydroxy-N-{(R)-2-(4-methyl-cyclohexyl)-2-[N'-(morpholin-4-yl-trifluoromethyl-pyrimidin-2-yl)-hydrazinocarbonyl]-ethyl}-formamide;

N-Hydroxy-N-{(R)-2-(4-methyl-cyclohexyl)-2-[N'-(4-methyl-pyridin-2-yl)-hydrazinocarbonyl]-ethyl}-formamide;

N-{(R)-2-[N'-(6,7-Dihydro-5H-cyclopentapyrimidin-2-yl)-hydrazinocarbonyl]-heptyl}-N-hydroxy-formamide;

N-((R)-2-[N'-[4-Ethyl-6-((S)-2-hydroxymethyl-pyrrolidin-1-yl)-[1,3,5]triazin-2-yl]-hydrazinocarbonyl]-heptyl)-N-hydroxy-formamide;

N-{(R)-2-[N'-(Dimethylamino-pyridin-3-yl-pyrimidin-2-yl)-hydrazinocarbonyl]-heptyl}-N-hydroxy-formamide;

N-{(R)-2-[N'-(Dimethylamino-pyridin-4-yl-pyrimidin-2-yl)-hydrazinocarbonyl]-heptyl}-N-hydroxy-formamide;

N-Hydroxy-N-{(R)-2-N'-(5,6,7,8-tetrahydro-benzo[1,2,4]triazin-3-yl)-hydrazinocarbonyl]-heptyl}-formamide;

N-{(R)-2-[N'-(5,6-Diethyl-[1,2,4]triazin-3-yl)-hydrazinocarbonyl]-heptyl}-N-hydroxy-formamide;
N-Hydroxy-N-{(R)-2-[N'-[5-(4-hydroxy-phenyl)-[1,2,4]triazin-3-yl]-hydrazinocarbonyl]-heptyl)-formamide;
N-[(R)-2-(N'-{[(2-Dimethylamino-ethyl)-methyl-amino]-ethyl-[1,3,5]triazin-2-yl}-hydrazinocarbonyl)-heptyl]-N-hydroxy-formamide;
N-{(R)-2-[N'-(2-Dimethylamino-quinazolin-4-yl)-hydrazinocarbonyl]-heptyl}-N-hydroxy-formamide;
N-Hydroxy-N-{(R)-2-[N'-(3-methanesulfonyl-4,6-dimethyl-pyridin-2-yl)-hydrazinocarbonyl]-heptyl}-formamide;
N-((R)-2-{N'-[4-Ethyl-6-(3-hydroxy-piperidin-1-yl)-[1,3,5]triazin-2-yl]-hydrazinocarbonyl}-heptyl)-N-hydroxy-formamide;
N-[(R)-2-(N'-[4,5]Bipyrimidinyl-2-yl-hydrazinocarbonyl)-heptyl]-N-hydroxy-formamide;
N-((R)-2-{N'-[4-Ethyl-6-((R)-3-hydroxy-pyrrolidin-1-yl)-[1,3,5]triazin-2-yl]-hydrazinocarbonyl}-heptyl)-N-hydroxy-formamide;
N-Hydroxy-N-[(R)-2-(N'-[3,3]Bipyridinyl-5-yl-hydrazinocarbonyl)-heptyl]-formamide;
N-Hydroxy-N-[(R)-2-(N'-(5-morpholin-4-yl-pyridin-3-yl)-hydrazinocarbonyl)-heptyl]-formamide;
N-Hydroxy-N-{(R)-2-[N(4-pyridin-3-yl-pyrimidin-2-yl)-hydrazinocarbonyl]-heptyl}-formamide;
N-Hydroxy-N-{(R)-2-[N'-(5,6,7,8-tetrahydro-quinazolin-2-yl)-hydrazinocarbonyl]-heptyl}-formamide;
N-[(R)-2-(N'-{[Cyclopropyl-1-(1-methyl-piperidin-4-yl)-amino]-ethyl-[1,3,5]triazin-2-yl}-hydrazinocarbonyl)-heptyl]-N-hydroxy-formamide;
N-((R)-2-{N'-[4-((R)-3-Dimethylamino-pyrrolidin-1-yl)-6-ethyl-[1,3,5]triazin-2-yl]-hydrazinocarbonyl}-heptyl)-N-hydroxy-formamide;
N-Hydroxy-N-[(R)-2-(N'-[5-(1H-pyrrol-2-yl)-pyridin-3-yl]-hydrazinocarbonyl)-heptyl]-formamide;
N-Hydroxy-N-[(R)-2-(N'-[(4-methyl-piperazin-1-yl)-trifluoromethyl-pyirimdin-4-yl]-hydrazinocarbonyl)-heptyl]-formamide;
N-Hydroxy-N-[(R)-2-(N'-[(5-Furan-3-yl-pyridin-3-yl)-hydrazinocarbonyl)-heptyl]-formamide;
N-{(R)-5,5-Dimethyl-2-[N'-(4-trifluoromethyl-pyrimidin-2-yl)-hydrazinocarbonyl]-heptyl}-N-hydroxy-formamide;
N-{(R)-5,5-Dimethyl-2-[N'-(7-methyl-benzo[1,2,4]triazin-3-yl)-hydrazinocarbonyl]-heptyl}-N-hydroxy-formamide;
N-{(R)-5,5-Dimethyl-2-(4-methyl-pyridin-2-yl)-hydrazinocarbonyl]-heptyl}-N-hydroxy-formamide;
N-{(R)-2-Cycloheptyl-2-[N'-(4-trifluoromethyl-pyrimidin-2-yl)-hydrazinocarbonyl]-ethyl}-N-hydroxy-formamide;
N-{(R)-2-Cycloheptyl-2-[N'-(4-methyl-pyridin-2-yl)-hydrazinocarbonyl]-ethyl}-N-hydroxy-formamide;
N-{(R)-2-Cycloheptyl-2-[N'-(7-methyl-benzo[1,2,4]triazin-3-yl)-hydrazinocarbonyl]-ethyl}-N-hydroxy-formamide;
N-((R)-2-{N'-[4-Ethyl-6-(4-hydroxy-piperidin-1-yl)-[1,3,5]triazin-2-yl]-hydrazinocarbonyl}-heptyl)-N-hydroxy-formamide;
N-{(R)-5,5-Dimethyl-2-[N'-(5-methyl-benzo[1,2,4]triazin-3-yl)-hydrazinocarbonyl]-heptyl}-N-hydroxy-formamide;
N-{(R)-2-[N'-(4-Dimethylamino-quinazolin-2-yl)-hydrazinocarbonyl]-heptyl}-N-hydroxy-formamide;
N-Hydroxy-N-{(R)-2-[N'-(4-pyridin-4yl-pyrimidin-2-yl)-hydrazinocarbonyl]-heptyl}-formamide;
N-Hydroxy-N-((R)-2-{N'-[4-(3-hydroxymethyl-phenyl)-pyrimidin-2-yl]-hydrazinocarbonyl}-heptyl)-formamide;
N-Hydroxy-N-((R)-2-{N'-[4-(4-hydroxymethyl-phenyl)-pyrimidin-2-yl]-hydrazinocarbonyl}-heptyl)-formamide;
N-((R)-2-{N'-[4-Ethyl-6-(3-methoxy-piperidin-1-yl)-[1,3,5]triazin-2-yl]-hydrazinocarbonyl}-heptyl)-N-hydroxy-formamide;
N-Hydroxy-N-{(R)-2-[N'-(7-methyl-benzo[1,2,4]triazin-3-yl)-hydrazinocarbonyl]-2-(4-methyl-cyclohexyl)-ethyl}-formamide;
N-[(R)-2-{N'-[Ethyl-(ethyl-methylamino)-[1,3,5]triazin-2-yl]-hydrazinocarbonyl}-2-(4-methyl-cyclohexyl)-ethyl]-N-hydroxy-formamide;
N-[(R)-2-{N'-[Ethyl-(ethyl-methylamino)-[1,3,5]triazin-2-yl]-hydrazinocarbonyl}-2-(4-methyl-cyclohexyl)-ethyl]-N-hydroxy-formamide;
N-Hydroxy-N-{(R)-2-[N'-(7-methyl-benzo[1,2,4]triazin-3-yl)-hydrazinocarbonyl]-2-(4-methyl-cyclohexyl)-ethyl}-formamide;
N-((R)-2-{N'-[4-(2,6-Dimethoxy-phenyl)-pyrimidin-2-yl]-hydrazinocarbonyl}-heptyl)-N-hydroxy-formamide;
N-((R)-2-{N'-[4-Ethyl-6-((R)-3-methoxy-pyrrolidin-1-yl)-[1,3,5]triazin-2-yl]-hydrazinocarbonyl}-heptyl)-N-hydroxy-formamide;
N-((R)-2-{N'-[4-Ethyl-6-(4-methoxy-piperidin-1-yl)-[1,3,5]triazin-2-yl]-hydrazinocarbonyl}-heptyl)-N-hydroxy-formamide;
N-Hydroxy-N-[(R)-2-(N'-(6-pyrrolidin-1-yl-pyrimidin-4-yl)-hydrazinocarbonyl)-heptyl]-formamide;
N-Hydroxy-N-[(R)-2-(N'-[6-(4-methyl-piperazin-1-yl)-pyrimidin-4-yl])-hydrazinocarbonyl)-heptyl]-formamide;
N-{(R)-2-[N'-(6-Dimethylamino-pyrimidin-4-yl)-hydrazinocarbonyl]-heptyl}-N-hydroxy-formamide;
N-{(R)-2-[N'-(Pyridin-4-yl-trifluoromethyl-pyrimidin-4-yl)-hydrazinocarbonyl]-heptyl}-N-hydroxy-formamide;
N-{(R)-2-[N'-(Pyridin-3-yl-trifluoromethyl-pyrimidin-4-yl)-hydrazinocarbonyl]-heptyl}-N-hydroxy-formamide;
N-{(R)-2-[N'-(2-Ethylamino-6-trifluoromethyl-pyrimidin-4-yl)-hydrazinocarbonyl]-heptyl}-N-hydroxy-formamide;
N-Hydroxy-N-((R)-2-{N'-[5-(4-methoxy-phenyl)-[1,2,4]triazin-3-yl]-hydrazinocarbonyl}-heptyl)-formamide;
N-Hydroxy-N-((R)-2-{N'-[4-(2,3,4-trimethoxy-phenyl)-pyrimidin-2-yl]-hydrazinocarbonyl}-heptyl)-formamide;
N-{(R)-4,4-Dimethyl-2-[N'-(4-trifluoromethyl-pyrimidin-2-yl)-hydrazinocarbonyl]-heptyl}-N-hydroxy-formamide;
N-{(R)-4,4-Dimethyl-2-[N'-(7-methyl-benzo[1,2,4]triazin-3-yl)-hydrazinocarbonyl]-heptyl}-N-hydroxy-formamide;
N-{(R)-4,4-Dimethyl-2-[N'-(5-methyl-benzo[1,2,4]triazin-3-yl)-hydrazinocarbonyl]-heptyl}-N-hydroxy-formamide;
N-{(R)-4,4-Dimethyl-2-[N'-(4-methyl-pyridin-2-yl)-hydrazinocarbonyl]-heptyl}-N-hydroxy-formamide;
N-Hydroxy-N-{(R)-2-[N'-(6-morpholin-4-yl-pyrimidin-4-yl)-hydrazinocarbonyl]-heptyl}-formamide;
N-Hydroxy-N-[(R)-2-(N'-{5-[4-(2-hydroxy-ethoxy)-phenyl]-[1,2,4]triazin-3-yl}-hydrazinocarbonyl)-heptyl]-formamide;

N-((R)-2-{N'-[4-(3,5-Dimethyl-isoxazol-4-yl)-pyrimidin-2-yl]-hydrazinocarbonyl}-heptyl)-N-hydroxy-formamide;

N-Hydroxy-N-{(R)-2-[N'-(4-methyl-1-oxy-pyridin-2-yl)-hydrazinocarbonyl]-heptyl}-formamide;

2-(N'-{(R)-2-[(Formyl-hydroxy-amino)-methyl]-heptanoyl}-hydrazino)-6-methyl-nicotinic acid;

N-Hydroxy-N-{(R)-2-[N'-(3-methoxy-pyridin-2-yl)-hydrazinocarbonyl]-heptyl}-formamide;

N-Hydroxy-N-{(2R)-2-[(N'-{4-[4-(methylsulfonyl)phenyl]-pyrimidin-2-yl}-hydrazino)-carbonyl]-heptyl}-formamide;

N-[(2R)-2-({N'-[4-(2-aminophenyl)-pyrimidin-2-yl]-hydrazino}-carbonyl)-heptyl]-N-hydroxy-formamide;

N-Hydroxy-N-[(2R)-2-({N'-[5-(5-methyl-1,3,4-oxadiazol-2-yl)-4-(trifluoromethyl)-pyrimidin-2-yl]-hydrazino}-carbonyl)-heptyl]-formamide;

N-Hydroxy-N-((2R)-2-(cyclopentylmethyl)-3-{N'-[5-(5-methyl-1,3,4-oxadiazol-2-yl)-4-(trifluoromethyl)-pyrimidin-2-yl]-hydrazino}-3-oxopropyl)-formamide;

N-[(2R)-2-({N'-[6-(dimethylamino)-2-methyl-pyrimidin-4-yl]-hydrazino}-carbonyl)-heptyl]-N-hydroxy-formamide;

N-[(2R)-2-({N'-[2-Cyclopropyl-6-(dimethylamino)-pyrimidin-4-yl]-hydrazino}-carbonyl)-heptyl]-N-hydroxy-formamide;

N-Hydroxy-N-[(2R)-4-(2-thienyl)-2-({N'-[4-(trifluoromethyl)-pyrimidin-2-yl]-hydrazino}-carbonyl)-butyl]-formamide;

N-Hydroxy-N-[(2R)-2-{[N'-(4-methyl-pyrimidin-2-yl)hydrazinolcarbonyl}-4-(2-thienyl)-butyl]-formamide;

N-[(2R)-2-[(N'-{4-Ethyl-6-[ethyl(methyl)amino]-1,3,5-triazin-2-yl}-hydrazino)-carbonyl]-4-(2-thienyl)butyl]-N-hydroxy-formamide;

N-Hydroxy-N-((2R)-3-oxo-2-(2-thienylmethyl)-3-{N'-[4-(trifluoromethyl)-pyrimidin-2-yl]-hydrazino}-propyl)-formamide;

N-Hydroxy-N-[(2R)-3-[N'-(4-methyl-pyrimidin-2-yl)hydrazino]-3-oxo-2-(2-thienylmethyl)-propyl]-formamide;

N-[(2R)-3-(N'-{4-Ethyl-6-[ethyl(methyl)amino]-1,3,5-triazin-2-yl}hydrazino)-3-oxo-2-(2-thienylmethyl)-propyl]-N-hydroxy-formamide;

N-Hydroxy-N-[(2R)-2-({N'-[2-methyl-6-(pyridin-2-yl)-pyrimidin-4-yl]-hydrazino}-carbonyl)-heptyl]-formamide;

N-Hydroxy-N-[(2R)-2-({N'-[6(pyridin-2-yl-methyl)-pyridazin-3-yl]-hydrazino}-carbonyl)-heptyl]-formamide;

N-Hydroxy-N-[(2R)-2-(({N'-[2-methyl-6-(morpholin-4-yl)-pyrimidin-4-yl]-hydrazino}-carbonyl)-heptyl]-formamide;

N-Hydroxy-N-[(2R)-2-({N'-[6-(morpholin-4-yl)-2-(trifluoromethyl)-pyrimidin-4-yl]-hydrazino}-carbonyl)-heptyl]-formamide;

N-Hydroxy-N-{(2R)-2-[(N'-{4-[methyl-(pyridin-2-yl)-amino]-pyrimidin-2-yl}-hydrazino)-carbonyl]-heptyl}-formamide;

N-Hydroxy-N-((2R)-2-(cyclopentylmethyl)-3-{N'-[4-cyclopropyl-6-(dimethylamino)-1,3,5-triazin-2-yl]-hydrazino}-3-oxopropyl)-formamide;

N-Benzo[1,3]dioxol-5-yl-methyl-hydrazinecarboxylic acid tert-butyl ester;

N-[(R)-2-(N'-Benzo[1,3]dioxol-5-yl-methyl-hydrazinocarbonyl)-heptyl]-N-hydroxy-formamide;

N-{(R)-2-[N'-(2,3-Dihydro-[1,4]dioxino[2,3-b]pyridin-7-yl-methyl)-hydrazinocarbonyl]-heptyl}-N-hydroxy-formamide;

N-{(R)-2-[N'-(4-Dimethylamino-benzyl)-hydrazinocarbonyl]-heptyl}-N-hydroxy-formamide;

N-Hydroxy-N-((R)-2-{N'-[2-(5,6,7,8-tetrahydro-[1,8]naphthyridin-2-yl)-ethyl]-hydrazinocarbonyl]-heptyl}-N-hydroxy-formamide;

N-Hydroxy-N-[(R)-2-(N'-quinolin-2-yl-methyl-hydrazinocarbonyl)-heptyl]-formamide;

N-Hydroxy-N-{(R)-2-[N'-(1,2,3,4-tetrahydro-quinolin-2-yl-methyl)-hydrazinocarbonyl]-heptyl}-formamide;

N-Hydroxy-N-[(R)-2-(N'-quinolin-6-yl-methyl-hydrazinocarbonyl)-heptyl]-formamide;

N-[(R)-2-(N'-Benzofuran-2-yl-methyl-hydrazinocarbonyl)-heptyl]-N-hydroxy-formamide;

N-{(R)-2-[N'-(6-Fluoro-4H-benzo[1,3]dioxin-8-yl-methyl)-hydrazinocarbonyl]-heptyl}-N-hydroxy-formamide;

N-Hydroxy-N-{(R)-2-[N'-(4-methoxy-benzyl)-hydrazinocarbonyl]-heptyl}-formamide;

N-Hydroxy-N-{(R)-2-[N'-(2-methoxy-benzyl)-hydrazinocarbonyl]-heptyl}-formamide;

N-Hydroxy-N-{(R)-2-[N'-(tetrahydro-furan-3-yl-methyl)-hydrazinocarbonyl]-heptyl}-formamide;

N-[(R)-2-(N'-Furan-3-yl-methyl-hydrazinocarbonyl)-heptyl]-N-hydroxy-formamide;

N-{(R)-2-[N'-(2,3-Dihydro-benzo[1,4]dioxin-6-yl-methyl)-hydrazinocarbonyl]-heptyl}-N-hydroxy-formamide;

N-{(R)-2-[N'-(2,3-Dihydro-benzo[1,4]dioxin-2-yl-methyl)-hydrazinocarbonyl]-heptyl}-N-hydroxy-formamide;

N-Hydroxy-N-{(R)-2-[N'-(2-phenoxy-ethyl)-hydrazinocarbonyl]-heptyl}-formamide;

N-{(R)-2-[N'-((S)-2,3-Dihydroxy-propyl)-hydrazinocarbonyl]-heptyl}-N-hydroxy-formamide;

N-Hydroxy-N-{(R)-2-[N'-(5-methyl-isoxazol-3-yl-methyl)-hydrazinocarbonyl]-heptyl}-formamide;

N-((R)-2-{N'-[1-(1-Benzo[1,3]dioxol-5-yl-methanoyl)-piperidin-4-yl]-hydrazinocarbonyl}-heptyl)-N-hydroxy-formamide;

N-((R)-2-{N'-[1-(1-Benzofuran-2-yl-methanoyl)-piperidin-4-yl]-hydrazinocarbonyl}-heptyl)-N-hydroxy-formamide;

N-Hydroxy-N-[(R)-2-(N'-{1-[1-(7-methoxy-benzofuran-2-yl)-methanoyl]-piperidin-4-yl}-hydrazinocarbonyl)-heptyl]-formamide;

N-{(R)-2-[N'-(1-Benzyl-piperidin-4-yl)-hydrazinocarbonyl]-heptyl}-N-hydroxy-formamide;

N-[(R)-2-(N'-{1-[1-(3,4-Dichloro-phenyl)-methanoyl]-piperidin-4-yl}-hydrazinocarbonyl)-heptyl]-N-hydroxy-formamide;

N-[(R)-2-(N'-{1-[1-(2,3-Dichloro-phenyl)-methanoyl]-piperidin-4-yl}-hydrazinocarbonyl)-heptyl]-N-hydroxy-formamide; or N-[(R)-2-(N'-Benzyl-hydrazinocarbonyl)-heptyl]-N-hydroxy-formamide; or a pharmaceutically acceptable salt thereof.

22. A compound according to claim 17 wherein R1 is a substituted pyridyl, substituted pyrimidyl or substituted triazinyl; or a pharmaceutically acceptable salt thereof 23. A compound according to claim 22 wherein R1 is pyridyl, pyrimidyl or triazinyl each of which is substituted by one or more of the following: heteroaryl; heterocyclic; aryl;

$C_{1-3}$ alkoxy optionally substituted by one to three F; acyl; sulfonyl; aminocarbonyl; carboxy; oxo; amino; cyano; halogen; or $C_{1-3}$ substituted alkyl;

wherein said $C_{1-3}$ substituted alkyl is substituted with at least one substituent selected from the group consisting of: $C_{1-3}$ alkyl optionally substituted by one to three fluorines; $C_{2-3}$ alkenyl; $C_{2-3}$ alkynyl; $C_{1-2}$ alkoxy optionally substituted by one to three fluorines; sulfanyl; sulfinyl; sulfonyl; oxo; hydroxy; mercapto; amino; guanidino; carboxy; aminocarbonyl; aryl; aryloxy; heteroaryl; heteroaryloxy; heterocyclic; aminosulfonyl; sulfonylamino; carboxyamide; ureido; nitro; cyano; and halogen.

24. A compound according to claim 23 wherein R is unsubstituted $C_{2-6}$ alkyl; unsubstituted $(CH_2)_n$-$C_{3-6}$ carbocycle; or unsubstituted $(CH_2)_n R4$, wherein R4 is thienyl;

Y represents $CH_2$ or a covalent bond; and n is an integer from 0 to 2; or a pharmaceutically acceptable salt thereof.

25. A compound according to claim 24 wherein R is unsubstituted $C_{2-6}$ alkyl; or a pharmaceutically acceptable salt thereof.

26. A compound according to claim 24 wherein R is unsubstituted $(CH_2)_n$—$C_{3-6}$ carbocycle; or a pharmaceutically acceptable salt thereof.

27. A compound according to claim 26 wherein Y represents a covalent bond and n is 0 or 1; or a pharmaceutically acceptable salt thereof.

28. A compound according to claim 27 wherein n is 1; or a pharmaceutically acceptable salt thereof.

29. A compound according to claim 15 wherein the R1 aryl is substituted by one or more of the following: heteroaryl, heterocyclic, aryl, $C_{1-3}$ alkoxy optionally substituted by one to three F; aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen; ureido; or $C_{1-3}$ substituted alkyl;

wherein said $C_{1-3}$ substituted alkyl is substituted with at least one substituent selected from the group consisting of: $C_{1-3}$ alkyl optionally substituted by one to three fluorines; $C_{2-3}$ alkenyl; $C_{2-3}$ alkynyl; $C_{1-2}$ alkoxy optionally substituted by one to three fluorines; sulfanyl; sulfinyl; sulfonyl; oxo; hydroxy; mercapto; amino; guanidino; carboxy; aminocarbonyl; aryl; aryloxy; heteroaryl; heteroaryloxy; heterocyclic; aminosulfonyl; sulfonylamino; carboxyamide; ureido; nitro; cyano; and halogen; or a pharmaceutically acceptable salt thereof.

30. A compound according to claim 19 wherein the R1 heterocyclic is substituted by one or more of the following: heteroaryl, heterocyclic, aryl, $C_{1-3}$ alkoxy optionally substituted by one to three F; aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen; ureido; or $C_{1-3}$ substituted alkyl;

wherein said $C_{1-3}$ substituted alkyl is substituted with at least one substituent selected from the group consisting of: $C_{1-3}$ alkyl optionally substituted by one to three fluorines; $C_{2-3}$ alkenyl; $C_{2-3}$ alkynyl; $C_{1-2}$ alkoxy optionally substituted by one to three fluorines; sulfanyl; sulfinyl; sulfonyl; oxo; hydroxy; mercapto; amino; guanidino; carboxy; aminocarbonyl; aryl; aryloxy; heteroaryl; heteroaryloxy; heterocyclic; aminosulfonyl; sulfonylamino; carboxyamide; ureido; nitro; cyano; and halogen; or a pharmaceutically acceptable salt thereof.

31. A compound according to claim 3 wherein:

R is selected from the group consisting of:
$C_{2-6}$ alkyl optionally substituted by alkoxy or halogen; or $(CH_2)_n$—$_{3-6}$ carbocycle optionally substituted by alkoxy or halogen;

R1 is selected from the group consisting of:
hydrogen, optionally substituted aryl, optionally substituted heteroaryl, optionally substituted heterocyclic, and $C_{1-3}$ substituted alkyl;
wherein said $C_{1-3}$ substituted alkyl is substituted with at least one substituent selected from the group consisting of $C_{1-3}$ alkyl optionally substituted by one to three fluorines; $C_{1-2}$ alkoxy optionally substituted by one to three fluorines; hydroxy; aryl; aryloxy; heteroaryl; heteroaryloxy; and heterocyclic;

Y represents $CH_2$ or a covalent bond; and n is an integer from 0 to 2;

or a pharmaceutically acceptable salt thereof.

32. A pharmaceutical composition comprising a compound according to claim 21 or a pharmaceutically acceptable salt thereof and a pharmaceutical carrier.

33. A compound which is:
N-Hydroxy-N-[(2R)-3-[N'-(1,2,4-benzotriazin-3-yl)-hydrazino]-2-(cyclohexylmethyl)-3-oxopropyl]-formamide;
N-Hydroxy-N-((2R)-2-(cyclohexylmethyl)-3-{N'-[7-(methyloxy)-1,2,4-benzotriazin-3-yl]-hydrazino}-3-oxopropyl)-formamide;
N-Hydroxy-N-((2R)-2-(cyclopentylmethyl)-3-{N'-[7-(methyloxy)-1,2,4-benzotriazin-3-yl]-hydrazino}-3-oxopropyl)-formamide;
N-Hydroxy-N-{(2R)-2-(cyclopentylmethyl)-3-[N'-(5-methyl-1,2,4-benzotriazin-3-yl)hydrazino]-3-oxopropyl}-formamide;
N-Hydroxy-N-{(2R)-2-(cyclopentylmethyl)-3-[N'-(7-methyl-1,2,4-benzotriazin-3-yl)-hydrazino]-3-oxopropyl}-formamide; or
N-Hydroxy-N-[(2R)-3-[N'-(6-chloro-1,2,4-benzotriazin-3-yl)-hydrazino]-2-(cyclopentylmethyl)-3-oxopropyl]-formamide; or a pharmaceutically acceptablesalt thereof.

34. A pharmaceutical composition comprising a compound according to claim 33 or a pharmaceutically acceptable salt thereof and a pharmaceutical carrier.

35. A compound which is:
N-Hydroxy-N-[(2R)-5-methyl-2-({N'-[7-(methyloxy)-1,2,4-benzotriazin-3-yl]-hydrazino}-carbonyl)-hexyl]-formamide;
N-Hydroxy-N-((2R)-2-{[N'-(1,2,4-benzotriazin-3-yl)-hydrazino]-carbonyl}-6-methylheptyl)-formamide;
N-Hydroxy-N-((2R)-2-{[N'-(7-chloro-1,2,4-benzotriazin-3-yl)hydrazino]carbonyl}-6-methylheptyl)-formamide;
N-Hydroxy-N-((2R)-2-{[N'-(7-fluoro-1,2,4-benzotriazin-3-yl)-hydrazino]-carbonyl}-6-methylheptyl)-formamide;
N-Hydroxy-N-((2R)-6-methyl-2-{[N'-(5-methyl-1,2,4-benzotriazin-3-yl)-hydrazino]-carbonyl}-heptyl)-formamide;
N-Hydroxy-N-((2R)-7,7,7-trifluoro-2-{[N'-(5-methyl-1,2,4-benzotriazin-3-yl)-hydrazino]-carbonyl}-heptyl)-formamide;
N-Hydroxy-N-((2R)-7,7,7-trifluoro-2-{[N'-(7-methyl-1,2,4-benzotriazin-3-yl)-hydrazino]-carbonyl}-heptyl) formamide;
N-Hydroxy-N-[(2R)-6-methyl-2-({N'-[7-(methyloxy)-1,2,4-benzotriazin-3-yl]-hydrazino}-carbonyl)-heptyl]-formamide;

N-Hydroxy-N-((2R)-2-{[N'-(1,2,4-benzotriazin-3-yl)hydrazino]-carbonyl}-octyl)-formamide; or N-Hydroxy-N-[(2R)-2-({N'-[7-(methyloxy)-1,2,4-benzotriazin-3-yl]-hydrazino}-carbonyl)-octyl]-formamide; or a pharmaceutcially acceptable salt thereof.

36. A pharmaceutical composition comprising a compound according to claim 35 or a pharmaceutically acceptable salt thereof and a pharmaceutical carrier.

37. A compound which is:

N-Hydroxy-N-{(R)-2-[N'-(4-trifluoromethyl-pyrimidin-2-yl)-hydrazinocarbonyl]-heptyl}-formamide;

N-{(R)-2-[N'-(5-Fluoro-4-morpholin-4-yl-pyrimidin-2-yl)-hydrazinocarbonyl]-heptyl}-N-hydroxy-formamide;

N-{(R)-2-[N'-(5-Fluoro-4-methylamino-pyrimidin-2-yl)-hydrazinocarbonyl]-heptyl}-N-hydroxy-formamide;

N-{(R)-2-[N'-(Dimethylamino-fluoro-pyrimidin-2-yl)-hydrazinocarbonyl]-heptyl}-N-hydroxy-formamide;

N-((R)-2-{N'-[(Ethyl-methyl-amino)-fluoro-pyrimidin-2-yl]-hydrazinocarbonyl}-heptyl)-N-hydroxy-formamide;

N-{(R)-2-[N'-(4-Azetidin-1-yl-5-fluoro-pyrimidin-2-yl)-hydrazinocarbonyl]-heptyl}-N-hydroxy-formamide;

N-Hydroxy-N-{(R)-2-[N'-(morpholin-4-yl-trifluoromethyl-pyrimidin-2-yl)-hydrazinocarbonyl]-heptyl}-formamide;

N-Hydroxy-N-((R)-2-{N'-[(4-methyl-piperazin-1-yl)-trifluoromethyl-pyrimidin-2-yl]-hydrazinocarbonyl}-heptyl)-formamide;

N-Hydroxy-N-((R)-2-{N'-[(4-pyrimidin-2-yl-piperazin-1-yl)-trifluoromethyl-pyrimidin-2-yl]-hydrazinocarbonyl}-heptyl)-formamide;

N-{(R)-2-[N'-(4-Ethyl-6-morpholin-4-yl-pyrimidin-2-yl)-hydrazinocarbonyl]-heptyl}-N-hydroxy-formamide;

N-((R)-2-{N'-[4-Ethyl-6-(4-methyl-piperazin-1-yl)-pyrimidin-2-yl]-hydrazinocarbonyl}-heptyl)-N-hydroxy-formamide;

N-{(R)-2-[N'-(4-Furan-2-yl-pyrimidin-2-yl)-hydrazinocarbonyl]-heptyl}-N-hydroxy-formamide;

N-Hydroxy-N-[(2R)-2-({N'-[4-(furan-3-yl)-pyrimidin-2-yl]-hydrazino}-carbonyl)-heptyl]-formamide; or 2-(N'-{(R)-2-[(Formyl-hydroxy-amino)-methyl]-heptanoyl}-hydrazino)-4-trifluoromethyl-pyrimidine-5-carboxylic acid methyl ester; or a pharmaceutically acceptable salt thereof.

38. A pharmaceutical composition comprising a compound according to claim 37 or a pharmaceutically acceptable salt thereof and a pharmaceutical carrier.

39. A compound which is:

N-Hydroxy-N-[(2R)-2-(cyclopentylmethyl)-3-oxo-3-{N'-[4-(trifluoromethyl)-pyrimidin-2-yl]-hydrazino}-propyl]-formamide;

N-Hydroxy-N-((2R)-2-(cyclohexylmethyl)-3-{N'-[4-(cyclopropylamino)-5-fluoro-pyrimidin-2-yl]hydrazino}-3-oxopropyl)-formamide;

N-Hydroxy-N-((2R)-2-(cyclopentylmethyl)-3-{N'-[4-(morpholin-4-yl)-6-(trifluoromethyl)-pyrimidin-2yl]-hydrazino}-3-oxopropyl)-formamide;

N-Hydroxy-N-((2R)-2-(cyclopentylmethyl)-3-{N'-[4-[(2-hydroxyethyl)-(methyl)-amino]-6-(trifluoromethyl)-pyrimidin-2-yl]-hydrazino}-3-oxopropyl)-formamide;

N-{(R)-4-Cyclopentyl-2-[N'-(4-trifluoromethyl-pyrimidin-2-yl)-hydrazinocarbonyl]-butyl}-N-hydroxy-formamide; or N-{(R)-2-Cyclopentyl-2-[N'-(morpholin-4-yl-4-trifluoromethyl-pyrimidin-2-yl)-hydrazinocarbonyl]-ethyl}-N-hydroxy-formamide; or a pharmaceutically acceptable salt thereof.

40. A pharmaceutical composition comprising a compound according to claim 39 or a pharmaceutically acceptable salt thereof and a pharmaceutical carrier.

41. A compound which is:

N-{(R)-2-[N'-(4-Ethyl-6-morpholin-4-yl-[1,3,5]triazin-2-yl)-hydrazinocarbonyl]-heptyl}-N-hydroxy-formamide;

N-Hydroxy-N-[(R)-2-(N'-{4-isopropyl-6-[(2-methoxyethyl)-methyl-amino]-[1,3,5]triazin-2-yl}-hydrazinocarbonyl)-heptyl]-formamide;

N-{(R)-2-[N'-(Dimethylamino-propyl-[1,3,5]triazin-2-yl)-hydrazinocarbonyl]-heptyl}-N-hydroxy-formamide;

N-{(R)-2-[N'-(4-Cyclopropyl-6-morpholin-4-yl-[1,3,5]triazin-2-yl)-hydrazinocarbonyl]-heptyl}-N-hydroxy-formamide;

N-((R)-2-{N'-[4-Cyclopropyl-6-(4-ethyl-piperazin-1-yl)-[1,3,5]triazin-2-yl]-hydrazinocarbonyl}-heptyl)-N-hydroxy-formamide;

N-{(R)-2-[N'-(Cyclopropyl-dimethylamino-[1,3,5]triazin-2-yl)-hydrazinocarbonyl]-heptyl}-N-hydroxy-formamide;

N-((R)-2-{N'-[Cyclopropyl-(ethyl-methyl-amino)-[1,3,5]triazin-2-yl]-hydrazinocarbonyl}-heptyl)-N-hydroxy-formamide;

N-{(R)-2-[N'-(4-Cyclopropyl-6-pyrrolidin-1-yl[1,3,5]triazin-2-yl)-hydrazinocarbonyl]-heptyl}-N-hydroxy-formamide; or N-((R)-2-{N'-[(Cyclopropyl-methyl-amino)-ethyl-[1,3,5]triazin-2-yl]-hydrazinocarbonyl}-heptyl)-N-hydroxy-formamide; or a pharmaceutcially acceptable salt thereof.

42. A pharmaceutical composition comprising a compound according to claim 41 or a pharmaceutically acceptable salt thereof and a pharmaceutical carrier.

43. A compound which is:

N-{(R)-3-Cyclopentyl-2-[N'-(4-ethyl-6-morpholin-4-yl-[1,3,5]triazin-2-yl)-hydrazinocarbonyl]-propyl}-N-hydroxy-formamide;

N-((R)-3-Cyclopentyl-2-{N'-[4-ethyl-6-(4-ethyl-piperazin-1-yl)-[1,3,5]triazin-2-yl]-hydrazinocarbonyl}-propyl)-N-hydroxy-formamide;

N-{(R)-3-Cyclopentyl-2-[N'-(4-cyclopropylamino-6-ethyl-[1,3,5]triazin-2-yl)-hydrazinocarbonyl]-propyl}-N-hydroxy-formamide;

N-Hydroxy-N-[(2R)-2-(cyclopentylmethyl)-3-(N'-{4-ethyl-6-[ethyl(methyl)amino]-1,3,5-triazin-2-yl}-hydrazino)-3-oxopropyl]-formamide;

N-Hydroxy-N-((2R)-2-(cyclopentylmethyl)-3-{N'-[4-(dimethylamino)-6-ethyl-1,3,5-triazin-2-yl]-hydrazino}-3-oxopropyl)-formamide;

N-{(R)-2-[N'-(Dimethylamino-ethyl-[1,3,5]triazin-2-yl)-hydrazinocarbonyl]-2-(4-methyl-cyclohexyl)-ethyl}-N-Hydroxy-formamide; or N-{(R)-2-Cycloheptyl-2-[N'-(dimethylamino-ethyl-[1,3,5]triazin-2-yl)-hydrazinocarbonyl]-ethyl}-N-hydroxy-formamide; or a pharmaceutically acceptable salt thereof.

44. A pharmaceutical composition comprising a compound according to claim 43 or a pharmaceutically acceptable salt thereof and a pharmaceutical carrier.

* * * * *